(12) United States Patent
Tao

(10) Patent No.: US 9,458,464 B2
(45) Date of Patent: Oct. 4, 2016

(54) TREATMENT OF NEUROPATHIC PAIN

(71) Applicant: THE JOHNS HOPKINS UNIVERSITY, Baltimore, MD (US)

(72) Inventor: Yuanxiang Tao, Boonton, NJ (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/312,152

(22) Filed: Jun. 23, 2014

(65) Prior Publication Data

US 2015/0368652 A1    Dec. 24, 2015

(51) Int. Cl.

| | |
|---|---|
| A61K 31/70 | (2006.01) |
| C07H 21/02 | (2006.01) |
| C07H 21/04 | (2006.01) |
| C12N 15/113 | (2010.01) |
| A61K 31/711 | (2006.01) |
| C12N 5/00 | (2006.01) |
| C12Q 1/68 | (2006.01) |

(52) U.S. Cl.
CPC ......... *C12N 15/1138* (2013.01); *A61K 31/711* (2013.01); *C12N 15/113* (2013.01); *C12N 2310/111* (2013.01); *C12N 2310/113* (2013.01)

(58) Field of Classification Search
None
See application file for complete search history.

(56) References Cited

U.S. PATENT DOCUMENTS

| | | | |
|---|---|---|---|
| 4,797,368 A | 1/1989 | Carter | |
| 5,093,246 A | 3/1992 | Cech | |
| 5,432,272 A | 7/1995 | Benner | |
| 5,478,745 A | 12/1995 | Samulski | |
| 5,672,695 A | 9/1997 | Eckstein | |
| 5,691,176 A | 11/1997 | Lebkowski | |
| 5,693,531 A | 12/1997 | Chiorini | |
| 5,849,571 A | 12/1998 | Glorioso | |
| 5,880,102 A | 3/1999 | George | |
| 6,001,983 A | 12/1999 | Benner | |
| 6,156,303 A | 12/2000 | Russell | |
| 6,210,393 B1 | 4/2001 | Brisken | |
| 6,218,108 B1 | 4/2001 | Kool | |
| 6,248,878 B1 | 6/2001 | Matulic-Adamic | |
| 6,268,213 B1 | 7/2001 | Samulski | |
| 6,303,362 B1 | 10/2001 | Kay | |
| 6,326,385 B1 | 12/2001 | Wickenden | |
| 7,045,344 B2 | 5/2006 | Kay | |
| 8,003,622 B2 | 8/2011 | Wolfe | |
| 2006/0030534 A1 | 2/2006 | Dorn | |
| 2007/0009899 A1 | 1/2007 | Mounts | |
| 2007/0254362 A1 | 11/2007 | Quay | |
| 2007/0274990 A1 | 11/2007 | Morris et al. | |
| 2011/0112175 A1 | 5/2011 | Wolfe | |

FOREIGN PATENT DOCUMENTS

| | | |
|---|---|---|
| WO | 9206180 A1 | 4/1992 |
| WO | 9207065 A1 | 4/1992 |
| WO | 9220316 A2 | 11/1992 |
| WO | 9222635 A1 | 12/1992 |
| WO | 9314188 A1 | 7/1993 |
| WO | 9315187 A1 | 8/1993 |
| WO | 9320221 A1 | 10/1993 |
| WO | 9811244 A2 | 3/1998 |
| WO | 9961601 A2 | 12/1999 |
| WO | 0028061 A2 | 5/2000 |
| WO | 2004094636 A1 | 11/2004 |
| WO | 2008020435 A1 | 2/2008 |

OTHER PUBLICATIONS

Zhao et al (2013) A long noncoding RNA contributes to neuropathic pain by silencing Kcna2 in primary afferent neurons. Nat Neurosci. Aug. 2013;16(8):1024-31. doi: 10.1038/nn.3438. Epub Jun. 23, 2013.

Han et al (2013) Making antisense of pain. Nat Neurosci. Aug. 2013;16(8):986-7. doi: 10.1038/nn.3475.

Fan et al (2014) Impaired neuropathic pain and preserved acute pain in rats overexpressing voltage-gated potassium channel subunit Kv1.2 in primary afferent neurons. Mol Pain. Jan. 29, 2014;10:8. doi: 10.1186/1744-8069-10-8.

Sakai et al (2013) miR-7a alleviates the maintenance of neuropathic pain through regulation of neuronal excitability. Brain. Sep. 2013;136(Pt 9):2738-50. doi: 10.1093/brain/awt191. Epub Jul. 16, 2013.

Tsantoulas et al (2012) Sensory neuron downregulation of the Kv9.1 potassium channel subunit mediates neuropathic pain following nerve injury. J Neurosci. Nov. 28, 2012;32(48):17502-13. doi: 10.1523/JNEUROSCI.3561-122012.

Kim et al (2002) Downregulation of voltage-gated potassium channel alpha gene expression in dorsal root ganglia following chronic constriction injury of the rat sciatic nerve. Brain Res Mol Brain Res. 2002 Sep. 30, 2002;105(1-2):146-52.

Jensen et al (2008) Unlocked nucleic acid (UNA) and UNA derivatives: Thermal denaturation studies. Nucleic Acids Symp Ser (2008) 52 (1): 133-134 doi:10.1093/nass/nrn068.

Limback et al (1994) Summary: the modified nucleosides of RNA. Nucleic Acids Res. Jun. 25, 1994;22(12):2183-96.

(Continued)

*Primary Examiner* — Sean McGarry

(74) *Attorney, Agent, or Firm* — Johns Hopkins Technology Transfer

(57) ABSTRACT

The present invention relates to the field of neurology. More specifically, the present invention provides methods and composition useful for treating neuropathic pain. In a specific embodiment, the present invention provides a recombinant Kcna2 sense fragment. In another embodiment, the present invention provides a method of treating neuropathic pain comprising the step of administering a composition comprising a recombinant Kcna2 sense fragment.

10 Claims, 39 Drawing Sheets

(56) References Cited

OTHER PUBLICATIONS

Burgin et al (1996) Chemically modified hammerhead ribozymes with improved catalytic rates. Biochemistry. Nov. 12, 1996;35(45):14090-7.
Schweitzer et al (1994) Aromatic Nonpolar Nucleosides as Hydrophobic Isosteres of Pyrimidine and Purine Nucleosides. J Org Chem. Dec. 1, 1994;59(24):7238-7242.
Berger et al (2000) Universal bases for hybridization, replication and chain termination. Nucleic Acids Res. Aug. 1, 2000;28(15):2911-4.
Moran et al (1997) Difluorotoluene, a Nonpolar Isostere for Thymine, Codes Specifically and Efficiently for Adenine in DNA Replication. J Am Chem Soc. Feb. 26, 1997;119(8):2056-2057.
Morales et al (1999) Minor Groove Interactions between Polymerase and DNA: More Essential to Replication than Watson-Crick Hydrogen Bonds? J Am Chem Soc. Feb. 14, 1999;121(10):2323-2324.
Guckian et al (1996) Experimental Measurement of Aromatic Stacking Affinities in the Context of Duplex DNA. J Am Chem Soc. Aug. 28, 1996;118(34):8182-8183.
Morales et al (2000) Varied Molecular Interactions at the Active Sites of Several DNA Polymerases: Nonpolar Nucleoside Isosteres as Probes. J Am Chem Soc. Feb. 16, 2000;122(6):1001-1007.
McMinn et al (1999) Efforts toward Expansion of the Genetic Alphabet: DNA Polymerase Recognition of a Highly Stable, Self-Pairing Hydrophobic Base. J Am Chem Soc 121:11585-11586.
Guckian et al (1998) Structure and Base Pairing Properties of a Replicable Nonpolar Isostere for Deoxyadenosine. J Org Chem. 1998;63(26):9652-9656.
Moran et al (1997) A thymidine triphosphate shape analog lacking Watson-Crick pairing ability is replicated with high sequence selectivity. Proc Natl Acad Sci U S A. Sep. 30, 1997;94(20):10506-11.
Das et al (2002) Design and synthesis of N-nonpolar nucleobase dipeptides: application of the Ugi reaction for the preparation of dipeptides having fluoroarylalkyl groups appended to the nitrogen atom. Perkin Trans 1:197-206.
Shibata et al (2001) Synthesis of nonpolar peptide nucleic acid monomers containing fluoroaromatics. J Chem Soc Perkin Trans 1:1605-1611.
Wu et al (2000) Efforts toward Expansion of the Genetic Alphabet: Optimization of Interbase Hydrophobic Interactions. J Am Chem Soc 122:7621-7632.
O'Neill et al (2002) A highly effective nonpolar isostere of deoxyguanosine: synthesis, structure, stacking, and base pairing. J Org Chem. Aug. 23, 2002;67(17):5869-75.
Chaudhuri et al (1995) Very High Affinity DNA Recognition by Bicyclic and Cross-Linked Oligonucleotides. J Am Chem Soc. Oct. 1, 1995;117(42):10434-10442.
Vanaerschot et al (1995) An acyclic 5-nitroindazole nucleoside analogue as ambiguous nucleoside. Nucleic Acids Res. Nov. 11, 1995;23(21):4363-70.
Loakes et al (1995) 3-Nitropyrrole and 5-nitroindole as universal bases in primers for DNA sequencing and PCR Nucleic Acids Res. Jul. 11, 1995;23(13):2361-6.
Loakes et al (1994) 5-Nitroindole as an universal base analogue. Nucleic Acids Res. Oct. 11, 1994;22(20):4039-43.
Wahl et al (1987) Molecular hybridization of immobilized nucleic acids: theoretical concepts and practical considerations. Methods Enzymol. 1987;152:399-407.
Kimmel et al (1987) Identification and characterization of specific clones: strategy for confirming the validity of presumptive clones. Methods Enzymol. 1987;152:507-11.
Fink et al (2011) Gene therapy for pain: a perspective. Pain Management, vol. 1, No. 5, pp. 379-381.
Grunstein et al (1975) Colony hybridization: a method for the isolation of cloned DNAs that contain a specific gene. Proc Natl Acad Sci U S A. Oct. 1975;72(10):3961-5.
Karlin et al (1990) Methods for assessing the statistical significance of molecular sequence features by using general scoring schemes. Proc Natl Acad Sci U S A. Mar. 1990;87(6):2264-8.
Karlin et al (1993) Applications and statistics for multiple high-scoring segments in molecular sequences. Proc Natl Acad Sci U S A. Jun. 15, 1993;90(12):5873-7.
Altschul et al (1990) Basic local alignment search tool. J Mol Biol. Oct. 5, 1990;215(3):403-10.
Altschul et al (1997) Gapped Blast and PSI-Blast: a new generation of protein database search programs. Nucleic Acids Res. Sep. 1, 1997;25(17):3389-402.
Turner et al (1987) Improved Parameters for Prediction of RNA Structure Cold Spring Harb Symp Quant Biol 1987 52: 123-133.
Frier et al (1986) Improved free-energy parameters for predictions of RNA duplex stability. Proc Natl Acad Sci U S A. Dec. 1986;83(24):9373-7.
Turner et al (1987) Free Energy Increments for Hydrogen Bonds in Nucleic Acid Base Pairs. J Am Chem Soc 109:3783-3785.
Gao et al (2004) Clades of Adeno-associated viruses are widely disseminated in human tissues. J Virol. Jun. 2004;78(12):6381-8.
Srivistava et al (1983) Nucleotide sequence and organization of the adeno-associated virus 2 genome. J Virol. Feb. 1983;45(2):555-64.
Chiorini et al (1988) Cloning of adeno-associated virus type 4 (AAV4) and generation of recombinant AAV4 particles. J Virol. Sep. 1997;71(9):6823-33.
Chiorini et al (1999) Cloning and characterization of adeno-associated virus type 5. J Virol. Feb. 1999;73(2):1309-19.
Bantel-Schaal et al (1999) Human adeno-associated virus type 5 is only distantly related to other known primate helper-dependent parvoviruses. J Virol. Feb. 1999;73(2):939-47.
Xiao et al (1999) Gene therapy vectors based on adeno-associated virus type 1. J Virol. May 1999;73(5):3994-4003.
Muramatsu et al (1996) Nucleotide sequencing and generation of an infectious clone of adeno-associated virus 3. Virology. Jul. 1, 1996;221(1):208-17.
Shade et al (1986) Nucleotide sequence and genome organization of human parvovirus B19 isolated from the serum of a child during aplastic crisis. J Virol. Jun. 1986;58(3):921-36.
Gao et al (2002) Novel adeno-associated viruses from rhesus monkeys as vectors for human gene therapy. Proc Natl Acad Sci U S A. Sep. 3, 2002;99(18):11854-9. Epub Aug. 21, 2002.
Fink et al (2011) Gene therapy for pain: results of a phase I clinical trial. Ann Neurol. Aug. 2011;70(2):207-12. doi: 10.1002/ana.22446. Epub Jul. 27, 2011.
Yamamoto et al (1980) Identification of a functional promoter in the long terminal repeat of Rous sarcoma virus. Cell. Dec. 1980;22(3):787-97.
Hutvagner et al (2002) RNAi: nature abhors a double-strand. Curr Opin Genet Dev. Apr. 2002;12(2):225-32.
Hammond et al (2001) Post-transcriptional gene silencing by double-stranded RNA Nat Rev Genet. Feb. 2001;2(2):110-9.
Sharp et al (2001) RNA interference-2001. Genes Dev. Mar. 1, 2001;15(5):485-90.
Chiu et al (2002) RNAi in human cells: basic structural and functional features of small interfering RNA. Mol Cell. Sep. 2002;10(3):549-61.
Elbashir et al (2001) Duplexes of 21-nucleotide RNAs mediate RNA interference in cultured mammalian cells. Nature. May 24, 2001;411(6836):494-8.
Zeng et al (2002) Both natural and designed micro RNAs can inhibit the expression of cognate mRNAs when expressed in human cells. Mol Cell. Jun. 2002;9(6):1327-33.
Paddison et al (2002) Short hairpin RNAs (shRNAs) induce sequence-specific silencing in mammalian cells. Genes Dev. Apr. 15, 2002;16(8):948-58.
Lee et al (2002) Expression of small interfering RNAs targeted against HIV-1 rev transcripts in human cells. Nat Biotechnol. May 2002;20(5):500-5.
Paul et al (2002) Effective expression of small interfering RNA in human cells. Nat Biotechnol. May 2002;20(5):505-8.
Tuschl et al (2002) Expanding small RNA interference. Nat Biotechnol. May 2002;20(5):446-8.

(56) References Cited

OTHER PUBLICATIONS

Yu et al (2002) RNA interference by expression of short-interfering RNAs and hairpin RNAs in mammalian cells. Proc Natl Acad Sci U S A. Apr. 30, 2002;99(9):6047-52. Epub Apr. 23, 2002.

McManus et al (2002) Gene silencing using micro-RNA designed hairpins. RNA. Jun. 2002;8(6):842-50.

Sui et al (2002) A DNA vector-based RNAi technology to suppress gene expression in mammalian cells. Proc Natl Acad Sci U S A. Apr. 16, 2002;99(8):5515-20.

Rossi et al (1994) Practical ribozymes. Making ribozymes work in cells. Curr Biol. May 1, 1994;4(5):469-71.

Kynast, K., et al. (2013) Novel findings in pain processing pathways: implications for miRNAs as future therapeutic targets, Expert Rev Neurother vol. 13, No. 5, pp. 515-525.

Shi, G., et al. (2013) Increased miR-195 aggravates neuropathic pain by inhibiting autophagy following peripheral nerve injury, GLIA, vol. 61, No. 4, pp. 504-512.

Takeda, M., et al. (2011) Potassium channels as a potential therapeutic target for trigeminal neuropathic and Inflammatory pain, Molecular Pain, vol. 7, No. 5.

FIG. 9B

SEQUENCE LISTING

<160> NUMBER OF SEQ ID NOS: 18

<210> SEQ ID NO 1
<211> LENGTH: 2520
<212> TYPE: DNA
<213> ORGANISM: Rattus norvegicus
<220> FEATURE:
<221> NAME/KEY: misc_feature
<222> LOCATION: (1)..(2520)
<223> OTHER INFORMATION: Rat long non-coding Kcna2 RNA/cDNA (antisense
      Kcna2 RNA/cDNA) 5' to 3'

<400> SEQUENCE: 1

```
ggtgtggggg ctatgagggg gctgcattgt gcctttctga gatgctggct ccatgggtga      60
ctctcatctt tggaaacctg taagtcggtg ataaagattt catgaaagcc atgataaata     120
ttctgtgttc taaatcaaaa atcaaaagat caaaagtcac ttgcacgact attgctttcc     180
atgcagaacc agatgcacac tgtagaacac tgactacaat gcaggctatt atgcaatatc     240
tgcattagtc ctgttgagct gtgagtacat taataggttt caatcagaca tcagttaaca     300
ttttggtaat attcacatag tttgtgttag ccaaggtaca gttggctgtt tttaagttct     360
cctctctaaa gtcctcatta ctgttgttta ctccctcctg tatctccatg taatcagact     420
tacttatggt agaggcactt ctacttttct ttaggtcagg ggaggacggg atctttggac     480
aacttgtcac ttgcaagtac tgggcctgct cctctccctc tgtctcccgg tggtagaagt     540
agttgaaatt agacactatg cagggactg taaggcaat ggttaacaca cctgcaattg      600
cacacagaga acccactatc tttcccccaa tggtagttgg aaccatgtct ccatagccta     660
cagttgtcat ggagacgact gcccaccaga aggcatccgg gatgctgggg aactgggaat     720
ctcgctcatc agcttctgca aaatagacag cactagagaa gaggatgacc ccaatgaaga     780
ggaagaatat caggaggccc aattccctca tgctggcttt gagggtctga cctagaatct     840
gcagaccttt ggagtgtctg gacaacttga aaatcctaaa gactcttacc aaccggatga     900
cacggagaat ggccagtgac atggcctgct ggccttgctg ggcgtcctct ggcttctcag     960
ctaactctgt cccagggtg ataaagtaag ggatgatagc cacaatgtca atgatgttca    1020
tgatgttggt gaagaagcca gctttgctgg gacaggcaaa gaatctaacc agaaactcaa    1080
aggagaacca gatgatgcag agagtctcta cgatgaagaa agggtcggtg aaggaggtgg    1140
actgctggta cccaatggtg ctgttggaat aggtgtggaa ggtcaccca ccaccatgca     1200 tgtcctcgtt ctcatcccgg aagatgggca aggtttccag acagaagctg acgatcgaga    1260
tcagaatgac catcacagat acaatggcta tgatcctggc cggccctgag ctctcagggt    1320
attcaaagag aagccacacc tgtctctgaa actcattttc aggcagggga cgttcttctt    1380
ccttgatgta gccttcatcc tcccgaaaca tctccattgc ctcttctcct agctcataaa    1440
accggatttc ttcagagaag atatctaagg gcacattcac aggtcgcctc aacctgcccc    1500
cagactggta gtagtacaaa atggcatcaa agctagggcg gttgcgatca aaaaagtact    1560
catttcggag gggatcaaag tacctcatcc gtttcttggg gtctcctaag agggtctctg    1620
ggaactgggc taaggtcttt agctgagtct cgaaccgcag gcctgagatg ttaatcacca    1680
ctctctcaca gcactcgtgg tctgcctctg ggtcataggt gtcttgaggg tgcccaggga    1740
gggcagcagc ctcatccact gggtctccgg tagccactgt cataattggg gctgaggagt    1800
gtgctttatt ttatgccttc cagctgcctg cagcagggaa ctcagggtgc tggtaactgg    1860
gccccaggaa acacagaagc attagtctgc gctcctgtag gaaagaccca gagccttctg    1920
```

| | |
|---|---|
| tgagttggag tcacagcctc ctttggctgg ccaggcagga gcctgaggtt ctcttccttg | 1980 |
| aagagcagat ctgatgccac agatacacaa ataggcagct cagtcccgt cacatcttct | 2040 |
| cacttgagct ggaaataatg gtgagtcatt ctgagcagga gggcaggtcc tcgaggtgtg | 2100 |
| ctctaggact ggatgggct tgagggacag tgagatgctt agccagggc acagcgcacg | 2160 |
| acttgaggag agtggagctt gggtctgaag cctttggaag aaggaggta agatgcacag | 2220 |
| ctcagcaaaa gccagagtcc tcctggctgt cctcaggagg tgtgacgttg ccaaaactcc | 2280 |
| gtgcagagct cagctggatg ctgcctgggt cgggaggcag gggagagggt agaagttgag | 2340 |
| gagcgcttga gaggttcttg ccaacataat gaagtaggca ggatgaactg atcaatacca | 2400 |
| tcccaggccc gagcgggatc cagccccgag ggagatatgt tgctattatt atgatgctgc | 2460 |
| cagacagaat ctgcagaccc cagttccccc cactccagtc ttctgtttct gcgtcccttt | 2520 |

<210> SEQ ID NO 2
<211> LENGTH: 2520
<212> TYPE: DNA
<213> ORGANISM: Rattus norvegicus
<220> FEATURE:
<221> NAME/KEY: misc_feature
<222> LOCATION: (1)..(2520)
<223> OTHER INFORMATION: Rat long non-coding Kcna2 RNA/cDNA (antisense Kcna2 RNA/cDNA) 3' to 5'

<400> SEQUENCE: 2

| | |
|---|---|
| tttccctgcg tctttgtctt ctgacctcac cccccttgac cccagacgtc taagacagac | 60 |
| cgtcgtagta ttattatcgt tgtatagagg gagccccgac ctagggcgag cccggaccct | 120 |
| accataacta gtcaagtagg acggatgaag taatacaacc gttcttggag agttcgcgag | 180 |
| gagttgaaga tgggagaggg gacggagggc tgggtccgtc gtaggtcgac tcgagacgtg | 240 |
| cctcaaaacc gttgcagtgt ggaggactcc tgtcggtcct cctgagaccg aaaacgactc | 300 |
| gacacgtaga atggaggaag gaaggtttcc gaagtctggg ttcgaggtga gaggagttca | 360 |
| gcacgcgaca cggggaccga ttcgtagagt gacagggagt tcggggtagg tcaggatctc | 420 |
| gtgtggagct cctggacggg aggacgagtc ttactgagtg gtaataaagg tcgagttcac | 480 |
| tcttctacac tgcccctgac tcgacggata aacacataga caccgtagtc tagacgagaa | 540 |
| gttccttctc ttggagtccg aggacggacc ggtcggtttc ctccgacact gaggttgagt | 600 |
| gtcttccgag acccagaaag gatgtcctcg cgtctgatta cgaagacaca aaggaccccg | 660 |
| ggtcaatggt cgtgggactc aagggacgac gtccgtcgac cttccgtatt ttatttcgtg | 720 |
| tgaggagtcg gggttaatac tgtcaccgat ggcctctggg tcacctactc cgacgacggg | 780 |
| agggacccgt gggagttctg tggatactgg gtctccgtct ggtgctcacg acactctctc | 840 |
| accactaatt gtagagtccg gacgccaagc tctgagtcga tttctggaat cgggtcaagg | 900 |
| gtctctggga gaatcctctg gggttctttg cctactccat gaaactaggg gaggctttac | 960 |
| tcatgaaaaa actagcgttg gcgggatcga aactacggta aaacatgatg atggtcagac | 1020 |
| ccccgtccaa ctccgctgga cacttacacg ggaatctata aagagactt ctttaggcca | 1080 |
| aaatactcga tcctcttctc cgttacctct acaaagccct cctacttccg atgtagttcc | 1140 |
| ttcttcttgc aggggacgga cttttactca agtctctgt ccacaccgaa gagaaactta | 1200 |
| tgggactctc gagtcccggc cggtcctagt atcggtaaca tagacactac cagtaagact | 1260 |
| agagctagca gtcgaagaca gacctttgga acgggtagaa ggccctactc ttgctcctgt | 1320 |
| acgtaccacc accccactgg aaggtgtgga taaggttgtc gtggtaaccc atggtcgtca | 1380 |

```
ggtggaggaa gtggctggga agaagtagc atctctgaga cgtagtag accaagagga    1440 aactcaaaga ccaatctaag aaacggacag ggtcgtttcg accgaagaag tggttgtagt  1500
acttgtagta actgtaacac cgatagtagg gaatgaaata gtgggacccc tgtctcaatc  1560
gactcttcgg tctcctgcgg gtcgttccgg tcgtccggta cagtgaccgg taagaggcac  1620
agtaggccaa ccattctcag aaatcctaaa agttcaacag gtctgtgagg tttccagacg  1680
tctaagatcc agtctgggag tttcggtcgt actcccttaa cccggaggac tataagaagg  1740
agaagtaacc ccagtaggag aagagatcac gacagataaa acgtcttcga ctactcgctc  1800
taagggtcaa ggggtcgtag ggcctacgga agaccacccg tcagcagagg tactgttgac  1860
atccgatacc tctgtaccaa ggttgatggt aaccccttt ctatcaccca agagacacac   1920
gttaacgtcc acacaattgg taacggaatg gtcaggaca gtatcacaga ttaaagttga   1980
tgaagatggt ggccctctgt ctccctctcc tcgtccgggt catgaacgtt cactgttcaa   2040
caggtttcta gggcaggagg ggactggatt tcttttcatc ttcacggaga tggtattcat   2100
tcagactaat gtacctctat gtcctccctc atttgttgtc attactcctg aaatctctcc    2160
tcttgaattt ttgtcggttg acatggaacc gattgtgttt gatacactta taatgggtttt   2220 acaattgact acagactaac tttgataat acatgagtg tcgagttgtc ctgattacgt     2280
ctataacgta ttatcggacg taacatcagt cacaagatgt cacacgtaga ccaagacgta   2340
cctttcgtta tcagcacgtt cactgaaaac tagaaaacta aaaactaaat cttgtgtctt    2400
ataaatagta ccgaaagtac tttagaaata gtggctgaat gtccaaaggt ttctactctc    2460
agtgggtacc tcggtcgtag agtctttccg tgttacgtcg ggggagtatc ggggggtgtgg  2520
```

<210> SEQ ID NO 3
<211> LENGTH: 2520
<212> TYPE: DNA
<213> ORGANISM: Rattus norvegicus
<220> FEATURE:
<221> NAME/KEY: misc_feature
<222> LOCATION: (1)..(2520)
<223> OTHER INFORMATION: Rat long non-coding Kcna2 sense DNA 5' to 3'

<400> SEQUENCE: 3

```
aaagggacgc agaaacagaa gactggagtg gggggaactg gggtctgcag attctgtctg    60
gcagcatcat aataatagca acatatctcc ctcggggctg gatcccgctc gggcctggga   120
tggtattgat cagttcatcc tgcctacttc attatgttgg caagaacctc tcaagcgctc   180
ctcaacttct accctctccc ctgcctcccg acccaggcag catccagctg agctctgcac   240
ggagttttgg caacgtcaca cctcctgagg acagccagga ggactctggc ttttgctgag   300
ctgtgcatct tacctccttc cttccaaagg cttcagaccc aagctccact ctcctcaagt    360
cgtgcgctgt gcccctggct aagcatctca ctgtccctca agccccatcc agtcctagag    420
cacacctcga ggacctgccc tcctgctcag aatgactcac cattatttcc agctcaagtg   480
agaagatgtg acggggactg agctgcctat tgtgtatct gtggcatcag atctgctctt    540
caaggaagag aacctcaggc tcctgcctgg ccagccaaag gaggctgtga ctccaactca   600
cagaaggctc tgggtctttc ctacaggagc gcagactaat gcttctgtgt ttcctggggc   660
ccagttacca gcaccctgag ttccctgctg caggcagctg gaaggcataa aataaagcac    720
actcctcagc cccaattatg acagtggcta ccggagaccc agtggatgag gctgctgccc   780
tccctgggca ccctcaagac acctatgacc cagaggcaga ccacgagtgc tgtgagagag   840
tggtgattaa catctcaggc ctgcggttcg agactcagct aaagacctta gcccagttcc    900
```

```
cagagaccct cttaggagac cccaagaaac ggatgaggta ctttgatccc ctccgaaatg      960 agtactttt  tgatcgcaac cgccctagct ttgatgccat tttgtactac taccagtctg     1020
ggggcaggtt gaggcgacct gtgaatgtgc ccttagatat cttctctgaa gaaatccggt     1080
tttatgagct aggagaagag gcaatggaga tgtttcggga ggatgaaggc tacatcaagg     1140
aagaagaacg tccsctgcct gaaaatgagt tcagagaca ggtgtggctt ctctttgaat      1200
accctgagag ctcagggccg gccaggatca tagccattgt atctgtgatg gtcattctga     1260
tctcgatcgt cagcttctgt ctggaaacct tgcccatctt ccgggatgag aacgaggaca     1320
tgcatggtgg tggggtgacc ttccacacct attccaacag caccattggg taccagcagt     1380
ccacctcctt caccgaccct ttcttcatcg tagagactct ctgcatcatc tggttctcct     1440
ttgagtttct ggttagattc tttgcctgtc ccagcaaagc tggcttcttc accaacatca     1500
tgaacatcat tgacattgtg gctatcatcc cttactttat caccctgggg acagagttag     1560
ctgagaagcc agaggacgcc cagcaaggcc agcaggccat gtcactggcc attctccgtg     1620
tcatccggtt ggtaagagtc tttaggattt tcaagttgtc cagacactcc aaaggtctgc     1680
agattctagg tcagaccctc aaagccagca tgagggaatt gggcctcctg atattcttcc     1740
tcttcattgg ggtcatcctc ttctctagtg ctgtctattt tgcagaagct gatgagcgag     1800
attcccagtt ccccagcatc ccggatgcct tctggtgggc agtcgtctcc atgacaactg     1860
taggctatgg agacatggtt ccaactacca ttgggggaaa gatagtgggt tctctgtgtg     1920
caattgcagg tgtgttaacc attgccttac cagtccctgt catagtgtct aatttcaact     1980
acttctacca ccgggagaca gagggagagg agcaggccca gtacttgcaa gtgacaagtt     2040
gtccaaagat cccgtcctcc cctgacctaa agaaaagtag aagtgcctct accataagta     2100
agtctgatta catggagata caggagggag taaacaacag taatgaggac tttagagagg     2160
agaacttaaa aacagccaac tgtaccttgg ctaaacaaaa ctatgtgaat attaccaaaa     2220
tgttaactga tgtctgattg aaacctatta atgtactcac agctcaacag gactaatgca     2280
gatattgcat aatagcctgc attgtagtca gtgttctaca gtgtgcatct ggttctgcat     2340
ggaaagcaat agtcgtgcaa gtgacttttg atcttttgat ttttgattta gaacacagaa     2400
tatttatcat ggctttcatg aaatctttat caccgactta caggtttcca aagatgagag     2460
tcacccatgg agccagcatc tcagaaaggc acaatgcagc cccctcatag ccccacacc      2520
```

<210> SEQ ID NO 4
<211> LENGTH: 2267
<212> TYPE: DNA
<213> ORGANISM: Homo sapiens
<220> FEATURE:
<221> NAME/KEY: misc_feature
<222> LOCATION: (1)..(2267)
<223> OTHER INFORMATION: Human Kcna2 mRNA 5'3'
<220> FEATURE:
<221> NAME/KEY: 5'UTR
<222> LOCATION: (1)..(621)
<220> FEATURE:
<221> NAME/KEY: CDS
<222> LOCATION: (622)..(2121)
<220> FEATURE:
<221> NAME/KEY: 3'UTR
<222> LOCATION: (2122)..(2267)

<400> SEQUENCE: 4

```
gtgctccctg ccgaggagat gtgagggatt ttctcttggg ggagaaatca gtggtcgagc       60
gcctgcccag ctcaaatgcc accggctca  gagggaggcc tgcggcccag ggatcccgga      120
```

```
gggagagcaa cgtcacacct cctgaggaca gccaggactc cagcttttgc tgagctttgc    180
atcttgcctc cttccttcaa aaggctccag gcccatgctg gctgtcttc aagtcccgca    240 tgcccctggc caggcacctc accgcccctc cagcccagcc caatcctaga gctcacctcc    300
aggacccaga gtctgccctt ctgcccagaa tgactcacca ttatttctag ctcgagtgag    360
aagacgtgat gaggagttgg gctgcctgtt ggtgcatctc agattcctgc agcatctgat    420
cagctctgca aggaagagag cttcacgtct ctggtcagcc aagcgaggct gtctctccag    480
ctctcagaga gctctcgggg ctcctgca ggagaccagg ccaatgctcc tgtgcttcct    540
ggggccagta gcagcaccct gagctccctg ccaccaggca gctgaaaggc atagcgtgag    600
gtgcttctct cagtcccaat t atg aca gtg gcc acc gga gac cca gca gac    651
                        Met Thr Val Ala Thr Gly Asp Pro Ala Asp
                         1               5                  10 gag gct gct gcc ctc cct ggg cac cca cag gac acc tat gac cca gag    699
Glu Ala Ala Ala Leu Pro Gly His Pro Gln Asp Thr Tyr Asp Pro Glu
             15                  20                  25 gca gac cac gag tgc tgt gag agg gtg gtg atc aac atc tca ggg ctg    747
Ala Asp His Glu Cys Cys Glu Arg Val Val Ile Asn Ile Ser Gly Leu
         30                  35                  40 cgg ttt gag acc cag cta aag acc tta gcc cag ttt cca gag acc ctc    795
Arg Phe Glu Thr Gln Leu Lys Thr Leu Ala Gln Phe Pro Glu Thr Leu
     45                  50                  55 tta ggg gac cca aag aaa cga atg agg tac ttt gac ccc ctc cga aat    843
Leu Gly Asp Pro Lys Lys Arg Met Arg Tyr Phe Asp Pro Leu Arg Asn
 60                  65                  70 gag tac ttt ttc gat cgg aac cgc cct agc ttt gat gcc att ttg tac    891
Glu Tyr Phe Phe Asp Arg Asn Arg Pro Ser Phe Asp Ala Ile Leu Tyr
 75                  80                  85                  90 tac tac cag tca ggg ggc cga ttg agg cga cct gtg aat gtg ccc tta    939
Tyr Tyr Gln Ser Gly Gly Arg Leu Arg Arg Pro Val Asn Val Pro Leu
                 95                 100                 105 gat ata ttc tct gaa gaa att cgg ttt tat gag ctg gga gaa gaa gcg    987
Asp Ile Phe Ser Glu Glu Ile Arg Phe Tyr Glu Leu Gly Glu Glu Ala
             110                 115                 120 atg gag atg ttt cgg gaa gat gaa ggc tac atc aag gag gaa gag cgt   1035
Met Glu Met Phe Arg Glu Asp Glu Gly Tyr Ile Lys Glu Glu Glu Arg
         125                 130                 135 cct ctg cct gaa aat gag ttt cag aga caa gtg tgg ctt ctc ttt gaa   1083
Pro Leu Pro Glu Asn Glu Phe Gln Arg Gln Val Trp Leu Leu Phe Glu
     140                 145                 150 tac cca gag agc tca ggg cct gcc agg att ata gct att gtg tct gtc   1131
Tyr Pro Glu Ser Ser Gly Pro Ala Arg Ile Ile Ala Ile Val Ser Val
155                 160                 165                 170 atg gtg att ctg atc tca att gtc agc ttc tgt ctg gaa aca ttg ccc   1179
Met Val Ile Leu Ile Ser Ile Val Ser Phe Cys Leu Glu Thr Leu Pro
                 175                 180                 185 atc ttc cgg gat gag aat gaa gac atg cat ggt agt ggg gtg acc ttc   1227
Ile Phe Arg Asp Glu Asn Glu Asp Met His Gly Ser Gly Val Thr Phe
             190                 195                 200 cac acc tat tcc aac agc acc atc ggg tac cag cag tcc act tcc ttc   1275
His Thr Tyr Ser Asn Ser Thr Ile Gly Tyr Gln Gln Ser Thr Ser Phe
         205                 210                 215 aca gac cct ttc ttc att gta gag aca ctc tgc atc atc tgg ttc tcc   1323
Thr Asp Pro Phe Phe Ile Val Glu Thr Leu Cys Ile Ile Trp Phe Ser
     220                 225                 230 ttt gaa ttc ttg gtg agg ttc ttt gcc tgt ccc agc aaa gcc ggc ttc   1371
Phe Glu Phe Leu Val Arg Phe Phe Ala Cys Pro Ser Lys Ala Gly Phe
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ttc | acc | aac | atc | atg | aac | atc | att | gac | att | gtg | gcc | atc | atc | ccc | tac | 1419 |
| Phe | Thr | Asn | Ile | Met | Asn | Ile | Ile | Asp | Ile | Val | Ala | Ile | Ile | Pro | Tyr |      |
| 	  | 	  | 	  | 	  | 	  | 255 | 	  | 	  | 	  | 	  | 260 | 	  | 	  | 	  | 	  | 265 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ttc | atc | acc | ctg | ggg | aca | gag | ttg | gct | gag | aag | cca | gag | gac | gct | cag | 1467 |
| Phe | Ile | Thr | Leu | Gly | Thr | Glu | Leu | Ala | Glu | Lys | Pro | Glu | Asp | Ala | Gln |      |
| 	  | 	  | 270 | 	  | 	  | 	  | 	  | 275 | 	  | 	  | 	  | 	  | 280 | 	  | 	  | 	  |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| caa | ggc | cag | cag | gcc | atg | tca | ctg | gcc | atc | ctc | cgt | gtc | atc | cgg | ttg | 1515 |
| Gln | Gly | Gln | Gln | Ala | Met | Ser | Leu | Ala | Ile | Leu | Arg | Val | Ile | Arg | Leu |      |
| 	  | 	  | 	  | 285 | 	  | 	  | 	  | 	  | 290 | 	  | 	  | 	  | 	  | 295 | 	  | 	  |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gta | aga | gtc | ttt | agg | att | ttc | aag | ttg | tcc | aga | cac | tcc | aaa | ggt | ctc | 1563 |
| Val | Arg | Val | Phe | Arg | Ile | Phe | Lys | Leu | Ser | Arg | His | Ser | Lys | Gly | Leu |      |
| 300 | 	  | 	  | 	  | 	  | 305 | 	  | 	  | 	  | 	  | 310 | 	  | 	  | 	  | 	  | 	  |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| cag | att | cta | ggt | cag | acc | ctc | aaa | gcc | agc | atg | aga | gaa | ttg | ggc | ctc | 1611 |
| Gln | Ile | Leu | Gly | Gln | Thr | Leu | Lys | Ala | Ser | Met | Arg | Glu | Leu | Gly | Leu |      |
| 315 | 	  | 	  | 	  | 	  | 320 | 	  | 	  | 	  | 	  | 325 | 	  | 	  | 	  | 	  | 330 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ctg | ata | ttc | ttt | ctc | ttc | ata | ggg | gtc | atc | ctt | ttc | tct | agt | gct | gtg | 1659 |
| Leu | Ile | Phe | Phe | Leu | Phe | Ile | Gly | Val | Ile | Leu | Phe | Ser | Ser | Ala | Val |      |
| 	  | 	  | 	  | 	  | 335 | 	  | 	  | 	  | 	  | 340 | 	  | 	  | 	  | 	  | 345 | 	  |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| tat | ttt | gca | gag | gcc | gat | gag | cga | gag | tcc | cag | ttc | ccc | agc | atc | cca | 1707 |
| Tyr | Phe | Ala | Glu | Ala | Asp | Glu | Arg | Glu | Ser | Gln | Phe | Pro | Ser | Ile | Pro |      |
| 	  | 	  | 	  | 350 | 	  | 	  | 	  | 	  | 355 | 	  | 	  | 	  | 	  | 360 | 	  | 	  |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gat | gcc | ttc | tgg | tgg | gca | gtc | gtc | tcc | atg | aca | act | gta | ggc | tat | gga | 1755 |
| Asp | Ala | Phe | Trp | Trp | Ala | Val | Val | Ser | Met | Thr | Thr | Val | Gly | Tyr | Gly |      |
| 	  | 	  | 365 | 	  | 	  | 	  | 	  | 370 | 	  | 	  | 	  | 	  | 375 | 	  | 	  | 	  |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gac | atg | gtt | ccg | act | acc | att | ggg | gga | aag | ata | gtg | ggt | tcc | cta | tgt | 1803 |
| Asp | Met | Val | Pro | Thr | Thr | Ile | Gly | Gly | Lys | Ile | Val | Gly | Ser | Leu | Cys |      |
| 	  | 380 | 	  | 	  | 	  | 	  | 385 | 	  | 	  | 	  | 	  | 390 | 	  | 	  | 	  | 	  |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcg | att | gca | ggt | gtg | tta | act | att | gcc | tta | ccg | gtc | cct | gtc | att | gtg | 1851 |
| Ala | Ile | Ala | Gly | Val | Leu | Thr | Ile | Ala | Leu | Pro | Val | Pro | Val | Ile | Val |      |
| 395 | 	  | 	  | 	  | 	  | 400 | 	  | 	  | 	  | 	  | 405 | 	  | 	  | 	  | 	  | 410 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| tcc | aat | ttc | aac | tac | ttc | tac | cac | cgg | gag | aca | gag | gga | gag | gaa | cag | 1899 |
| Ser | Asn | Phe | Asn | Tyr | Phe | Tyr | His | Arg | Glu | Thr | Glu | Gly | Glu | Glu | Gln |      |
| 	  | 	  | 	  | 	  | 415 | 	  | 	  | 	  | 	  | 420 | 	  | 	  | 	  | 	  | 425 | 	  |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcc | caa | tac | ttg | caa | gtg | aca | agc | tgt | cca | aag | atc | cca | tcc | tcc | cct | 1947 |
| Ala | Gln | Tyr | Leu | Gln | Val | Thr | Ser | Cys | Pro | Lys | Ile | Pro | Ser | Ser | Pro |      |
| 	  | 	  | 430 | 	  | 	  | 	  | 	  | 435 | 	  | 	  | 	  | 	  | 440 | 	  | 	  | 	  |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gac | cta | aag | aaa | agt | aga | agt | gcc | tct | acc | att | agt | aag | tct | gat | tac | 1995 |
| Asp | Leu | Lys | Lys | Ser | Arg | Ser | Ala | Ser | Thr | Ile | Ser | Lys | Ser | Asp | Tyr |      |
| 	  | 	  | 	  | 445 | 	  | 	  | 	  | 	  | 450 | 	  | 	  | 	  | 	  | 455 | 	  | 	  |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| atg | gag | atc | cag | gag | ggt | gta | aat | aac | agt | aat | gag | gac | ttt | aga | gag | 2043 |
| Met | Glu | Ile | Gln | Glu | Gly | Val | Asn | Asn | Ser | Asn | Glu | Asp | Phe | Arg | Glu |      |
| 	  | 460 | 	  | 	  | 	  | 	  | 465 | 	  | 	  | 	  | 	  | 470 | 	  | 	  | 	  | 	  |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gaa | aac | ttg | aaa | aca | gcc | aac | tgt | acc | ttg | gct | aac | aca | aac | tat | gtg | 2091 |
| Glu | Asn | Leu | Lys | Thr | Ala | Asn | Cys | Thr | Leu | Ala | Asn | Thr | Asn | Tyr | Val |      |
| 475 | 	  | 	  | 	  | 	  | 480 | 	  | 	  | 	  | 	  | 485 | 	  | 	  | 	  | 	  | 490 |      |

|     |     |     |     |     |     |     |     |     |                        |      |
|-----|-----|-----|-----|-----|-----|-----|-----|-----|------------------------|------|
| aat | att | acc | aaa | atg | tta | act | gat | gtc | tga ttgaaaccta ttaccgtact | 2141 |
| Asn | Ile | Thr | Lys | Met | Leu | Thr | Asp | Val |                        |      |
| 	  | 	  | 	  | 	  | 495 | 	  | 	  | 	  | 	  |                        |      |

| | |
|---|---|
| cacagctcaa tggaactaat gcagatgttg cataatagcc tgcattgtag tcagtgtgtt | 2201 |
| ctacagtgtg tatctggttc tgcatggaaa gcaatagttg tgcaagtgaa aaaaaaaaa | 2261 |
| aaaaaa | 2267 |

<210> SEQ ID NO 5
<211> LENGTH: 499
<212> TYPE: PRT
<213> ORGANISM: Homo sapiens

<400> SEQUENCE: 5

```
Met Thr Val Ala Thr Gly Asp Pro Ala Asp Glu Ala Ala Ala Leu Pro
1               5                   10                  15

Gly His Pro Gln Asp Thr Tyr Asp Pro Glu Ala Asp His Glu Cys Cys
            20                  25                  30

Glu Arg Val Val Ile Asn Ile Ser Gly Leu Arg Phe Glu Thr Gln Leu
            35                  40                  45

Lys Thr Leu Ala Gln Phe Pro Glu Thr Leu Leu Gly Asp Pro Lys Lys
50                      55                  60

Arg Met Arg Tyr Phe Asp Pro Leu Arg Asn Glu Tyr Phe Phe Asp Arg
65                  70                  75                  80

Asn Arg Pro Ser Phe Asp Ala Ile Leu Tyr Tyr Gln Ser Gly Gly
                85                  90                  95

Arg Leu Arg Arg Pro Val Asn Val Pro Leu Asp Ile Phe Ser Glu Glu
            100                 105                 110

Ile Arg Phe Tyr Glu Leu Gly Glu Glu Ala Met Glu Met Phe Arg Glu
            115                 120                 125

Asp Glu Gly Tyr Ile Lys Glu Glu Arg Pro Leu Pro Glu Asn Glu
            130                 135                 140

Phe Gln Arg Gln Val Trp Leu Leu Phe Glu Tyr Pro Glu Ser Ser Gly
145                 150                 155                 160

Pro Ala Arg Ile Ile Ala Ile Val Ser Val Met Val Ile Leu Ile Ser
                165                 170                 175

Ile Val Ser Phe Cys Leu Glu Thr Leu Pro Ile Phe Arg Asp Glu Asn
            180                 185                 190

Glu Asp Met His Gly Ser Gly Val Thr Phe His Thr Tyr Ser Asn Ser
            195                 200                 205

Thr Ile Gly Tyr Gln Gln Ser Thr Ser Phe Thr Asp Pro Phe Phe Ile
210                 215                 220

Val Glu Thr Leu Cys Ile Ile Trp Phe Ser Phe Glu Phe Leu Val Arg
225                 230                 235                 240

Phe Phe Ala Cys Pro Ser Lys Ala Gly Phe Phe Thr Asn Ile Met Asn
                245                 250                 255

Ile Ile Asp Ile Val Ala Ile Ile Pro Tyr Phe Ile Thr Leu Gly Thr
            260                 265                 270

Glu Leu Ala Glu Lys Pro Glu Asp Ala Gln Gln Gly Gln Gln Ala Met
            275                 280                 285

Ser Leu Ala Ile Leu Arg Val Ile Arg Leu Val Arg Val Phe Arg Ile
            290                 295                 300

Phe Lys Leu Ser Arg His Ser Lys Gly Leu Gln Ile Leu Gly Gln Thr
305                 310                 315                 320

Leu Lys Ala Ser Met Arg Glu Leu Gly Leu Leu Ile Phe Phe Leu Phe
                325                 330                 335

Ile Gly Val Ile Leu Phe Ser Ser Ala Val Tyr Phe Ala Glu Ala Asp
            340                 345                 350

Glu Arg Glu Ser Gln Phe Pro Ser Ile Pro Asp Ala Phe Trp Trp Ala
            355                 360                 365

Val Val Ser Met Thr Thr Val Gly Tyr Gly Asp Met Val Pro Thr Thr
370                 375                 380

Ile Gly Gly Lys Ile Val Gly Ser Leu Cys Ala Ile Ala Gly Val Leu
385                 390                 395                 400

Thr Ile Ala Leu Pro Val Pro Val Ile Val Ser Asn Phe Asn Tyr Phe
                405                 410                 415
```

```
Tyr His Arg Glu Thr Glu Gly Glu Glu Gln Ala Gln Tyr Leu Gln Val
            420                 425                 430

Thr Ser Cys Pro Lys Ile Pro Ser Ser Pro Asp Leu Lys Lys Ser Arg
        435                 440                 445

Ser Ala Ser Thr Ile Ser Lys Ser Asp Tyr Met Glu Ile Gln Glu Gly
    450                 455                 460

Val Asn Asn Ser Asn Glu Asp Phe Arg Glu Glu Asn Leu Lys Thr Ala
465                 470                 475                 480

Asn Cys Thr Leu Ala Asn Thr Asn Tyr Val Asn Ile Thr Lys Met Leu
                485                 490                 495

Thr Asp Val

<210> SEQ ID NO 6
<211> LENGTH: 351
<212> TYPE: DNA
<213> ORGANISM: Rattus norvegicus
<220> FEATURE:
<221> NAME/KEY: misc_feature
<222> LOCATION: (1)..(351)
<223> OTHER INFORMATION: Rat Kcna2 sense fragment -311 to +40
<220> FEATURE:
<221> NAME/KEY: 5'UTR
<222> LOCATION: (1)..(311)
<223> OTHER INFORMATION: 5' UTR -311 to 1

<400> SEQUENCE: 6
acctcgagga cctgccctcc tgctcagaat gactcaccat tatttccagc tcaagtgaga      60
agatgtgacg ggactgagct gcctatttgt gtatctgtgg catcagatct gctcttcaag     120
gaagagaacc tcagctcctg cctgccagcc aaaggaggct gtgactccaa ctcacagaag     180
gctctgggtc tttcctacag gagcgcagac taatgcttct gtgtttcctg ggcccagtt     240 accagcaccc tgagttccct gctgcaggca gctggaaggc ataaaataaa gcacactcct     300 cagcccccaat tatgacagtg ctaccggag acccagtgga tgaggctgct g              351

<210> SEQ ID NO 7
<211> LENGTH: 621
<212> TYPE: DNA
<213> ORGANISM: Homo sapiens
<220> FEATURE:
<221> NAME/KEY: misc_feature
<222> LOCATION: (1)..(621)
<223> OTHER INFORMATION: Human Kcna2 mRNA 5' untranslated region

<400> SEQUENCE: 7
gtgctccctg ccgaggagat gtgagggatt ttctcttggg ggagaaatca gtggtcgagc      60
gcctgcccag ctcaaatgcc acccggctca gagggaggcc tgcggcccag ggatcccgga     120
gggagagcaa cgtcacacct cctgaggaca gccaggactc cagcttttgc tgagctttgc     180
atcttgcctc cttccttcaa aaggctccag gcccatgctc ggctgtcttc aagtcccgca     240 tgccctggc caggcacctc accgcccctc agcccagcc caatcctaga gctcacctcc       300
aggacccaga gtctgcccct ctgcccagaa tgactcacca ttatttctag ctcgagtgag     360
aagacgtgat gaggagttgg gctgcctgtt ggtgcatctc agattcctgc agcatctgat     420
cagctctgca aggaagagag cttcacgtct ctggtcagcc aagcgaggct gtctctccag     480
ctctcagaga gctctcgggg ctctcctgca ggagaccagg ccaatgctcc tgtgcttcct     540
ggggccagta gcagcaccct gagctccctg ccaccaggca gctgaaaggc atagcgtgag     600
gtgcttctct cagtcccaat t                                               621
```

<210> SEQ ID NO 8
<211> LENGTH: 460
<212> TYPE: DNA
<213> ORGANISM: Homo sapiens
<220> FEATURE:
<221> NAME/KEY: misc_feature
<222> LOCATION: (1)..(460)
<223> OTHER INFORMATION: Human Kcna2 sense fragment -400 to +60

<400> SEQUENCE: 8

```
gctgtcttca agtcccgcat gcccctggcc aggcacctca ccgcccctcc agcccagccc      60
aatcctagag ctcacctcca ggacccagag tctgcccttc tgcccagaat gactcaccat     120
tatttctagc tcgagtgaga agacgtgatg aggagttggg ctgcctgttg gtgcatctca     180
gattcctgca gcatctgatc agctctgcaa ggaagagagc ttcacgtctc tggtcagcca     240
agcgaggctg tctctccagc tctcagagag ctctcggggc tctcctgcag agaccaggc     300
caatgctcct gtgcttcctg gggccagtag cagcaccctg agctccctgc caccaggcag     360
ctgaaaggca tagcgtgagg tgcttctctc agtcccaatt atgacagtgg ccaccggaga     420
cccagcagac gaggctgctg ccctcccctgg gcacccacag                           460
```

<210> SEQ ID NO 9
<211> LENGTH: 445
<212> TYPE: DNA
<213> ORGANISM: Homo sapiens
<220> FEATURE:
<221> NAME/KEY: misc_feature
<222> LOCATION: (1)..(445)
<223> OTHER INFORMATION: Human Kcna2 sense fragment -390 to +55

<400> SEQUENCE: 9

```
agtcccgcat gcccctggcc aggcacctca ccgcccctcc agcccagccc aatcctagag      60
ctcacctcca ggacccagag tctgcccttc tgcccagaat gactcaccat tatttctagc     120
tcgagtgaga agacgtgatg aggagttggg ctgcctgttg gtgcatctca gattcctgca     180
gcatctgatc agctctgcaa ggaagagagc ttcacgtctc tggtcagcca agcgaggctg     240
tctctccagc tctcagagag ctctcggggc tctcctgcag agaccaggc caatgctcct     300
gtgcttcctg gggccagtag cagcaccctg agctccctgc caccaggcag ctgaaaggca     360
tagcgtgagg tgcttctctc agtcccaatt atgacagtgg ccaccggaga cccagcagac     420
gaggctgctg ccctcccctgg gcacc                                           445
```

<210> SEQ ID NO 10
<211> LENGTH: 430
<212> TYPE: DNA
<213> ORGANISM: Homo sapiens
<220> FEATURE:
<221> NAME/KEY: misc_feature
<222> LOCATION: (1)..(430)
<223> OTHER INFORMATION: Human Kcna2 sense fragment -380 to +50

<400> SEQUENCE: 10

```
gcccctggcc aggcacctca ccgcccctcc agcccagccc aatcctagag ctcacctcca      60
ggacccagag tctgcccttc tgcccagaat gactcaccat tatttctagc tcgagtgaga     120
agacgtgatg aggagttggg ctgcctgttg gtgcatctca gattcctgca gcatctgatc     180
agctctgcaa ggaagagagc ttcacgtctc tggtcagcca agcgaggctg tctctccagc     240
tctcagagag ctctcggggc tctcctgcag agaccaggc caatgctcct gtgcttcctg     300
gggccagtag cagcaccctg agctccctgc caccaggcag ctgaaaggca tagcgtgagg     360
```

```
tgcttctctc agtcccaatt atgacagtgg ccaccggaga cccagcagac gaggctgctg    420
ccctccctgg                                                            430

<210> SEQ ID NO 11
<211> LENGTH: 415
<212> TYPE: DNA
<213> ORGANISM: Homo sapiens
<220> FEATURE:
<221> NAME/KEY: misc_feature
<222> LOCATION: (1)..(415)
<223> OTHER INFORMATION: Human Kcna2 sense fragment -370 to +45

<400> SEQUENCE: 11
aggcacctca ccgcccctcc agcccagccc aatcctagag ctcacctcca ggacccagag    60
tctgcccttc tgcccagaat gactcaccat tatttctagc tcgagtgaga agacgtgatg   120
aggagttggg ctgcctgttg gtgcatctca gattcctgca gcatctgatc agctctgcaa   180
ggaagagagc ttcacgtctc tggtcagcca agcgaggctg tctctccagc tctcagagag   240
ctctcggggc tctcctgcag gagaccaggc caatgctcct gtgcttcctg gggccagtag   300
cagcaccctg agctccctgc caccaggcag ctgaaaggca tagcgtgagg tgcttctctc   360
agtcccaatt atgacagtgg ccaccggaga cccagcagac gaggctgctg ccctc        415

<210> SEQ ID NO 12
<211> LENGTH: 400
<212> TYPE: DNA
<213> ORGANISM: Homo sapiens
<220> FEATURE:
<221> NAME/KEY: misc_feature
<222> LOCATION: (1)..(400)
<223> OTHER INFORMATION: Human Kcna2 sense fragment -360 to +40

<400> SEQUENCE: 12
ccgcccctcc agcccagccc aatcctagag ctcacctcca ggacccagag tctgcccttc    60
tgcccagaat gactcaccat tatttctagc tcgagtgaga agacgtgatg aggagttggg   120
ctgcctgttg gtgcatctca gattcctgca gcatctgatc agctctgcaa ggaagagagc   180
ttcacgtctc tggtcagcca agcgaggctg tctctccagc tctcagagag ctctcggggc   240
tctcctgcag gagaccaggc caatgctcct gtgcttcctg gggccagtag cagcaccctg   300
agctccctgc caccaggcag ctgaaaggca tagcgtgagg tgcttctctc agtcccaatt   360
atgacagtgg ccaccggaga cccagcagac gaggctgctg                         400

<210> SEQ ID NO 13
<211> LENGTH: 400
<212> TYPE: DNA
<213> ORGANISM: Homo sapiens
<220> FEATURE:
<221> NAME/KEY: misc_feature
<222> LOCATION: (1)..(400)
<223> OTHER INFORMATION: Human Kcna2 sense fragment -350-+40

<400> SEQUENCE: 13
ccgcccctcc agcccagccc aatcctagag ctcacctcca ggacccagag tctgcccttc    60
tgcccagaat gactcaccat tatttctagc tcgagtgaga agacgtgatg aggagttggg   120
ctgcctgttg gtgcatctca gattcctgca gcatctgatc agctctgcaa ggaagagagc   180
ttcacgtctc tggtcagcca agcgaggctg tctctccagc tctcagagag ctctcggggc   240
tctcctgcag gagaccaggc caatgctcct gtgcttcctg gggccagtag cagcaccctg   300
```

```
agctccctgc caccaggcag ctgaaaggca tagcgtgagg tgcttctctc agtcccaatt    360
atgacagtgg ccaccggaga cccagcagac gaggctgctg                          400
```

<210> SEQ ID NO 14
<211> LENGTH: 390
<212> TYPE: DNA
<213> ORGANISM: Homo sapiens
<220> FEATURE:
<221> NAME/KEY: misc_feature
<222> LOCATION: (1)..(390)
<223> OTHER INFORMATION: Human Kcna2 sense fragment -340 to +40

<400> SEQUENCE: 14

```
agcccagccc aatcctagag ctcacctcca ggacccagag tctgcccttc tgcccagaat     60
gactcaccat tatttctagc tcgagtgaga agacgtgatg aggagttggg ctgcctgttg    120
gtgcatctca gattcctgca gcatctgatc agctctgcaa ggaagagagc ttcacgtctc    180
tggtcagcca agcgaggctg tctctccagc tctcagagag ctctcggggc tctcctgcag    240
gagaccaggc caatgctcct gtgcttcctg gggccagtag cagcaccctg agctccctgc    300
caccaggcag ctgaaaggca tagcgtgagg tgcttctctc agtcccaatt atgacagtgg    360
ccaccggaga cccagcagac gaggctgctg                                     390
```

<210> SEQ ID NO 15
<211> LENGTH: 380
<212> TYPE: DNA
<213> ORGANISM: Homo sapiens
<220> FEATURE:
<221> NAME/KEY: misc_feature
<222> LOCATION: (1)..(390)
<223> OTHER INFORMATION: Human Kcna2 sense fragment -330 to +40

<400> SEQUENCE: 15

```
aatcctagag ctcacctcca ggacccagag tctgcccttc tgcccagaat gactcaccat     60
tatttctagc tcgagtgaga agacgtgatg aggagttggg ctgcctgttg gtgcatctca    120
gattcctgca gcatctgatc agctctgcaa ggaagagagc ttcacgtctc tggtcagcca    180
agcgaggctg tctctccagc tctcagagag ctctcggggc tctcctgcag gagaccaggc    240
caatgctcct gtgcttcctg gggccagtag cagcaccctg agctccctgc caccaggcag    300
ctgaaaggca tagcgtgagg tgcttctctc agtcccaatt atgacagtgg ccaccggaga    360
cccagcagac gaggctgctg                                                380
```

<210> SEQ ID NO 16
<211> LENGTH: 370
<212> TYPE: DNA
<213> ORGANISM: Homo sapiens
<220> FEATURE:
<221> NAME/KEY: misc_feature
<222> LOCATION: (1)..(370)
<223> OTHER INFORMATION: Human Kcna2 sense fragment -320 to +40

<400> SEQUENCE: 16

```
ctcacctcca ggacccagag tctgcccttc tgcccagaat gactcaccat tatttctagc     60
tcgagtgaga agacgtgatg aggagttggg ctgcctgttg gtgcatctca gattcctgca    120
gcatctgatc agctctgcaa ggaagagagc ttcacgtctc tggtcagcca agcgaggctg    180
tctctccagc tctcagagag ctctcggggc tctcctgcag gagaccaggc caatgctcct    240
gtgcttcctg gggccagtag cagcaccctg agctccctgc caccaggcag ctgaaaggca    300
tagcgtgagg tgcttctctc agtcccaatt atgacagtgg ccaccggaga cccagcagac    360
```

```
gaggctgctg                                                                   370

<210> SEQ ID NO 17
<211> LENGTH: 360
<212> TYPE: DNA
<213> ORGANISM: Homo sapiens
<220> FEATURE:
<221> NAME/KEY: misc_feature
<222> LOCATION: (1)..(360)
<223> OTHER INFORMATION: Human Kcna2 sense fragment -310 to +40

<400> SEQUENCE: 17
ggacccagag tctgcccttc tgcccagaat gactcaccat tatttctagc tcgagtgaga     60
agacgtgatg aggagttggg ctgcctgttg gtgcatctca gattcctgca gcatctgatc    120
agctctgcaa ggaagagagc ttcacgtctc tggtcagcca agcgaggctg tctctccagc    180
tctcagagag ctctcggggc tctcctgcag gagaccaggc caatgctcct gtgcttcctg    240
gggccagtag cagcaccctg agctccctgc caccaggcag ctgaaaggca tagcgtgagg    300
tgcttctctc agtcccaatt atgacagtgg ccaccggaga cccagcagac gaggctgctg    360

<210> SEQ ID NO 18
<211> LENGTH: 350
<212> TYPE: DNA
<213> ORGANISM: Homo sapiens
<220> FEATURE:
<221> NAME/KEY: misc_feature
<222> LOCATION: (1)..(350)
<223> OTHER INFORMATION: Human Kcna2 sense fragment -300 to +40

<400> SEQUENCE: 18
tctgcccttc tgcccagaat gactcaccat tatttctagc tcgagtgaga agacgtgatg     60
aggagttggg ctgcctgttg gtgcatctca gattcctgca gcatctgatc agctctgcaa    120
ggaagagagc ttcacgtctc tggtcagcca agcgaggctg tctctccagc tctcagagag    180
ctctcggggc tctcctgcag gagaccaggc caatgctcct gtgcttcctg gggccagtag    240
cagcaccctg agctccctgc caccaggcag ctgaaaggca tagcgtgagg tgcttctctc    300
agtcccaatt atgacagtgg ccaccggaga cccagcagac gaggctgctg                350
```

TREATMENT OF NEUROPATHIC PAIN

STATEMENT OF GOVERNMENTAL INTEREST

This invention was made with government support under grant no. NS072206, awarded by the National Institutes of Health. The government has certain rights in the invention.

FIELD OF THE INVENTION

The present invention relates to the field of neurology. More specifically, the present invention provides methods and composition useful for treating neuropathic pain.

INCORPORATION-BY-REFERENCE OF MATERIAL SUBMITTED ELECTRONICALLY

This application contains a sequence listing. It has been submitted electronically via EFS-Web as an ASCII text file entitled "P12779-01_ST25.txt." The sequence listing is 33,272 bytes in size, and was created on Jun. 22, 2014. It is hereby incorporated by reference in its entirety.

BACKGROUND OF THE INVENTION

Neuropathic pain is a major public health problem. Treatment for this disorder has had limited success owing to our incomplete understanding of the mechanisms that underlie the induction of neuropathic pain. Nerve injury-induced neuropathic pain is thought to be triggered by abnormal spontaneous activity that arises in neuromas and first-order sensory neurons of the DRG. The abnormal excitability may result from maladaptive changes in gene transcription and translation of receptors, enzymes and voltage-dependent ion channels in the DRG4. Voltage-dependent potassium channels govern cell excitability. Peripheral nerve injury downregulates expression of mRNA and protein for these channels in the DRG, a phenomenon that may contribute to induction of neuropathic pain. However, the molecular mechanisms that underlie this downregulation are still unknown.

SUMMARY OF THE INVENTION

The present invention is based, at least in part, on the discovery that a sense fragment of Kcna2 can be used to treat neuropathic pain. The present inventors recently identified a conserved long non-coding RNA for Kcna2 (also referred to herein as "Kcna2 antisense RNA") in primary sensory neurons of dorsal root ganglion (DRG). Peripheral nerve injury increases Kcna2 antisense RNA expression in injured DRG through activation of myeloid zinc finger protein 1, a transcription factor that binds to the Kcna2 antisense RNA gene promoter. Mimicking this increase downregulates Kcna2, reduces total Kv current, increases excitability in DRG neurons, and produces neuropathic pain symptoms. Blocking this increase reverses nerve injury-induced downregulation of DRG Kcna2 and attenuates development and maintenance of neuropathic pain. These findings confirm native Kcna2 antisense RNA as a new therapeutic target for the treatment of neuropathic pain.

Neuropathic pain is a refractory disease characterized by maladaptive changes in gene transcription and translation in the sensory pathway. Long noncoding RNAs (lncRNAs) are emerging as new players in gene regulation, but how lncRNAs operate in the development of neuropathic pain is unclear. Here we identify a conserved lncRNA, named Kcna2 antisense RNA, for a voltage-dependent potassium channel mRNA, Kcna2, in first-order sensory neurons of rat dorsal root ganglion (DRG). Peripheral nerve injury increased Kcna2 antisense RNA expression in injured DRG through activation of myeloid zinc finger protein 1, a transcription factor that binds to the Kcna2 antisense RNA gene promoter. Mimicking this increase downregulated Kcna2, reduced total voltage-gated potassium current, increased excitability in DRG neurons and produced neuropathic pain symptoms. Blocking this increase reversed nerve injury-induced downregulation of DRG Kcna2 and attenuated development and maintenance of neuropathic pain. These findings suggest endogenous Kcna2 antisense RNA as a therapeutic target for the treatment of neuropathic pain.

As described herein, the present invention provides the first report of this endogenous long non-coding RNA in body cells, including human cells. It also points to new regulation of Kcna mRNA and protein and neuronal excitability. The present invention also provides a new target for preventing and/treating neuropathic pain.

Thus, in one aspect, the present invention provides Kcna2 sense fragments. The fragments can be used to treat pain in a patient in need thereof. In certain embodiments, the pain is neuropathic pain. In another embodiment, the pain is inflammatory pain. In yet another embodiment, the pain is associated with cancer or spinal cord injury. The Kcna2 sense fragments can be administered to a patient in an amount and at a location sufficient to diminish the sensation of pain in the patient.

In one embodiment, the Kcna2 sense fragment comprises SEQ ID NO:5. In another embodiment, the Kcna2 sense fragment consists of SEQ ID NO:5. In a further embodiment, the Kcna2 sense fragment consists essentially of SEQ ID NO:5. The Kcna2 sense fragment can comprise a nucleic acid that is about 90%, about 91%, about 92%, about 93%, about 94%, about 95%, about 96%, about 97%, about 98%, or about 99% of SEQ ID NO:5. In another embodiment, the Kcna2 sense fragment can comprise a fragment of the 5' untranslated region.

In yet another embodiment, the Kcna2 sense fragment comprises one of SEQ ID NOS:7-17. In an alternative embodiment, the Kcna2 sense fragment consists of one of SEQ ID NOS:7-17. The Kcna2 sense fragment can also consist essentially of one of SEQ ID NOS:7-17. The Kcna2 sense fragment can comprise a nucleic acid that is about 90%, about 91%, about 92%, about 93%, about 94%, about 95%, about 96%, about 97%, about 98%, or about 99% of any one of SEQ ID NOS:7-17 or other sequences described herein.

The present invention also provides recombinant vectors. In one embodiment, a recombinant vector comprises a nucleic acid sequence encoding a Kcna2 sense fragment shown in SEQ ID NO:5. In other embodiments, a recombinant vector comprises a nucleic acid sequence encoding a Kcna2 sense fragment shown in any one of SEQ ID NOS:7-17. In further embodiments, a recombinant vector comprises a nucleic acid sequence encoding a Kcna2 sense fragment described herein. In yet another embodiment, the present invention provides a host cell comprising a recombinant vector described herein. The recombinant vector can be a viral vector. In a specific embodiment, the viral vector is an adeno-associated vector.

In another aspect, the present invention provides methods for treating pain. In one embodiment, a method for treating neuropathic pain comprises the step of administering to a patient in need thereof a composition comprising a recombinant Kcna2 sense fragment, wherein the recombinant Kcna2 sense fragment comprises SEQ ID NO:5. In another embodiment, a method for treating neuropathic pain comprises the step of administering to a patient in need thereof a composition comprising a recombinant vector encoding a Kcna2 sense fragment shown in SEQ ID NO:5. In another embodiment, the composition further comprises a pharmaceutically acceptable carrier. In a specific embodiment, the patient is human. In another embodiment, the composition is administered to the dorsal root ganglion or to the spinal cord of the patient. In yet another embodiment, the composition is administered parenterally.

BRIEF DESCRIPTION OF THE FIGURES

FIG. 6 Kcna2 antisense RNA specifically targets Kcna2. (a) Left, representative western blots showing the amounts of Kcna2, Kcna1, Kcna4 and Scn10a protein in HEK-293T cells transfected with control EGFP vector, Kcna2 sense fragment (SE) vector, Kcna2 antisense (AS) vector or Kcna2 SE+Kcna2 AS. Right, statistical summary of the densitometric analysis. n=4 repeats per treatment. F=21.37 for Kcna2, 0.65 for Kcna1, 0.61 for Kcna4 and 0.45 for Scn10a.

Figure 1A:
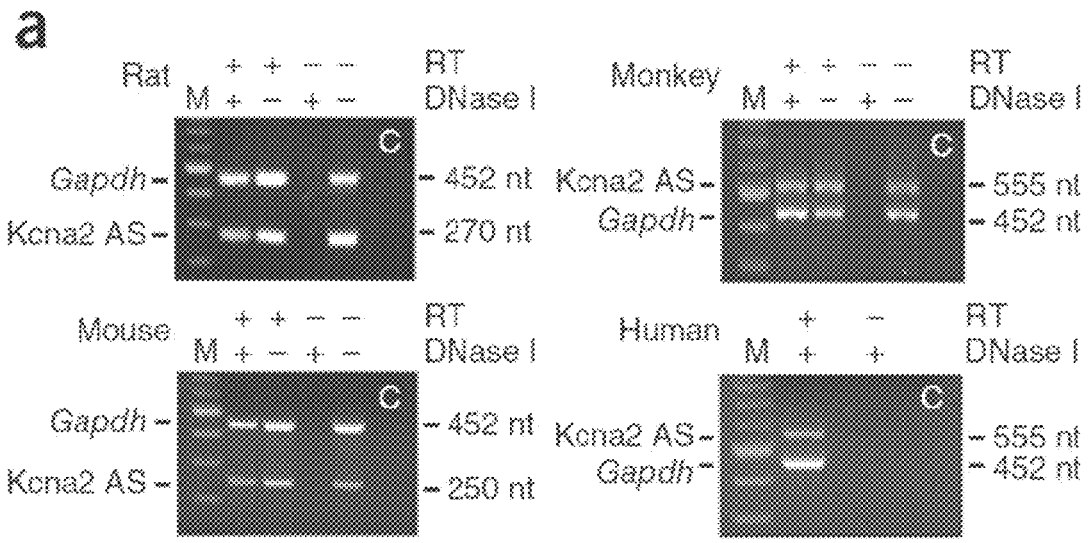
FIG. 1. Identification and expression of Kcna2 antisense RNA in naive dorsal root ganglion. (a) Native Kcna2 antisense (AS) transcripts detected in the DRGs of rat (Sprague-Dawley), mouse (C57/BL6), monkey (*Macaca fascicularis*) and human using reverse transcription (RT)-PCR with strand-specific primers. To exclude genomic DNA contamination, we pretreated the extracted RNA samples with excess DNase I. Gapdh is a control. Without RT primers, neither Gapdh nor Kcna2 AS PCR products were detected in DNase I-treated samples, indicating absence of genomic DNA. n=3 repeated experiments per species. We further confirmed the existence of native Kcna2 AS RNA in the tissues using specific intron-spanning primers. M, 100-bp ladder; C, no-template control. (b) The extent of sequence overlap (blue boxes) between the cDNAs of Kcna2 RNA and Kcna2 AS RNA. (c) Northern blot expression analysis of Kcna2 AS RNA (arrowhead) in the DRG (lane 1) and spinal cord (lane 2) of rats. n=3 repeated experiments. M, RNA marker. (d) In situ hybridization histochemistry showing the distribution of Kcna2 AS RNA in rat DRG. GFP, which is not expressed in mammalian cells, was used as a negative control. n=5 rats. Scale bar, 40 µm. (e) Histogram shows the distribution of Kcna2 AS RNA-positive somata in normal rat DRG.

P<0.01 versus the corresponding EGFP groups. ##P<0.01 versus the corresponding Kcna2 AS vector alone. One-way ANOVA with Tukey post-hoc test. (b) Amounts of Kcna2 AS RNA and of mRNAs for various ion channels in rat DRG cultured neurons transduced with AAV5-EGFP, AAV5-Kcna2 SE, AAV5-Kcna2 AS or AAV5-Kcna2 SE+AAV5-Kcna2 AS. n=3 repeats per treatment. F=10.06 for Kcna2 mRNA, 11.90 for Kcna2 AS RNA, 0.24 for Kcna1 mRNA, 0.65 for Kcna4 mRNA and 0.87 for Scn10a mRNA. P<0.01 versus AAV5-EGFP alone. ##P<0.01 versus the corresponding AAV5-Kcna2 AS alone. One-way ANOVA with Tukey post-hoc test. (c) Levels of Kcna2 AS RNA and mRNAs for various ion channels in the ipsilateral (ipsi) and contralateral (con) L4/5 DRGs 4 and 8 weeks after injection with AAV5-EGFP or AAV5-Kcna2 AS. n=12 rats per treatment. F=15.91 for Kcna2 AS RNA, 20.45 for Kcna2 mRNA, 0.39 for Kcna1 mRNA and 0.56 for Scn10a mRNA. *P<0.05, P<0.01 versus the corresponding EGFP-treated group. Two-way ANOVA with Tukey post-hoc test. (d) Representative western blots of ipsilateral and contralateral L4/5 DRGs 8 weeks after injection with AAV5-EGFP or AAV5-Kcna2 AS. (e) Statistical summary of the densitometric analysis. n=10 rats per group. F=15.51 for Kcna2, 0.35 for Kcna1, 0.78 for Kcna4 and 0.48 for Scn10a. P<0.01 versus corresponding contralateral sides of the AAV5-EGFP-treated group. One-way ANOVA with Tukey post-hoc test. Error bars, s.e.m. Full-length blots are presented in Supplementary FIG. 7.

FIG. 7 Kcna2 antisense RNA overexpression in DRG reduces total voltage-gated potassium current, increases excitability in large and medium DRG neurons and produces neuropathic pain symptoms. (a) Representative traces of total voltage-gated potassium current in large DRG neurons from control- and Kcna2 antisense (AS)-injected rats before or after bath perfusion of 100 nM maurotoxin (MTX). Inset, an EGFP (green)-labeled recording neuron. (b) I-V curve for control- and AS-treated large DRG neurons before or after 100 nM MTX treatment. n=14 cells per group. F=139.21, *P<0.05, P<0.01 versus the AS group. Two-way ANOVA with Tukey post-hoc test. (c,d) Resting membrane potential (RMP, c; t=−4.21 for large, −7.04 for medium and −0.32 for small) and current threshold for pulses ($I_{threshold}$, d; t=3.22 for large, 6.28 for medium and 0.73 for small). n=33 large, 42 medium and 30 small cells from the control group (12 rats). n=43 large, 70 medium and 32 small cells from the AS group (14 rats). P<0.01 versus the corresponding control group. Unpaired Student's t-test. (e) Representative traces of the evoked action potentials (AP) in DRG neurons. (f-h) Numbers of evoked APs from control- and AS-injected rats after application of different currents. Numbers of cells recorded same as in c. F=18.45 for large, 20.65 for medium and 0.67 for small cells. *P<0.05 versus the same stimulation intensity in the control group. Two-way ANOVA with Tukey post-hoc test. (i) Ipsilateral (ipsi) and contralateral (contra) paw withdrawal responses to mechanical (F=38.31) and cold (F=65.77) stimuli from control and AS-injected rats; w, weeks. n=14 rats per group. **P<0.01 versus control on the ipsilateral side at the corresponding time points. Two-way ANOVA with Tukey post-hoc test. Error bars, s.e.m.

Figure 7A:
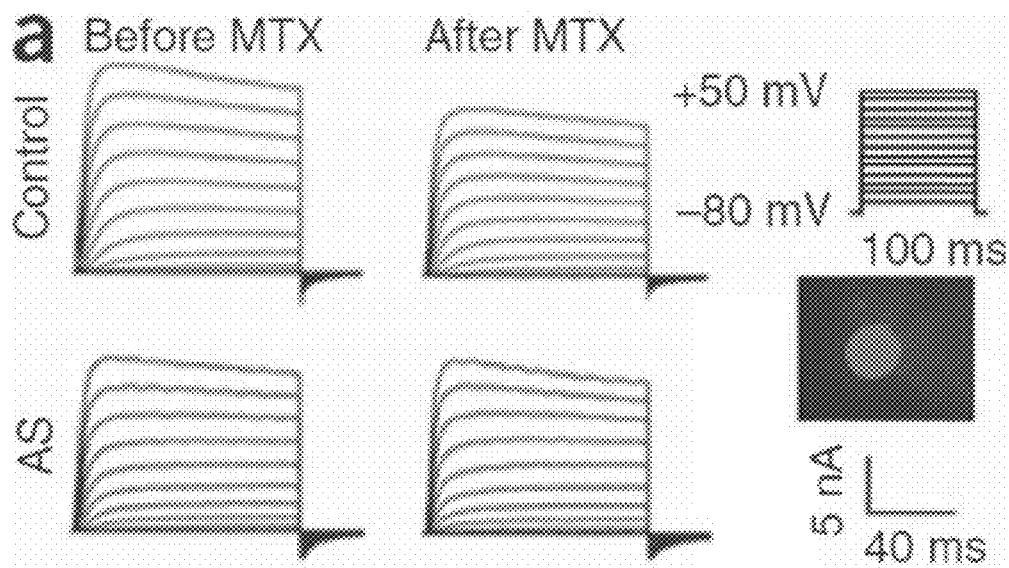
Figure 7B:
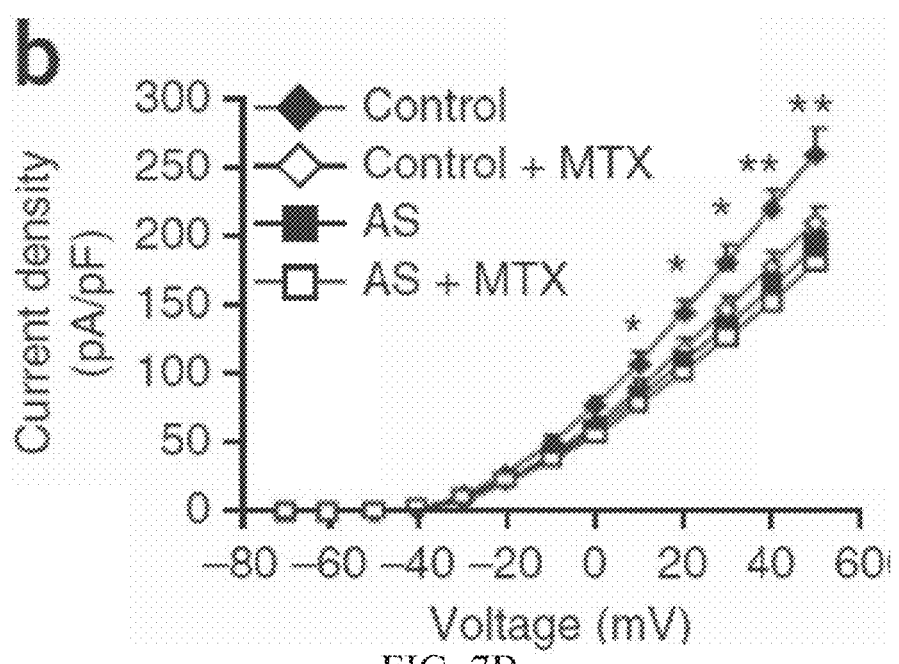
Figure 7C:
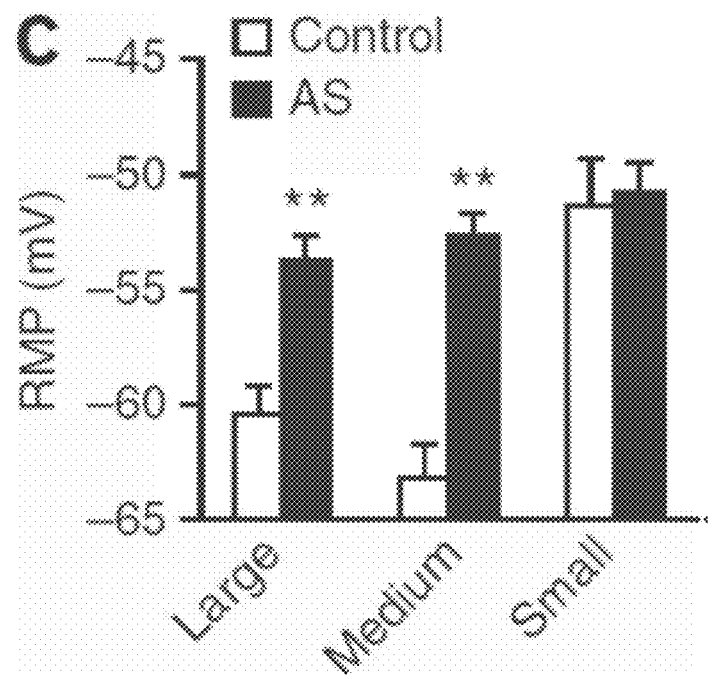
Figure 7D:
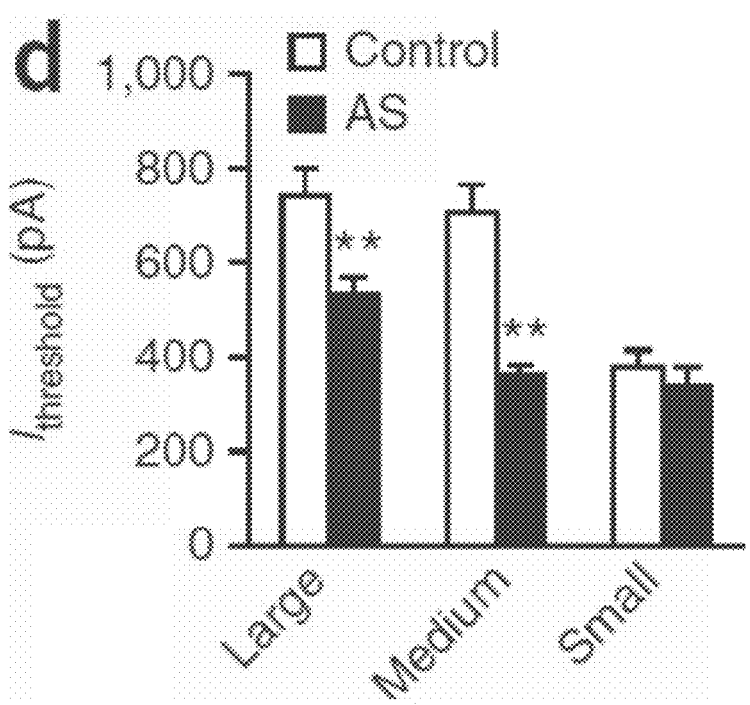
Figure 7E:
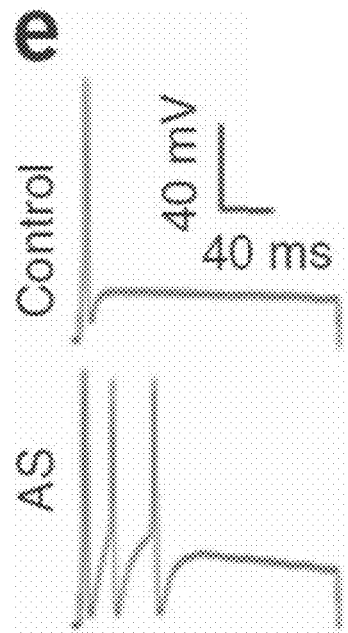
Figure 7F:
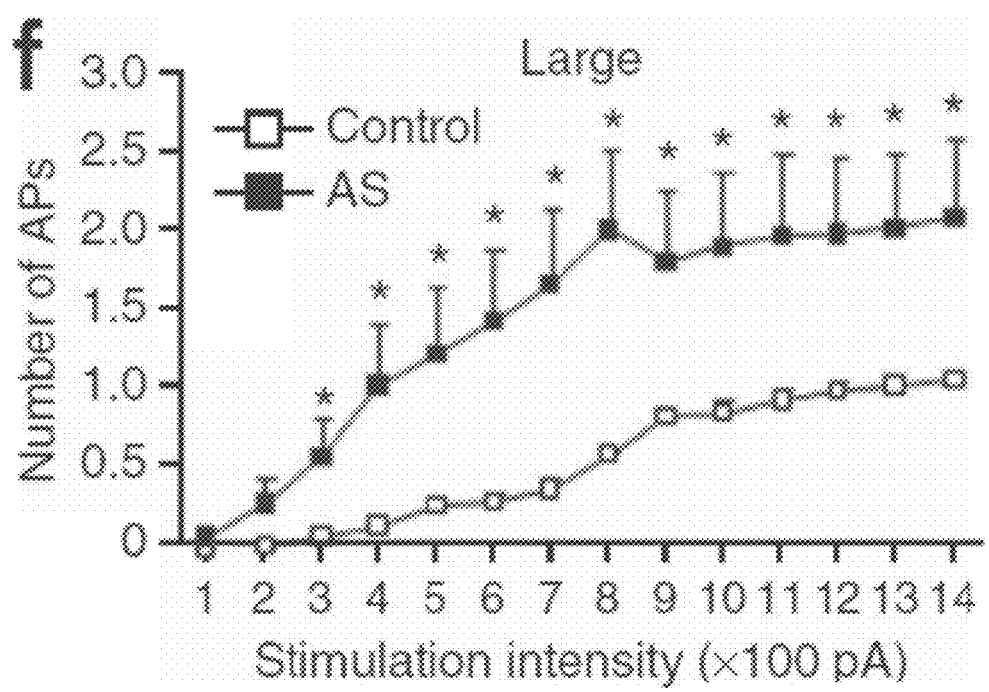
Figure 7G:
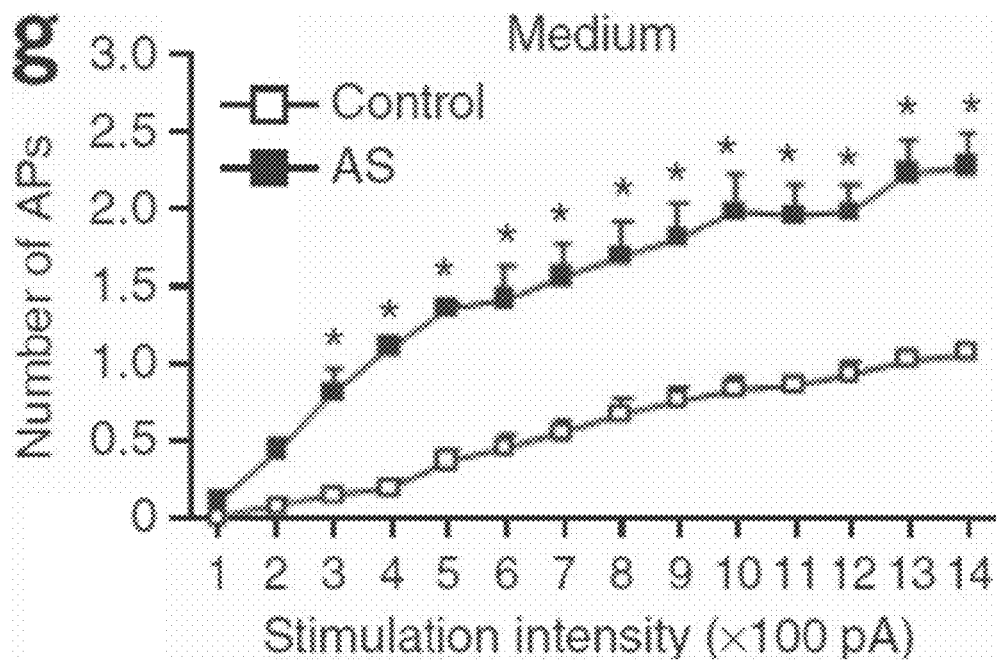
Figure 7H:
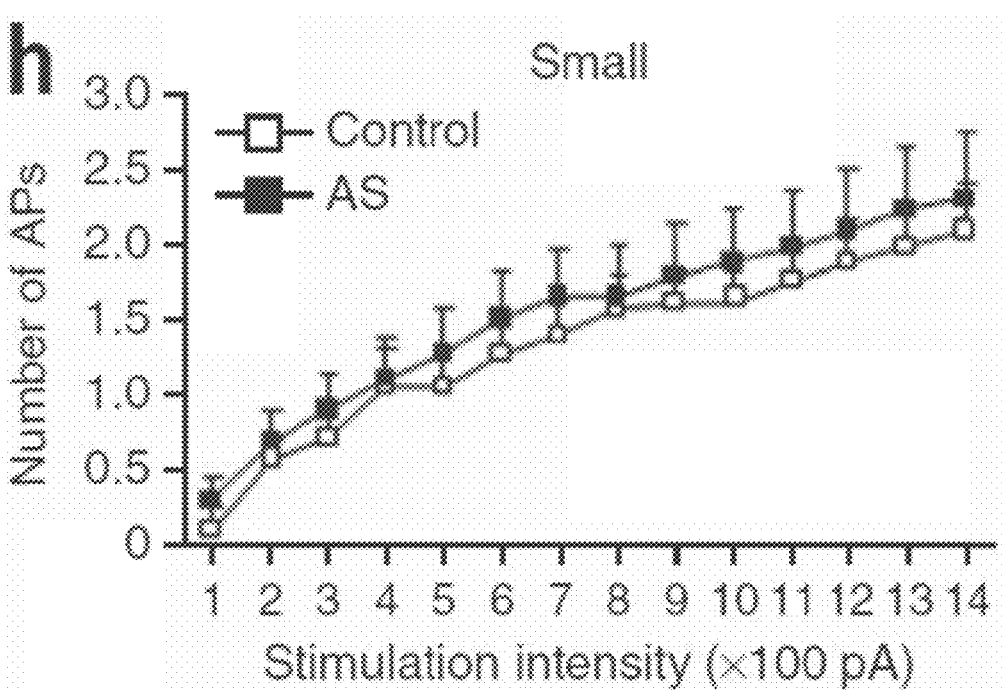
Figure 7I:
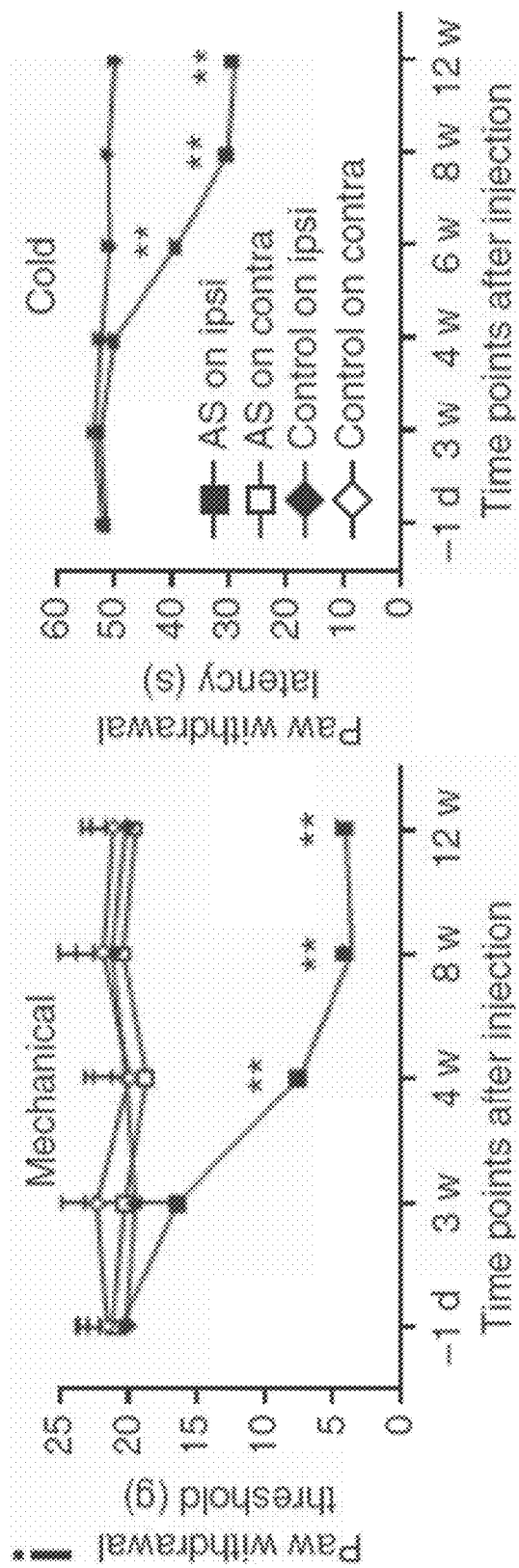
Figure 8A:
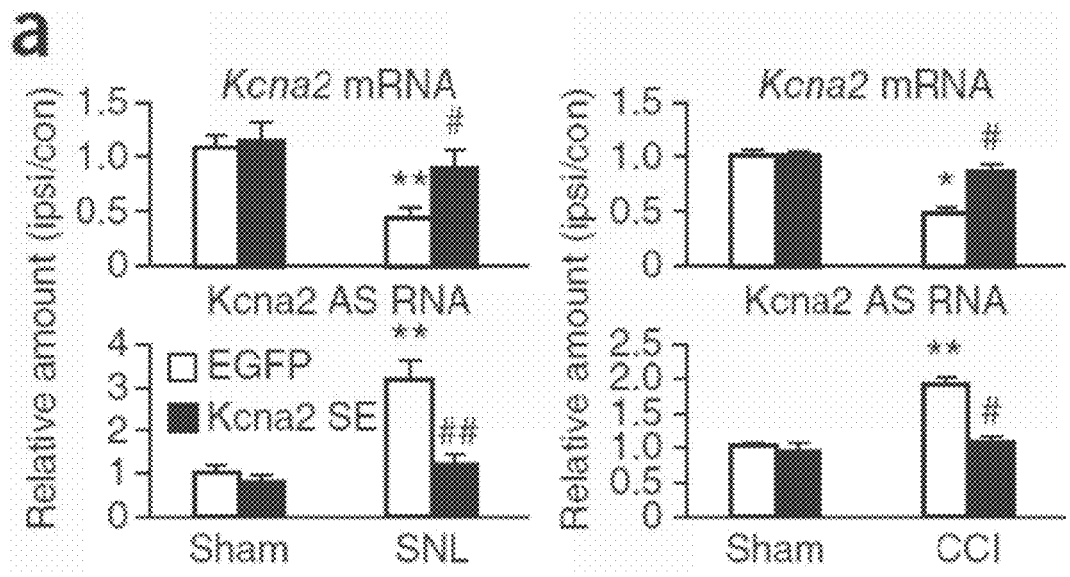
Figure 8B:
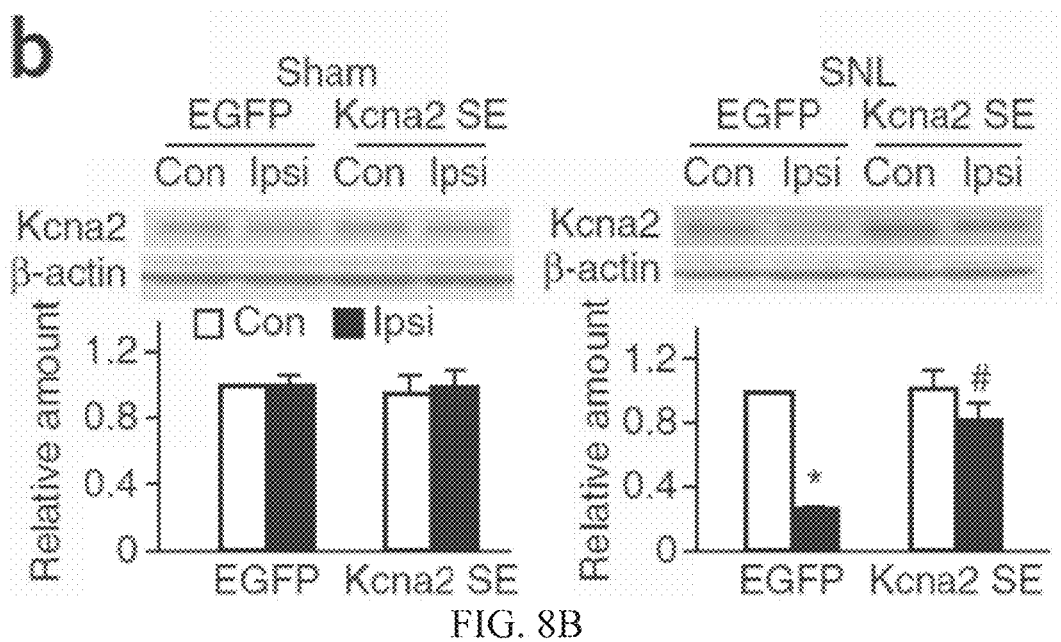

FIG. 8 Blocking nerve injury-induced upregulation of DRG Kcna2 antisense RNA attenuates neuropathic pain. (a) Kcna2 mRNA and Kcna2 antisense (AS) RNA expression in the ipsilateral (Ipsi) and contralateral (Con) L5 DRGs on day 14 after SNL (F=41.03 for AS RNA and 10.26 for mRNA), CCI (F=35.91 for AS RNA and 8.73 for mRNA) or sham surgery in the EGFP-treated and Kcna2 sense fragment (Kcna2 SE)-treated groups. n=12 rats per group. **P<0.01 versus the EGFP-treated group after sham surgery. #P<0.05, ##P<0.01 versus the corresponding EGFP-treated group after SNL or CCI. Two-way ANOVA with Tukey post-hoc test. (b) Kcna2 protein expression in the ipsilateral and contralateral L5 DRGs on day 14 after sham surgery or SNL in the EGFP-treated and Kcna2 SE-treated groups. n=8 rats per group. F=9.26 in SNL and 0.53 in sham-operated. *P<0.05 versus corresponding contralateral side of the EGFP-treated group. #P<0.05 versus the corresponding ipsilateral side of the EGFP-treated group. Two-way ANOVA with Tukey post-hoc test. Full-length blots are presented in Supplementary FIG. 7. (c,d) Effect of Kcna2 SE on the development of SNL- or CCI-induced pain hypersensitivities. Paw withdrawal responses at the times shown before and after SNL (F=23.25 for mechanical, 545.13 for cold and 15.31 for thermal) or CCI (F=22.51 for mechanical, 267.42 for cold and 12.45 for thermal). n=8 rats per group. *P<0.05, **P<0.01 versus the ipsilateral side of the EGFP-treated group at the corresponding time point. Two-way ANOVA with Tukey post-hoc test. (e) Effect of Kcna2 SE on the maintenance of SNL-induced pain hypersensitivities. Paw withdrawal responses at the times shown before and after SNL (F=22.66 for mechanical, 104.16 for cold and 7.64 for thermal). n=8 rats per group. *P<0.05, **P<0.01 versus the ipsilateral side of the EGFP-treated group at the corresponding time point. Two-way ANOVA with Tukey post-hoc test. Error bars, s.e.m.

FIG. 9: (a) Reverse transcription-PCR analysis showing the expression of Kcna2 antisense (AS) RNA in different tissues from normal rats. Lane 1: dorsal root ganglion. Lane 2: spinal cord. Lane 3: brainstem. Lane 4: hippocampus. Lane 5: cerebellum. Lane 6: cortex. Lane 7: heart. Lane 8: liver. Lane 9: lung. Lane 10: kidney. Lane 11: no-template control. Glyceraldehyde 3-phosphate dehydrogenase (Gapdh) was used as an internal control. n=3 repeated experiments. M: a DNA ladder marker. (b) The full-length rat Kcna2 AS cDNA sequence (2.52 kb). It contains a unique sequence at each end (black letters) and complementary sequence in the middle. The pink letters indicate sequences that are complementary to the 3' UTR and part of the 5' UTR of Kcna2 cDNA, and the blue letters indicate the sequence complementary to the coding sequence of Kcna2 cDNA. Translation analysis with DNAMAN software shows more than 30 stop codons distributed throughout the sequence of Kcna2 AS cDNA.

FIG. 10: (a) Western blot analysis revealed the expression of Kcna2 protein in the ipsilateral (Ipsi) and contralateral (Con) L4 DRGs on days 3, 7, and 14 after L5 SNL or sham surgery. n=12 rats/group/time point. F=0.51 for day 3, 0.71 for day 7, and 0.59 for day 14. (b) Quantitative real-time RT-PCR analysis showing the levels of Kcna2 mRNA and Kcna2 AS RNA in the ipsilateral and contralateral L5 dorsal horns on days 3, 7, and 14 after L5 SNL or sham surgery. n=12 rats/group. F=0.82 for mRNA and 0.79 for AS RNA. (c) Western blot analysis showing the expression of Kcna2 protein in the ipsilateral and contralateral L5 dorsal horns on days 3, 7, and 14 after L5 SNL or sham surgery. n=12 rats/group/time point. F=0.58 for day 3, 0.47 for day 7, 0.69 for day 14. (d) Western blot analysis shows a significant reduction in expression of Kcna2 protein in the ipsilateral L4/5 DRGs on day 7 after sciatic nerve axotomy. n=12 rats/group. F=9.68. *P<0.05 vs the contralateral side from the sham group.

FIG. 11: (a) Co-expression of Kcna2 AS RNA with Mzf1 mRNA in small, medium, and large individual DRG neurons. Without RT primers, neither Kcna2 AS nor Mzf1 PCR products were detected in the DNase I-treated samples. n=5 repeats/cell. M: 100-bp ladder. (b) Expression of Mzf1 mRNA in HEK293T cells transfected with control EGFP vector or the full-length Mzf1 vector. Gapdh was used as a loading control. n=3 repeated experiments/treatment. t=−9.25. P<0.01 vs the EGFP group. M: DNA ladder. C: no-template control. (c) Expression of Mzf1 protein in naive HEK293T cell and HEK293T cells transfected with EGFP vector or the full-length Mzf1 vector. H3 was used as a loading control. n=3 repeated experiments/treatment. F=20.87. P<0.01 vs naïve group. (c) Mzf1 siRNA [but not scramble Mzf1 siRNA (Scram)] significantly knocks down Mzf1 protein expression but does not affect expression of nuclear protein H3 or cytosolic proteins mTOR, PKCα, and β-actin in HEK-293T cells.

Figures 12A, 12B, 12C, 12D, 12E, 12F:
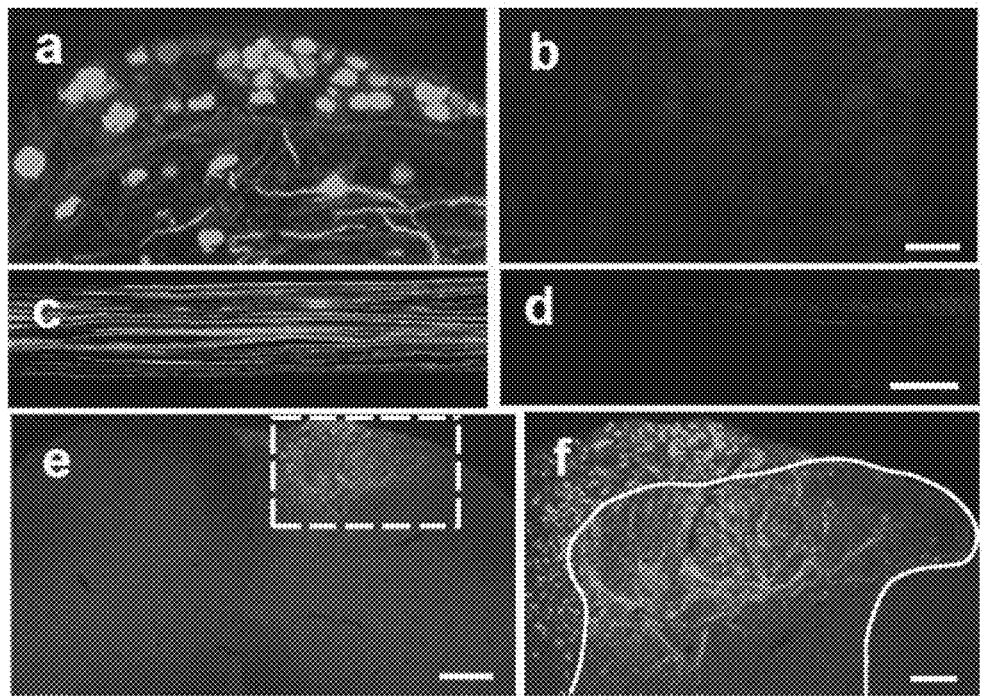
Figure 12G:
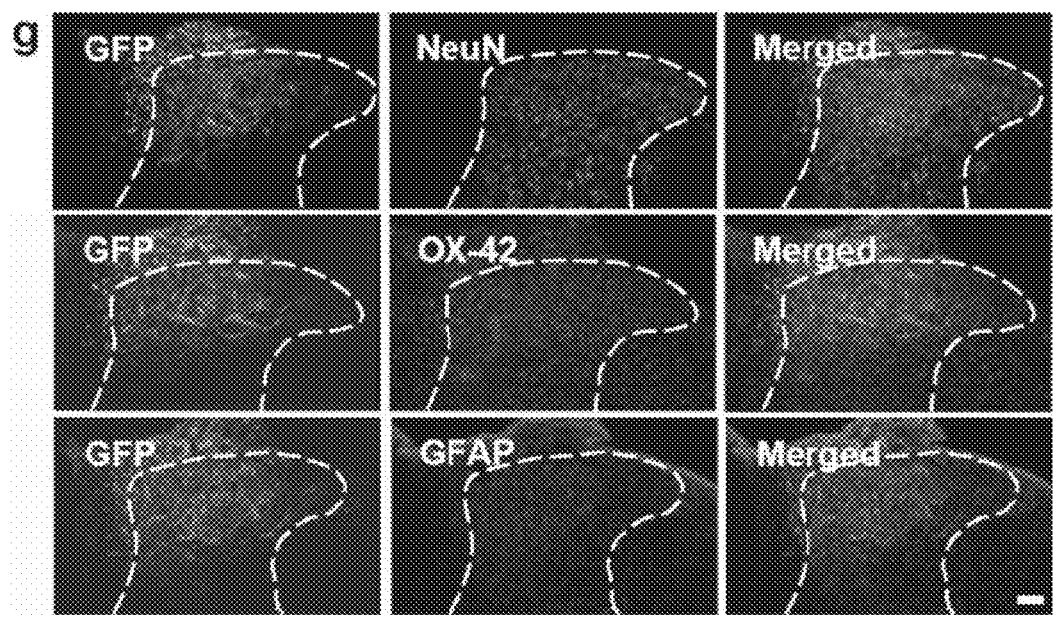
Figure 12H:
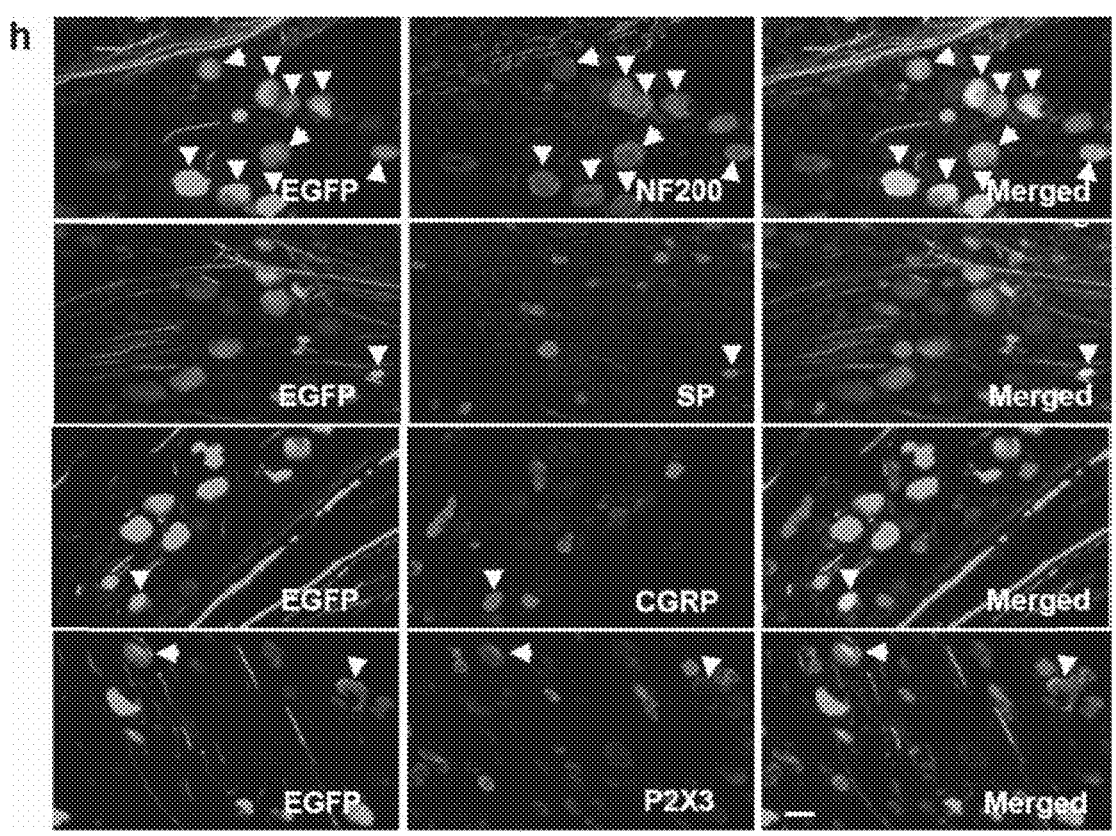

FIG. 12. (a) Ipsilateral L5 DRG. Approximately 60% (±1.8%) of L5 DRG neurons were labeled. (b) Contralateral L5 DRG. (c) Ipsilateral sciatic nerve. (d) Contralateral sciatic nerve. (e) L5 spinal cord dorsal horn. (f) High magnification of the outlined region from e. EGFP fluorescence was detected in many nerve fibers and terminals innervating the dorsal horn ipsilateral to the injection. No cell bodies of spinal cord neurons were labeled. (g) AAV5 does not cross central synapses. EGFP fluorescence did not co-localize with NeuN (a neuronal nuclear marker), OX-42 (a microglial marker), or GFAP (an astrocyte marker) in L5 dorsal horn on the ipsilateral side. (h) Co-localization of EGFP expression with NF200, SP, CGRP, and P2X3 (arrows) in the L5 DRG. n=4-5 rats. Scale bars: 100 μm in a, b, c, d, and e; 50 μm in f; 200 μm in g; 40 μm in h.

Figures 13A, 13B, 13C:
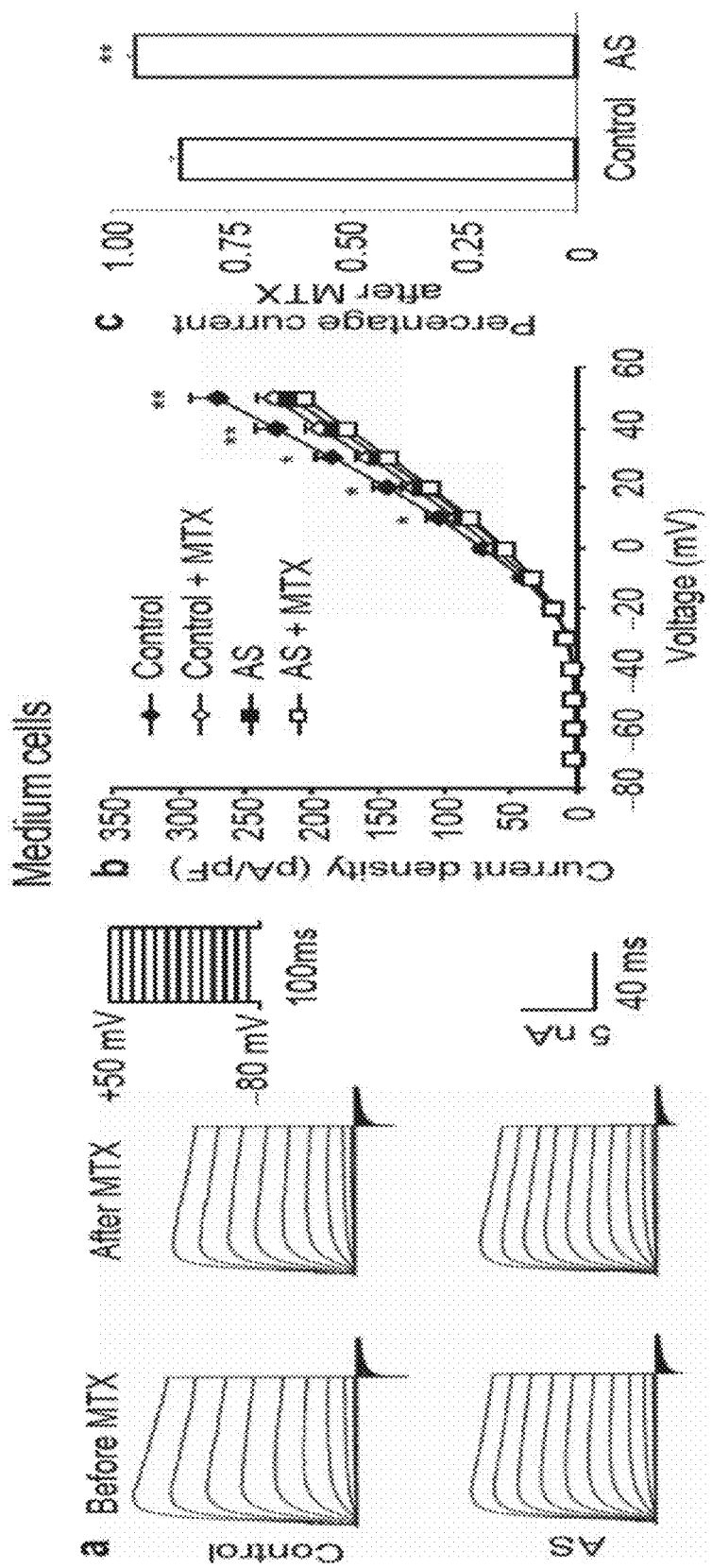

FIG. 13: (a) Representative traces of total Kv current in medium DRG neurons from control and AS-injected rats before or after bath perfusion of 100 nM MTX (b) I-V curve for control (n=17 cells, 7 rats) and AS-treated (n=15 cells, 8 rats) medium DRG neurons before or after 100 nM MTX treatment. The current density was plotted against each voltage. F=117.99, *P<0.05, P<0.01 vs the AS group. (c) At +50 mV, reduction in total Kv current after MTX treatment in medium DRG neurons was greater in the control group (n=17 cells, 7 rats) than in the AS-treated group (n=15 cells, 8 rats). t=−6.54, P<0.01 vs control. (d) Representative traces of total Kv current in small DRG neurons from control and AS-treated rats before or after bath perfusion of 100 nM MTX. (e) I-V curve for control and AS-treated small DRG neurons before or after 100 nM MTX treatment. The current density was plotted against each voltage. n=11 cells/group. (f) At +50 mV, reduction in total Kv current after MTX treatment in small DRG neurons was greater in the control group (n=11 cells, 7 rats) than in the AS-treated group (n=11 cells, 8 rats). t=−2.83, *P<0.05 vs control.

FIG. 14: DRG neurons were recorded before and 3-5 min after bath perfusion of 100 nM maurotoxin (MTX). n=30 large cells, 38 medium cells, and 35 small cells from 7 naïve rats. (a) Resting membrane potentials (RMP) before and after bath perfusion of MTX. t=−2.17 for large cells, −4.59 for medium cells, and −1.03 for small cells. *P<0.05, P<0.01 vs the corresponding cells before MTX treatment. (b) Current threshold for pulses (Ithreshold) before and after bath perfusion of MTX. t=4.60 for large cells, 7.25 for medium cells, and 0.77 for small cells. P<0.01 vs the corresponding cells before MTX treatment. (c, d, e) Numbers of evoked action potentials (APs) produced in large (F=15.45), medium (F=17.18), and small (F=0.78) DRG neurons before or after bath perfusion of MTX. *P<0.05 vs the same stimulation intensity before MTX treatment.

FIG. 15: (a) The amplification reactions of Kcna2 mRNA and three reference genes, Gapdh mRNA, hypoxanthine phosphoribosyltransferase 1 (HPRT1) mRNA, and mitogen-activated protein kinase 6 (MAPK6) mRNA have similar PCR efficiency. The ΔCT (CT Kcan2-CT reference) values are plotted vs log nputs (RNAs, 1-100 ng). The absolute values of the three slopes of ΔCT vs log inputs were less than 0.1, indicating that the efficiency of four mRNA amplifications are approximately equal. (b) Quantitative real-time RT-PCR showed no difference in expression of Gapdh mRNA in the injured L5 DRG on days 0 (naïve), 3, 7, or 14 after SNL. n=6 rats/time point. F=2.17 (P=0.19). (c) Quantitative real-time RT-PCR showed no difference in expression of Gapdh mRNA in the ipsilateral and contralateral L5 DRGs on day 7 after SNL. n=6 rats. t=−1.63 (P=0.12). (d) Quantitative real-time RT-PCR showed no difference in expression of Gapdh mRNA in the injured L5 DRG on days 0 (naïve), 3, 7, or 14 after SNL, as evidenced by no significant alteration in ratios of ipsilateral-side mRNA level to contralateral-side mRNA level after normalization to either HPRT1 or MAPK6. n=6 rats/time point. F=1.45 (P=0.29) for HPRT1 and 3.45 (P=0.071) for MAPK6.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs) and unlocked nucleic acids (DNAs; see, e.g., Jensen et al. Nucleic Acids Symposium Series 52: 133-4), and derivatives thereof.

As used herein, "nucleotide" is used as recognized in the art to include those with natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety (also referred to interchangeably as nucleotide analogs, modified nucleotides, non-natural nucleotides, non-standard nucleotides and other; see, e.g., Usman and McSwiggen; Eckstein, et al., International PCT Publication No. WO 92/07065; Usman et al, International PCT Publication No. WO 93/15187; Uhlman & Peyman, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include, hypoxanthine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman). In particular embodiments, "modified bases" refers to nucleotide bases other than adenine, guanine, cytosine and uracil at 1' position or their equivalents.

As used herein, "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-methoxyethoxy, 2'-fluoro, 2'-allyl, 2'-O-[2-(methylamino)-2-oxoethyl], 4'-thio, 4'-CH$_2$—O-2'-bridge, 4'-(CH$_2$)$_2$—O-2'-bridge, 2'-LNA or other bicyclic or "bridged" nucleoside analog, and 2'-O—(N-methylcarbamate) or those comprising base analogs. In connection with 2'-modified nucleotides as described for the present disclosure, by "amino" is meant 2'-NH$_2$ or 2'-O—NH$_2$, which can be modified or unmodified. Such modified groups are described, e.g., in Eckstein et al., U.S. Pat. No. 5,672,695 and Matulic-Adamic et al., U.S. Pat. No. 6,248,878. "Modified nucleotides" of the instant invention can also include nucleotide analogs as described above.

As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide. As used herein, the term "ribonucleotide" specifically excludes a deoxyribonucleotide, which is a nucleotide possessing a single proton group at the 2' ribose ring position.

As used herein, the term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide.

In reference to the nucleic acid molecules of the present disclosure, modifications may exist upon these agents in patterns. As used herein, "alternating positions" refers to a pattern where every other nucleotide is a modified nucleotide or there is an unmodified nucleotide (e.g., an unmodified ribonucleotide) between every modified nucleotide over a defined length of a strand (e.g., 5'-MNMNMN-3'; 3'-MNMNMN-5'; where M is a modified nucleotide and N is an unmodified nucleotide). In such embodiments, the modification pattern starts from the first nucleotide position at either the 5' or 3' terminus according to a position numbering convention. The pattern of modified nucleotides at alternating positions may run the full length of the strand, but in certain embodiments includes at least 4, 6, 8, 10, 12, 14 nucleotides containing at least 2, 3, 4, 5, 6 or 7 modified nucleotides, respectively. As used herein, "alternating pairs of positions" refers to a pattern where two consecutive modified nucleotides are separated by two consecutive unmodified nucleotides over a defined length of a strand (e.g., 5'-MMNNMMNNMMNN-3'; 3'-MMNNMMNNM-MNN-5'; where M is a modified nucleotide and N is an unmodified nucleotide). The modification pattern starts from the first nucleotide position at either the 5' or 3' terminus according to a position numbering convention such as those described herein. The pattern of modified nucleotides at alternating positions may run the full length of the strand, but preferably includes at least 8, 12, 16, 20, 24, 28 nucleotides containing at least 4, 6, 8, 10, 12 or 14 modified nucleotides, respectively. It is emphasized that the above modification patterns are exemplary and are not intended as limitations on the scope of the invention.

As used herein, "base analog" refers to a heterocyclic moiety which is located at the 1' position of a nucleotide sugar moiety in a modified nucleotide. A base analog is generally either a purine or pyrimidine base excluding the common bases guanine (G), cytosine (C), adenine (A), thymine (T), and uracil (U). Base analogs include those useful in the compounds and methods of the invention, e.g., those disclosed in U.S. Pat. Nos. 5,432,272 and 6,001,983 to Benner and U.S. Patent Publication No. 20080213891 to Manoharan, which are herein incorporated by reference. Non-limiting examples of bases include hypoxanthine (I), xanthine (X), 3β-D-ribofuranosyl-(2,6-diaminopyrimidine) (K), 3-β-D-ribofuranosyl-(1-methyl-pyrazolo[4,3-d]pyrimidine-5,7(4H,6H)-dione) (P), iso-cytosine (iso-C), iso-guanine (iso-G), 1-β-D-ribofuranosyl-(5-nitroindole), 1-β-D-ribofuranosyl-(3-nitropyrrole), 5-bromouracil, 2-aminopurine, 4-thio-dT, 7-(2-thienyl)-imidazo[4,5-b]pyridine (Ds) and pyrrole-2-carbaldehyde (Pa), 2-amino-6-(2-thienyl)purine (S), 2-oxopyridine (Y), difluorotolyl, 4-fluoro-6-methylbenzimidazole, 4-methylbenzimidazole, 3-methyl isocarbostyrilyl, 5-methyl isocarbostyrilyl, and 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenzyl, tetracenyl, pentacenyl, and structural derivates thereof (Schweitzer et al., J. Org. Chem., 59:7238-7242 (1994); Berger et al., Nucleic Acids Research, 28(15):2911-2914 (2000); Moran et al., J. Am. Chem. Soc., 119:2056-2057 (1997); Morales et al., J. Am. Chem. Soc., 121:2323-2324 (1999); Guckian et al., J. Am. Chem. Soc., 118:8182-8183 (1996); Morales et al., J. Am. Chem. Soc., 122(6):1001-

1007 (2000); McMinn et al., J. Am. Chem. Soc., 121:11585-11586 (1999); Guckian et al., J. Org. Chem., 63:9652-9656 (1998); Moran et al., Proc. Natl. Acad. Sci., 94:10506-10511 (1997); Das et al., J. Chem. Soc., Perkin Trans., 1:197-206 (2002); Shibata et al., J. Chem. Soc., Perkin Trans., 1: 1605-1611 (2001); Wu et al., J. Am. Chem. Soc., 122(32): 7621-7632 (2000); O'Neill et al., J. Org. Chem., 67:5869-5875 (2002); Chaudhuri et al., J. Am. Chem. Soc., 117: 10434-10442 (1995); and U.S. Pat. No. 6,218,108.). Base analogs may also be a universal base.

As used herein, "universal base" refers to a heterocyclic moiety located at the 1' position of a nucleotide sugar moiety in a modified nucleotide, or the equivalent position in a nucleotide sugar moiety substitution, that, when present in a nucleic acid duplex, can be positioned opposite more than one type of base without altering the double helical structure (e.g., the structure of the phosphate backbone). Additionally, the universal base does not destroy the ability of the single stranded nucleic acid in which it resides to duplex to a target nucleic acid. The ability of a single stranded nucleic acid containing a universal base to duplex a target nucleic can be assayed by methods apparent to one in the art (e.g., UV absorbance, circular dichroism, gel shift, single stranded nuclease sensitivity, etc.). Additionally, conditions under which duplex formation is observed may be varied to determine duplex stability or formation, e.g., temperature, as melting temperature (Tm) correlates with the stability of nucleic acid duplexes. Compared to a reference single stranded nucleic acid that is exactly complementary to a target nucleic acid, the single stranded nucleic acid containing a universal base forms a duplex with the target nucleic acid that has a lower Tm than a duplex formed with the complementary nucleic acid. However, compared to a reference single stranded nucleic acid in which the universal base has been replaced with a base to generate a single mismatch, the single stranded nucleic acid containing the universal base forms a duplex with the target nucleic acid that has a higher Tm than a duplex formed with the nucleic acid having the mismatched base.

Some universal bases are capable of base pairing by forming hydrogen bonds between the universal base and all of the bases guanine (G), cytosine (C), adenine (A), thymine (T), and uracil (U) under base pair forming conditions. A universal base is not a base that forms a base pair with only one single complementary base. In a duplex, a universal base may form no hydrogen bonds, one hydrogen bond, or more than one hydrogen bond with each of G, C, A, T, and U opposite to it on the opposite strand of a duplex. In one embodiment, the universal base does not interact with the base opposite to it on the opposite strand of a duplex. In a duplex, base pairing between a universal base occurs without altering the double helical structure of the phosphate backbone. A universal base may also interact with bases in adjacent nucleotides on the same nucleic acid strand by stacking interactions. Such stacking interactions stabilize the duplex, especially in situations where the universal base does not form any hydrogen bonds with the base positioned opposite to it on the opposite strand of the duplex. Non-limiting examples of universal-binding nucleotides include inosine, 1-β-D-ribofuranosyl-5-nitroindole, and/or 143-D-ribofuranosyl-3-nitropyrrole (U.S. patent application Publication No. 20070254362 to Quay et al.; Van Aerschot et al., An acyclic 5-nitroindazole nucleoside analogue as ambiguous nucleoside. Nucleic Acids Res. 1995 Nov. 11; 23(21): 4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as a universal base analogue. Nucleic Acids Res. 1994 October.

Where a first sequence is referred to as "substantially complementary" with respect to a second sequence herein, the two sequences can be fully complementary, or they may form one or more mismatched base pairs upon hybridization, while retaining the ability to hybridize under the conditions most relevant to their ultimate application.

The phrase "duplex region" refers to the region in two complementary or substantially complementary oligonucleotides that form base pairs with one another, either by Watson-Crick base pairing or other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well-known in the art. Alternatively, two strands can be synthesized and added together under biological conditions to determine if they anneal to one another.

Single-stranded nucleic acids that base pair over a number of bases are said to "hybridize." Hybridization is typically determined under physiological or biologically relevant conditions (e.g., intracellular: pH 7.2, 140 mM potassium ion; extracellular pH 7.4, 145 mM sodium ion). Hybridization conditions generally contain a monovalent cation and biologically acceptable buffer and may or may not contain a divalent cation, complex anions, e.g., gluconate from potassium gluconate, uncharged species such as sucrose, and inert polymers to reduce the activity of water in the sample, e.g. PEG. Such conditions include conditions under which base pairs can form.

Hybridization is measured by the temperature required to dissociate single stranded nucleic acids forming a duplex, i.e., (the melting temperature; Tm). Hybridization conditions are also conditions under which base pairs can form. Various conditions of stringency can be used to determine hybridization (see, e.g., Wahl, G. M. and S. L. Berger (1987 Methods Enzymol. 152:399; Kimmel, A. R. (1987) Methods Enzymol. 152:507). Stringent temperature conditions will ordinarily include temperatures of at least about 30° C., at least about 37° C., or at least about 42° C.

Useful variations on hybridization conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Antisense to Molecular Cloning Techniques, 1987, Academic Press, New York); and Sambrook et al., Molecular Cloning: A Laboratory Manual, Cold Spring Harbor Laboratory Press, New York.

As used herein, "oligonucleotide strand" is a single stranded nucleic acid molecule. An oligonucleotide may comprise ribonucleotides, deoxyribonucleotides, modified nucleotides (e.g., nucleotides with 2' modifications, synthetic base analogs, etc.) or combinations thereof. Such modified oligonucleotides can be preferred over native forms because of properties such as, for example, enhanced cellular uptake and increased stability in the presence of nucleases.

As used herein, "overhang" refers to unpaired nucleotides, in the context of a duplex having one or more free ends at the 5' terminus or 3' terminus of a double stranded nucleic acid molecule. In certain embodiments, the overhang is a 3' or 5' overhang on the antisense strand or sense strand. In some embodiments, the overhang is a 3' overhang having a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides. "Blunt" or "blunt end" means that there are no unpaired nucleotides at that end of the double stranded nucleic acid molecule, i.e., no nucleotide overhang.

By "homologous sequence" is meant, a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include conserved sequence regions shared by more than one polynucleotide sequence. Homology does not need to be perfect homology (e.g., 100%), as partially homologous sequences are also contemplated by the instant invention (e.g., 99%, 98%, 97%, 96%, 95%, 94%, 93%, 92%, 91%, 90%, 89%, 88%, 87%, 86%, 85%, 84%, 83%, 82%, 81%, 80% etc.). Indeed, design and use of the Kcna2 sense fragment molecules of the instant invention contemplates the possibility of using such molecules not only against target long non-coding Kcna2 RNAs possessing perfect complementarity with the presently Kcna2 sense fragment molecules, but also against target long non-coding Kcna2 RNAs possessing sequences that are, e.g., only 99%, 98%, 97%, 96%, 95%, 94%, 93%, 92%, 91%, 90%, 89%, 88%, 87%, 86%, 85%, 84%, 83%, 82%, 81%, 80% etc. complementary to the Kcna2 sense fragment molecules. Similarly, it is contemplated that the presently described Kcna2 sense fragment molecules of the instant invention might be readily altered by the skilled artisan to enhance the extent of complementarity between Kcna2 sense fragment molecules and a target long non-coding Kcna2 RNA. Indeed, Kcna2 sense fragment sequences with insertions, deletions, and single point mutations relative to the target long non-coding Kcna2 RNA sequence can also be effective for inhibition. Alternatively, Kcna2 sense fragment sequences with nucleotide analog substitutions or insertions can be effective for inhibition.

Sequence identity may be determined by sequence comparison and alignment algorithms known in the art. To determine the percent identity of two nucleic acid sequences, the sequences are aligned for comparison purposes (e.g., gaps can be introduced in the first sequence or second sequence for optimal alignment). The nucleotides at corresponding nucleotide positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions× 100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, a gapped alignment is formed by introducing appropriate gaps, and percent identity is determined over the length of the aligned sequences. To obtain gapped alignments for comparison purposes, Gapped BLAST can be utilized as described in Altschul et al., (1997) Nucleic Acids Res. 25(17):3389-3402. In another embodiment, a global alignment is formed by introducing appropriate gaps, and percent identity is determined over the entire length of the sequences aligned. A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the Kcna2 sense fragment molecules and long non-coding Kcna2 RNA is preferred. Alternatively, the Kcna2 sense fragment molecules may be defined functionally as a nucleotide sequence that is capable of hybridizing with a portion of the long non-coding Kcna2 RNA (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4.

By "conserved sequence region" is meant, a nucleotide sequence of one or more regions in a polynucleotide does not vary significantly between generations or from one biological system, subject, or organism to another biological system, subject, or organism. The polynucleotide can include both coding and non-coding DNA and RNA.

By "sense region" is meant a nucleotide sequence of a dsRNA molecule having complementarity to an antisense region of the dsRNA molecule. In addition, the sense region of a dsRNA molecule can comprise a nucleic acid sequence having homology with a target nucleic acid sequence.

By "antisense region" is meant a nucleotide sequence of a dsRNA molecule having complementarity to a target nucleic acid sequence. In addition, the antisense region of a dsRNA molecule comprises a nucleic acid sequence having complementarity to a sense region of the dsRNA molecule.

As used herein, "antisense strand" refers to a single stranded nucleic acid molecule which has a sequence complementary to that of a target RNA. As used herein, "sense strand" refers to a single stranded nucleic acid molecule which has a sequence complementary to that of an antisense strand. When the sense strand contains modified nucleotides with base analogs, the sense strand need not be complementary over the entire length of the sense strand, but must at least duplex with the antisense strand.

By "target nucleic acid" is meant a nucleic acid sequence whose expression, level or activity is to be modulated. The target nucleic acid can be DNA or RNA. For agents that target long non-coding Kcna2 DNA, in certain embodiments, the target nucleic acid is long non-coding Kcna2 RNA, which is also referred to herein as antisense Kcna2 RNA. Long non-coding Kcna2 RNA target sites can also interchangeably be referenced by corresponding cDNA sequences.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence.

By "RNA" is meant a molecule comprising at least one ribonucleotide residue. The at RNA residues may be contiguous. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the dsRNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "subject" is meant an organism, which is a donor or recipient of explanted cells or the cells themselves. "Subject" also refers to an organism to which the Kcna2 sense fragment molecule can be administered. A subject can be a mammal or mammalian cells, including a human or human cells.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed Kcna2 sense fragment compositions may be micellar structures, such as a liposomes, capsids, capsoids, polymeric nanocapsules, or polymeric microcapsules.

Polymeric nanocapsules or microcapsules facilitate transport and release of the encapsulated or bound Kcna2 sense fragment compositions into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

"Treatment", or "treating" as used herein, is defined as the application or administration of a therapeutic agent (e.g., a Kcna2 sense fragment molecule or a vector or transgene encoding same) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment.

The term "consisting essentially of as used herein in connection with a nucleic acid, protein or vector (e.g., adeno-associated virus (AAV) means that the nucleic acid, protein or vector does not contain any element other than the recited element(s) that significantly alters (e.g., more than about 1%, 5% or 10%) the function of interest of the nucleic acid, protein or vector.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See. e.g., BERNARD N. FIELDS et al. VIROLOGY, volume 2, chapter 69 (4th ed., Lippincott-Raven Publishers). A number of additional AAV serotypes and clades have been identified (see, e.g., Gao et al, (2004) J. Virol. 78:6381-6388 and Table 1), which are also encompassed by the term "AAV."

The genomic sequences of various AAV and autonomous parvoviruses, as well as the sequences of the ITRs, Rep proteins, and capsid subunits are known in the art. Such sequences may be found in the literature or in public databases such as the GenBank® database. See, e.g., GenBank® Accession Numbers NC 002077, NC 001401, NC 001729, NC 001863, NC 001829, NC 001862, NC 000883, NC 001701, NC 001510, AF063497, U89790, AF043303, AF028705, AF028704, J02275, J01901, J02275, X01457, AF288061, AH009962, AY028226, AY028223, NC 001358, NC 001540, AF513851, AF513852, AY530579, AY631965, AY631966; the disclosures of which are incorporated herein in their entirety. See also, e.g., Srivistava et al., (1983) J Virol. 45:555; Chiorini et al., (1998) J Virol. 71:6823; Chiorini et al., (1999) J Virol. 73:1309; Bantel-Schaal et al, (1999) J Virol. 73:939; Xiao et al, (1999) J Virol. 73:3994; Muramatsu et al, (1996) Virology 221:208; Shade et al, (1986) J Virol. 58:921; Gao et al, (2002) Proc. Nat. Acad. Sci. USA 99:11854; international patent publications WO 00/28061, WO 99/61601, WO 98/11244; U.S. Pat. No. 6,156,303; the disclosures of which are incorporated herein in their entirety.

A "chimeric" AAV nucleic acid capsid coding sequence or AAV capsid protein is one that combines portions of two or more capsid sequences. A "chimeric" AAV virion or particle comprises a chimeric AAV capsid protein.

As used herein, an "isolated" nucleic acid or nucleotide sequence (e.g., an "isolated DNA" or an "'isolated RNA") means a nucleic acid or nucleotide sequence separated or substantially free from at least some of the other components of the naturally occurring organism, for example, the cell or structural components or other polypeptides or nucleic acids commonly found associated with the nucleic acid or nucleotide sequence.

As used herein, the term "virus vector," "viral vector" (and similar terms) generally refers to a virus particle that functions as a nucleic acid delivery vehicle, and which comprises the viral nucleic acid (i.e., the vector genome) packaged within the virion. Virus vectors according to the present invention comprise a chimeric AAV capsid according to the invention and can package an AAV or rAAV genome or any other nucleic acid including viral nucleic acids. Alternatively, in some contexts, the term "virus vector," "viral vector" (and similar terms) may be used to refer to the vector genome (e.g., vDNA) in the absence of the virion and/or to a viral capsid that acts as a transporter to deliver molecules tethered to the capsid or packaged within the capsid.

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) Curr. Topics Microbiol. Immunol. 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3 ' or 5' end.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745.

An "AAV terminal repeat" or "AAV TR" may be from any AAV, including but not limited to serotypes 1, 2, 3, 4, 5, 6, 7, 8, 9, 10 or 11 or any other AAV now known or later discovered. An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The terms "rAAV particle" and "rAAV virion" are used interchangeably here. A "rAAV particle" or "rAAV virion" comprises a rAAV vector genome packaged within an AAV capsid.

Recent studies suggest that the mechanism for gene regulation involves widespread noncoding RNAs, including lncRNAs. The study of lncRNAs is still in its infancy. A few lncRNAs have been identified in mammalian cells and implicated in gene-regulatory roles such as transcription and translation. Their expression is associated with some physiological and pathological processes, but how they are causally linked to disease development is elusive. Here, we report a new native lncRNA that is expressed in mammalian DRG neurons. Because most of its sequence is complementary to Kcna2 RNA, we named it Kcna2 antisense RNA. We found that Kcna2 antisense RNA may act as a biologically active regulator and participate in induction and maintenance of neuropathic pain by specifically silencing Kcna2 expression in the DRG.

II. Kcna2 Sense Fragments and Long Non-Coding Kcna2 RNA

The present invention features one or more Kcna2 sense fragment molecules that can modulate Kcna2 expression by blocking long non-coding Kcna2 (also referred to as Kcna2 antisense RNA or cDNA) (and thereby blocking downregulation of Kcna2 expression). The below description of the various aspects and embodiments of the invention is provided with reference to exemplary Kcna2 sense fragment molecules. However, such reference is meant to be exemplary only and the various aspects and embodiments of the invention are also directed to alternate Kcna2 sense fragment molecules, such as mutant or variant Kcna2 sense fragment molecules and Kcna2 sense fragment molecules having non-native bases.

The term "Kcna2" refers to nucleic acid sequences encoding a Kcna2 protein, peptide, or polypeptide (e.g., Kcna2 transcripts, such as the sequences of Kcna2 Genbank Accession No. NM_004974.3 (human Kcna2 mRNA (SEQ ID NO:4). In certain embodiments, the term "Kcna2" is also meant to include other Kcna2 encoding sequence, such as other Kcna2 isoforms, mutant Kcna2 genes, splice variants of Kcna2 genes, and Kcna2 gene polymorphisms.

In particular embodiments, a Kcna2 sense fragment molecule comprises about 10 to about 1000 (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000) nucleotides that are complementary to one or more target long non-coding Kcna2 nucleic acid molecules or a portion thereof.

In particular embodiments, the Kcna2 sense fragment molecule of the present invention comprises a fragment of SEQ ID NO:4, Human Kcna2 mRNA 5'3': 5'UTR (1-621); CDS (622-2121); 3' UTR (2122-2267). The fragment can comprise a portion of the 5' untranslated region, the coding sequence or the 3' untranslated region. The fragment can comprise both a portion of the 5' UTR and the CDS. In another embodiment, the fragment can comprise a portion of the CDS and the 3' UTR.

In other embodiments, the fragment can comprise any segment of −400 to −1 of the 5'UTR including, but not limited to, a fragment beginning at −400, −399, −398, −397, −396, −395, −394, −393, −392, −391, −390, −389, −388, −387, −386, −385, −384, −383, −382, −381, −380, −379, −378, −377, −376, −375, −374, −373, −372, −371, −370, −369, −368, −367, −366, −365, −364, −363, −362, −361, −360, −359, −358, −357, −356, −355, −354, −353, −352, −351, −350, −349, −348, −347, −346, −345, −344, −343, −342, −341, −340, −339, −338, −337, −336, −335, −334, −333, −332, −331, −330, −329, −328, −327, −326, −325, −324, −323, −322, −321, −320, −319, −318, −317, −316, −315, −314, −313, −312, −311, −310, −309, −308, −307, −306, −305, −304, −303, −302, −301, −300, −299, −298, −297, −296, −295, −294, −293, −292, −291, −290, −289, −288, −287, −286, −285, −284, −283, −282, −281, −280, −279, −278, −277, −276, −275, −274, −273, −272, −271, −270, −269, −268, −267, −266, −265, −264, −263, −262, −261, −260, −259, −258, −257, −256, −255, −254, −253, −252, −251, −250, −249, −248, −247, −246, −245, −244, −243, −242, −241, −240, −239, −238, −237, −236, −235, −234, −233, −232, −231, −230, −229, −228, −227, −226, −225, −224, −223, −222, −221, −220, −219, −218, −217, −216, −215, −214, −213, −212, −211, −210, −209, −208, −207, −206, −205, −204, −203, −202, −201, −200, −199, −198, −197, −196, −195, −194, −193, −192, −191, −190, −189, −188, −187, −186, −185, −184, −183, −182, −181, −180, −179, −178, −177, −176, −175, −174, −173, −172, −171, −170, −169, −168, −167, −166, −165, −164, −163, −162, −161, −160, −159, −158, −157, −156, −155, −154, −153, −152, −151, −150, −149, −148, −147, −146, −145, −144, −143, −142, −141, −140, −139, −138, −137, −136, −135, −134, −133, −132, −131, −130, −129, −128, −127, −126, −125, −124, −123, −122, −121, −120, −119, −118, −117, −116, −115, −114, −113, −112, −111, −110, −109, −108, −107, −106, −105, −104, −103, −102, −101, −100, −99, −98, −97, −96, −95, −94, −93, −92, −91, −90, −89, −88, −87, −86, −85, −84, −83, −82, −81, −80, −79, −78, −77, −76, −75, −74, −73, −72, −71, −70, −69, −68, −67, −66, −65, −64, −63, −62, −61, −60, −59, −58, −57, −56, −55, −54, −53, −52, −51, −50, −49, −48, −47, −46, −45, −44, −43, −42, −41, −40, −39, −38, −37, −36, −35, −34, −33, −32, −31, −30, −29, −28, −27, −26, −25, −24, −23, −22, −21, −20, −19, −18, −17, −16, −15, −14, −13, −12, −11, −10, −9, −8, −7, −6, −5, −4, −3, −2, −1, and ending anywhere between +1 to +100 of the CDS including, but not limited to, including +1, +2, +3, +4, +5, +6, +7, +8, +9, +10, +11, +12, +13, +14, +15, +16, +17, +18, +19, +20, +21, +22, +23, +24, +25, +26, +27, +28, +29, +30, +31, +32, +33, +34, +35, +36, +37, +38, +39, +40, +41, +42, +43, +44, +45, +46, +47, +48, +49, +50, +51, +52, +53, +54, +55, +56, +57, +58, +59, +60, +61, +62, +63, +64, +65, +66, +67, +68, +69, +70, +71, +72, +73, +74, +75, +76, +77, +78, +79, +80, +81, +82, +83, +84, +85, +86, +87, +88, +89, +90, +91, +92, +93, +94, +95, +96, +97, +98, +99, +100. Non-limiting examples of the foregoing include fragments such as −400 to +60, −390 to +55, −380 to +50, −370 to +45, −360 to +40, −350 to +40, −340 to +40, −330 to +40, −320 to +40, −310 to +40, −300 to +40, and so forth, where the A in the ATG start codon is +1.

In particular embodiments, the Kcna2 sense fragment is recombinant. The Kcna2 sense fragment may further comprise a linker. The linker may be fused to the sense fragment at the 5' or 3' end. In a particular embodiment, the linker is fused to the sense fragment in order to get it into the delivery vehicle. In other embodiments, the Kcna2 sense fragments comprise one or modified bases. In certain embodiments, the modified bases provide stability to the fragment.

In one embodiment, a Kcna2 sense fragment molecule of the present invention is deemed to possess "long non-coding Kcna2 RNA inhibitory activity" if a statistically significant reduction in long non-coding Kcna2 RNA is seen when a Kcna2 sense fragment molecule is administered to a system (e.g., cell-free in vitro system), cell, tissue or organism, as compared to a selected control. The distribution of experimental values and the number of replicate assays performed will tend to dictate the parameters of what levels of reduction in long non-coding Kcna2 RNA (either as a % or in absolute terms) is deemed statistically significant (as assessed by standard methods of determining statistical significance known in the art). However, in another embodiment, "long non-coding Kcna2 RNA inhibitory activity" is defined based upon a % or absolute level of reduction in the level of long non-coding Kcna2 RNA in a system, cell, tissue or organism. For example, in certain embodiments, a Kcna2 sense fragment molecule is deemed to possess long non-coding Kcna2 RNA inhibitory activity if at least a 5% reduction or at least a 10% reduction in long non-coding Kcna2 RNA is observed in the presence of a Kcna2 sense fragment molecule relative to long non-coding Kcna2 RNA is observed in the presence of a Kcna2 sense fragment molecule relative to Kcna2 levels seen for a suitable control. For example, in vivo long non-coding Kcna2 RNA levels in a tissue and/or subject can, in certain embodiments, be deemed to be inhibited by a Kcna2 sense fragment molecule if, e.g., a 5% or 10% reduction in long non-coding Kcna2 RNA levels is observed relative to a control. In certain other embodiments, a Kcna2 sense fragment molecule of the invention is deemed to possess long non-coding Kcna2 RNA inhibitory activity if long non-coding Kcna2 RNA levels are observed to be reduced by at least 15% relative to a selected control, by at least 20% relative to a selected control, by at least 25% relative to a selected control, by at least 30% relative to a selected control, by at least 35% relative to a selected control, by at least 40% relative to a selected control, by at least 45% relative to a selected control, by at least 50% relative to a selected control, by at least 55% relative to a selected control, by at least 60% relative to a selected control, by at least 65% relative to a selected control, by at least 70% relative to a selected control, by at least 75% relative to a selected control, by at least 80% relative to a selected control, by at least 85% relative to a selected control, by at least 90% relative to a selected control, by at least 95% relative to a selected control, by at least 96% relative to a selected control, by at least 97% relative to a selected control, by at least 98% relative to a selected control or by at least 99% relative to a selected control. In some embodiments, complete inhibition of long non-coding Kcna2 RNA is required for a Kcna2 sense fragment molecule to be deemed to possess long non-coding Kcna2 RNA inhibitory activity. In certain models (e.g., cell culture), a Kcna2 sense fragment molecule is deemed to possess long non-coding Kcna2 RNA inhibitory activity if at least a 50% reduction in long non-coding Kcna2 RNA levels is observed relative to a suitable control. In certain other embodiments, a Kcna2 sense fragment molecule is deemed to possess long non-coding Kcna2 RNA inhibitory activity if at least an 80% reduction in long non-coding Kcna2 RNA levels is observed relative to a suitable control.

Use of other endpoints for determination of whether a Kcna2 sense fragment molecule possesses long non-coding Kcna2 RNA inhibitory activity is also contemplated. Specifically, in one embodiment, expression of Kcna2 is assessed, and a tested Kcna2 sense fragment molecule is deemed to possess long non-coding Kcna2 RNA inhibitory activity if Kcna2 levels mRNA levels are at or near normal levels (e.g., normal expression levels in subjects not experiencing neuropathic pain). The rationale is that the Kcna2 sense fragment molecule blocks the binding of long non-coding Kcan2 RNA to Kcna2 mRNA. Long non-coding Kcna2 RNA inhibitory levels and/or Kcna2 levels may also be assessed indirectly, e.g., measurement of a reduction of neuropathic pain in a subject may be used to assess Kcna2 levels and/or long non-coding Kcna2 RNA inhibitory efficacy of a Kcna2 sense fragment molecule of the instant invention.

As used herein, a Kcna2 sense fragment molecule comprises a sequence "sufficiently complementary" to a target RNA or cDNA sequence (e.g., long non-coding Kcna2 RNA) means that the Kcna2 sense fragment molecule has a sequence sufficient to reduce or block the downregulation of Kcna2 mRNA by long non-coding Kcna2 RNA.

In another embodiment, "sufficiently complementary" refers to a Kcna2 sense fragment molecule having a sequence sufficient to trigger the destruction of the target RNA (where a cDNA sequence is recited, the RNA sequence corresponding to the recited cDNA sequence) by the RNAi machinery or process. For example, a Kcna2 sense fragment molecule that is "sufficiently complementary" to a target RNA or cDNA sequence to trigger the destruction of the target RNA by the RNAi machinery or process can be identified as a Kcna2 sense fragment molecule that causes a detectable reduction in the level of the target long non-coding Kcna2 RNA in an appropriate assay. In other embodiments, a Kcna2 sense fragment molecule that is sufficiently complementary to a target RNA or cDNA sequence to trigger the destruction of the target RNA by the RNAi machinery or process can be identified as a Kcna2 sense fragment molecule that produces at least a 5%, at least a 10%, at least a 15%, at least a 20%, at least a 25%, at least a 30%, at least a 35%, at least a 40%, at least a 45%, at least a 50%, at least a 55%, at least a 60%, at least a 65%, at least a 70%, at least a 75%, at least a 80%, at least a 85%, at least a 90%, at least a 95%, at least a 98% or at least a 99% reduction in the level of the target RNA in an appropriate assay. In additional examples, a Kcna2 sense fragment molecule that is sufficiently complementary to a target RNA or cDNA sequence to trigger the destruction of the target RNA by the RNAi machinery or process can be identified based upon assessment of the duration of a certain level of inhibitory activity with respect to the target RNA or protein levels in a cell or organism.

The Kcna2 sense fragment molecule can be designed such that every residue of the strand is complementary to a residue in the target molecule. Alternatively, substitutions can be made within the molecule to increase stability and/or enhance processing activity of the molecule. Substitutions can be made within the strand or can be made to residues at the ends of the strand. In certain embodiments, substitutions and/or modifications are made at specific residues within Kcna2 sense fragment molecule.

In one embodiment, Kcna2 sense fragment molecules of the invention that block upregulation/increased expression of long non-coding Kcna2 RNA (and thereby reduce or block downregulation of Kcna2 mRNA and protein) are used for treating, preventing or reducing Kcna2-related diseases or disorders (e.g., neuropathic pain) in a subject or organism.

III. Expression and Delivery of Kcna2 Sense Fragments

In certain embodiments, the Kcna2 sense fragment molecules of the invention are added directly, or can be complexed with lipids (e.g., cationic lipids), packaged within liposomes, or otherwise delivered to target cells or tissues. The nucleic acid or nucleic acid complexes can be locally administered to relevant tissues ex vivo or in vivo through oral application, direct dermal application, transdermal application, or injection, with or without their incorporation in biopolymers.

In other embodiments, a vector comprises the Kcna2 sense fragment molecules of the present invention. In particular embodiments, an adeno-associated vector comprises the Kcna2 sense fragment molecules.

The invention relates to preparation and uses of a synthetic expression cassette to direct production of Kcna2 sense fragment molecules. The expression cassette comprises (a) a DNA sequence encoding a Kcna2 sense fragment. The expression cassette can be constructed using ordinary molecular cloning techniques, which are well known to those of ordinary skill in the art. The separate elements of the expression cassette can be cloned (e.g., using PCR) or synthesized and ligated together to construct the cassette. If desired, the sequence of the construct can be confirmed by standard sequencing techniques.

In particular embodiments, the expression cassette can comprise a DNA sequence encoding the Kcna sense fragment shown in SEQ ID NOS:7-17.

While the invention provides the expression cassette in isolated form, the invention also pertains to a population comprising a plurality of the expression cassettes. Typically, the population includes thousands of such cassettes. The population can be generated by amplification (e.g., using PCR) of a single cassette or by introducing the cassette into a cloning vector (e.g., a plasmid or phage) and amplifying the vector in a suitable host system such as bacteria). It will be observed that the population can be clonal, in which instance, it is substantially homologous (accounting for occasional errors during replication) and most desirably homologous.

The expression cassette can be placed into an expression vector system under control of a suitable promoter. A desired promoter is a constitutively active promoter, such as a human cytomegalovirus (hCMV) immediate-early promoter, although other promoters known to those of skill in the art can be employed. Alternatively, in some embodiments, an inducible promoter or temperature-sensitive promoter can be employed, such as a tetracycline-regulated inducible promoter. Other promoters that can be used in embodiments of the present invention include ubiquitin promoters, such as a ubiquitin C promoter (Invitrogen, Carlsbad, Calif.); a human elongation factor-1E (EF-1E) promoter available from Invitrogen (Carlsbad, Calif.); a Rous Sarcoma Virus (RSV) promoter, as described, for example, in Yamamoto, et al., Cell 22(3):787-97 (1980); an HSV ICP0 promoter; and an HSV LAP2 promoter, described in U.S. Pat. No. 5,849,571. Techniques for introducing genetic constructs, such as the inventive expression cassette, into expression vector systems are known, and any suitable technique (such as homologous recombination) can be employed.

In a specific embodiment, the vector system is an HSV based viral vector system suitable for use as a vector to introduce a nucleic acid sequence into numerous cell types. The mature HSV virion consists of an enveloped icosahedral capsid with a viral genome consisting of a linear double-stranded DNA molecule that is 152 kb. In a more specific embodiment, the HSV based viral vector is deficient in at least one essential HSV gene. Of course, the vector can alternatively or in addition be deleted for non-essential genes. In another specific embodiment, the HSV based viral vector that is deficient in at least one essential HSV gene is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP 4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, 5,849,572, and 5,804,413, and International Patent Applications WO 91/02788, WO 96/04394, WO 98/15637, and WO 99/06583, which are incorporated herein by reference. In certain embodiments, the HSV vector is "multiply deficient," meaning that the HSV vector is deficient in more than one gene function required for viral replication.

The HSV vector can be deficient in replication-essential gene functions of the early regions of the HSV genome, the immediate-early regions of the HSV genome, only the late regions of the HSV genome, or both the early and late regions of the HSV genome. The HSV vector also can have essentially the entire HSV genome removed, in which case it is preferred that at least either the viral inverted terminal repeats (ITRs) and one or more promoters or the viral ITRs and a packaging signal are left intact (i.e., an HSV amplicon). The larger the region of the HSV genome that is removed, the larger the piece of exogenous nucleic acid sequence that can be inserted into the genome. In a particular embodiment, the vector of the present invention is a non-amplicon HSV vector.

It should be appreciated that the deletion of different regions of the HSV vector can alter the immune response of the mammal. In particular, the deletion of different regions can reduce the inflammatory response generated by the HSV vector. Furthermore, the HSV vector's protein coat can be modified so as to decrease the HSV vector's ability or inability to be recognized by a neutralizing antibody directed against the wild-type protein coat.

In one embodiment, the HSV vector, when multiply replication deficient, includes a spacer element to provide viral growth in a complementing cell line similar to that achieved by singly replication deficient HSV vectors. The spacer element can contain any nucleic acid sequence or sequences which are of the desired length. The spacer element sequence can be coding or non-coding and native or non-native with respect to the HSV genome, but does not restore the replication essential function(s) to the deficient region. In addition, the inclusion of a spacer element in any or all of the deficient HSV regions will decrease the capacity of the HSV vector for large inserts. The production of HSV vectors involves using standard molecular biological techniques well known in the art.

Replication deficient HSV vectors are typically produced in complementing cell lines that provide gene functions not present in the replication deficient HSV vectors, but required for viral propagation, at appropriate levels in order to generate high titers of viral vector stock. In one embodiment, a cell line complements for at least one and preferably all replication essential gene functions not present in a replication deficient HSV vector. The cell line also can complement non-essential genes that, when missing, reduce growth or replication efficiency (e.g., UL55). The complementing cell line can complement for a deficiency in at least one replication essential gene function encoded by the early regions, immediate-early regions, late regions, viral packaging regions, virus-associated regions, or combinations thereof, including all HSV functions (e.g., to enable propagation of HSV amplicons, which comprise minimal HSV sequences, such as only inverted terminal repeats and the packaging signal or only ITRs and an HSV promoter). The cell line can be further characterized in that it contains the complementing genes in a non-overlapping fashion with the HSV vector, which minimizes, and practically eliminates, the possibility of the HSV vector genome recombining with the cellular DNA. Accordingly, the presence of replication competent HSV is minimized, if not avoided in the vector stock, which, therefore, is suitable for certain therapeutic purposes, especially gene therapy purposes. The construction of complementing cell lines involves standard molecular biology and cell culture techniques well known in the art.

When the vector is a replication deficient HSV, the nucleic acid sequence encoding the Kcna2 sense fragment can be located in the locus of an essential HSV gene, for example, either the ICP4 or the ICP27 gene locus of the HSV genome. The insertion of a nucleic acid sequence into the HSV genome (e.g., the ICP4 or the ICP27 gene locus of the HSV genome) can be facilitated by known methods, for example, by the introduction of a unique restriction site at a given position of the HSV genome.

In a specific embodiment, an HSV vector for use in the context of the invention contains expanded ICP4, or ICP27 deletions, and preferably both. By "expanded" deletions in this context, it is meant that such vectors have no homologous sequences at either or both of these loci relative to the complementing cell line used for their production. In another specific embodiment, the virus has no remaining ICP4 or ICP27 (or both) coding or promoter sequences. In a further embodiment, the deletion in ICP27 extends as well into the UL55 locus, and desirably both genes are deleted. Thus, in a particular embodiment, a virus contains extended deletions in ICP4, ICP27 and UL 55 such that there is no viral homology to these genes used in a complementing cell line. Desirably, the vector further does not include any homologous DNA sequences to that employed in the complementing cell line (e.g., even using different regulatory sequences and polyadenylation sequences). For more information on HSV vectors, see U.S. Pat. No. 8,003,622; and U.S. patent application Publication No. 20110112175.

In a specific embodiment, the replication-defective HSV-based vector known as NP2. See Fink et al., 70 ANN. NEUROL. 207-12 (2011); Fink, D. and Wolfe, D., 1(5) PAIN MANAG. 379-81 (2011).

It will be understood that other vectors in addition to HSV vectors can also be used in preparing the gene transfer vectors. For example, adenoviral, adeno-associated viral, and retroviral vectors can be used in the methods and compositions of the present invention. Construction of such vectors is known to those of ordinary skill in the art (see, e.g., U.S. Pat. Nos. 4,797,368, 5,691,176, 5,693,531, 5,880, 102, 6,210,393, 6,268,213, 6,303,362, and 7,045,344). Non-viral methods can also be utilized for gene delivery such as gene-gun application of a plasmid encoding the Kcna2 sense fragment. Another non-viral method of gene delivery is intrathecal electroporation of a drug regulated expression system.

The present invention further provides a method of treating pain comprising administering the vector to a patient or subject. In particular embodiments, the patient is a mammal, such as a rat, mouse, rabbit, cat, dog, horse, cow, pig, or primate. More preferably, the patient is a human. In certain embodiments, the pain is neuropathic pain. In other embodiments, the pain can be associated with inflammation. In further embodiments, the pain can be associated with cancer. In particular embodiments, the pain is associated with spinal cord injury. The Kcna2 fragments of the present invention can be used to treat conditions associated with the upregulation of long non-coding Kcna2 RNA, which downregulates Kcna2 mRNA/protein.

Suitable methods of administering the inventive vector and composition of the invention to an animal (especially a human) for therapeutic or prophylactic purposes, e.g., gene therapy, vaccination, and the like, are available, and, although more than one route can be used to administer the composition, a particular route can provide a more immediate and more effective reaction than another route. In one embodiment, the route of administration involves transduction of dorsal root ganglion neurons through peripheral inoculation to result in vector delivery to the dorsal horn. In many embodiments, this can be accomplished by delivering the gene transfer vector by subcutaneous inoculation. Subcutaneous administration may occur at a location proximate to the dorsal root ganglion or the spinal cord, or at another location at the discretion of the treating clinician, such as a location convenient for administration. In other embodiments, the gene transfer vector can be administered to the dorsal root ganglion of the patient. In still other embodiments, the gene transfer vector can be administered to the spinal cord of the patient.

It will be observed that, for use in therapy, the vector can be formulated into a pharmaceutical composition comprising the vector and a pharmaceutically-acceptable carrier.

Any suitable formulation can be used, depending on the desired route of administration (e.g., oral, transdemial, nasal, or injection (e.g., subcutaneous, intravenous, parenteral, intracranial, intraspinal, etc.)). Thus, the vector can be formulated into ointments, creams, salves and the like for topical administration. The vector can be formulated as an aerosol (e.g., for administration using a nebulizer) for bronchial delivery. The vector alternatively can be formulated in a suitable buffer (e.g., physiological saline) for injection.

The dose administered to an animal, particularly a human, in the context of the invention will vary with the particular vector, the composition containing the vector and the carrier therefor (as discussed above), the method of administration, and the particular site and organism being treated. The dose should be sufficient to effect a desirable response, e.g., therapeutic or prophylactic response, within a desirable time frame. Thus, the dose of the vector of the inventive composition typically will be about $1 \times 10^5$ or more particle units (e.g., about $1 \times 10^6$ or more particle units, about $1 \times 10^7$ or more particle units, $1 \times 10^8$ or more particle units, $1 \times 10^9$ or more particle units, $1 \times 10^{10}$ or more particle units, $1 \times 10^{11}$ or more particle units, or about $1 \times 10^{12}$ or more particle units).

IV. Other Methods for Blocking Long Non-Coding Kcna2 RNA

A. RNA Interference Compositions for Targeting Long Non-Coding Kcna2 RNA mRNAs

In one aspect of the present invention, the expression of long non-coding Kcna2 RNA may be inhibited by the use of RNA interference techniques (RNAi). RNAi is a remarkably efficient process whereby double-stranded RNA (dsRNA) induces the sequence-specific degradation of homologous mRNA in animals and plant cells. See Hutvagner and Zamore, 12 CURR. OPIN. GENET. DEV. 225-32 (2002); Hammond et al., 2 NATURE REV. GEN. 110-19 (2001); Sharp, 15 GENES DEV. 485-90 (2001). RNAi can be triggered, for example, by nucleotide (nt) duplexes of small interfering RNA (siRNA) (Chiu et al., 10 MOL. CELL. 549-61 (2002); Elbashir et al., 411 Nature 494-98 (2001)), micro-RNAs (miRNA), functional small-hairpin RNA (shRNA), or other dsRNAs which are expressed in-vivo using DNA templates with RNA polymerase III promoters. See, e.g., Zeng et al., 9 MOL. CELL. 1327-33 (2002); Paddison et al., 16 GENES DEV. 948-58 (2002); Lee et al., 20 NATURE BIOTECHNOL. 500-05 (2002); Paul et al., 20 NATURE BIOTECHNOL. 505-08 (2002); Tuschl, 20 NATURE BIOTECHNOL. 440-48 (2002); Yu et al., 99(9) PROC. NATL. ACAD. SCI. USA, 6047-52 (2002); McManus et al., 8 RNA 842-50 (2002); Sui et al., 99(6) PROC. NATL. ACAD. SCI. USA 5515-20 (2002).

1. Small Interfering RNA

In particular embodiments, the present invention features "small interfering RNA molecules" ("siRNA molecules" or "siRNA"), methods of making siRNA molecules and methods for using siRNA molecules (e.g., research and/or therapeutic methods). The siRNAs of this invention encompass any siRNAs that can modulate the selective degradation of long non-coding Kcna2 RNA mRNA.

In a specific embodiment, the siRNA of the present invention may comprise double-stranded small interfering RNA molecules (ds-siRNA). A ds-siRNA molecule of the present invention may be a duplex made up of a sense strand and a complementary antisense strand, the antisense strand being sufficiently complementary to a target long non-coding Kcna2 RNA mRNA to mediate RNAi. The siRNA molecule may comprise about 10 to about 200 or more nucleotides. More specifically, the siRNA molecule may comprise about 16 to about 150, e.g., 16, 17, 18, 19, 20, 21, 22, 23, 24, 25, 26, 27, 28, 29, or 30 nucleotides in each strand. The strands may be aligned such that there are at least 1, 2, or 3 bases at the end of the strands which do not align (e.g., for which no complementary bases occur in the opposing strand) such that an overhang of 1, 2 or 3 residues occurs at one or both ends of the duplex when strands are annealed.

In an alternative embodiment, the siRNA of the present invention may comprise single-stranded small interfering RNA molecules (ss-siRNA). Similar to the ds-siRNA molecules, the ss-siRNA molecule may comprise about 10 to about 50 or more nucleotides. More specifically, the ss-siRNA molecule may comprise about 15 to about 45 or more nucleotides. Alternatively, the ss-siRNA molecule may comprise about 19 to about 40 nucleotides. The ss-siRNA molecules of the present invention comprise a sequence that is "sufficiently complementary" to a target mRNA sequence to direct target-specific RNA interference (RNAi), as defined herein, e.g., the ss-siRNA has a sequence sufficient to trigger the destruction of the target mRNA by the RNAi machinery or process. In one embodiment, the ss-siRNA molecule can be designed such that every residue is complementary to a residue in the target molecule. Alternatively, substitutions can be made within the molecule to increase stability and/or enhance processing activity of the molecule. Substitutions can be made within the strand or can be made to residues at the ends of the strand. In a specific embodiment, the 5'-terminus may be phosphorylated (e.g., comprises a phosphate, diphosphate, or triphosphate group). In another embodiment, the 3' end of an siRNA may be a hydroxyl group in order to facilitate RNAi, as there is no requirement for a 3' hydroxyl group when the active agent is a ss-siRNA molecule. In other instances, the 3' end (e.g., C3 of the 3' sugar) of ss-siRNA molecule may lack a hydroxyl group (e.g., ss-siRNA molecules lacking a 3' hydroxyl or C3 hydroxyl on the 3' sugar (e.g., ribose or deoxyribose).

In another aspect, the siRNA molecules of the present invention may be modified to improve stability under in vitro and/or in vivo conditions, including, for example, in serum and in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the siRNAs in tissue culture medium.

Furthermore, the siRNAs of the present invention may include modifications to the sugar-phosphate backbone or nucleosides. These modifications can be tailored to promote selective genetic inhibition, while avoiding a general panic response reported to be generated by siRNA in some cells. In addition, modifications can be introduced in the bases to protect siRNAs from the action of one or more endogenous enzymes.

In an embodiment of the present invention, the siRNA molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues. Examples of nucleotide analogues include sugar- and/or backbone-modified ribonucleotides (e.g., include modifications to the phosphate-sugar backbone). For example, the phosphodiester linkages of natural RNA may be modified to include at least one of a nitrogen or sulfur heteroatom. In backbone-modified ribonucleotides, the phosphoester group connecting to adjacent ribonucleotides may be replaced by a modified group, e.g., a phosphothioate group. In sugar-modified ribonucleotides, the 2' OH-group may be replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Nucleobase-modified ribonucleotides may also be utilized, e.g., ribonucleotides containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Derivatives of siRNAs may also be utilized herein. For example, cross-linking can be employed to alter the pharmacokinetics of the composition, e.g., to increase half-life in the body. Thus, the present invention includes siRNA derivatives that include siRNA having two complementary strands of nucleic acid, such that the two strands are crosslinked. The present invention also includes siRNA derivatives having a non-nucleic acid moiety conjugated to its 3' terminus (e.g., a peptide), organic compositions (e.g., a dye), or the like. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The siRNAs of the present invention can be enzymatically produced or totally or partially synthesized. Moreover, the siRNAs can be synthesized in vivo or in vitro. For siRNAs that are biologically synthesized, an endogenous or a cloned exogenous RNA polymerase may be used for transcription in vivo, and a cloned RNA polymerase can be used in vitro. siRNAs that are chemically or enzymatically synthesized are preferably purified prior to the introduction into the cell.

Although one hundred percent (100%) sequence identity between the siRNA and the target region is preferred in particular embodiments, it is not required to practice the invention. siRNA molecules that contain some degree of modification in the sequence can also be adequately used for the purpose of this invention. Such modifications may include, but are not limited to, mutations, deletions or insertions, whether spontaneously occurring or intentionally introduced.

Moreover, not all positions of a siRNA contribute equally to target recognition. In certain embodiments, for example, mismatches in the center of the siRNA may be critical and could essentially abolish target RNA cleavage. In other embodiments, the 3' nucleotides of the siRNA do not contribute significantly to specificity of the target recognition. In particular, residues 3' of the siRNA sequence which is complementary to the target RNA (e.g., the guide sequence) may not critical for target RNA cleavage.

Sequence identity may be determined by sequence comparison and alignment algorithms known to those of ordinary skill in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (e.g., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (e.g., a local alignment). A non-limiting example of a local alignment algorithm utilized for the comparison of sequences is the algorithm of Karlin and Altschul, 87 Proc. Natl. Acad. Sci. USA 2264-68 (1990), and as modified as in Karlin and Altschul 90 Proc. Natl. Acad. Sci. USA 5873-77 (1993). Such an algorithm is incorporated into the BLAST programs (version 2.0) of Altschul, et al., 215 J. Mol. Biol., 403-10 (1990).

In another embodiment, the alignment may optimized by introducing appropriate gaps and determining percent identity over the length of the aligned sequences (e.g., a gapped alignment). To obtain gapped alignments for comparison purposes, Gapped BLAST can be utilized as described in Altschul et al., 25(17) Nucleic Acids Res. 3389-3402 (1997). In another embodiment, the alignment may be optimized by introducing appropriate gaps and determining percent identity over the entire length of the sequences aligned (e.g., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

In particular embodiments, greater than 90% sequence identity, e.g., 91%, 92%, 93%, 94%, 95%, 96%, 97%, 98%, 99° A or even 100% sequence identity, between the siRNA and the portion of the target gene may be used. Alternatively, the siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional hybridization conditions include, but are not limited to, hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length can be about 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+ 16.6(log 10[$Na^+$])+0.41(% G+C)-(600/N), where N is the number of bases in the hybrid, and [Na] is the concentration of sodium ions in the hybridization buffer ([$Na^+$] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 50 or more bases.

2. Other Compositions for Targeting Long Non-Coding Kcna2 RNA DNA or mRNA

Antisense molecules can act in various stages of transcription, splicing and translation to block the expression of a target gene. Without being limited by theory, antisense molecules can inhibit the expression of a target gene by inhibiting transcription initiation by forming a triple strand, inhibiting transcription initiation by forming a hybrid at an RNA polymerase binding site, impeding transcription by hybridizing with an RNA molecule being synthesized, repressing splicing by hybridizing at the junction of an exon and an intron or at the spliceosome formation site, blocking the translocation of an mRNA from nucleus to cytoplasm by hybridization, repressing translation by hybridizing at the translation initiation factor binding site or ribosome biding site, inhibiting peptide chain elongation by hybridizing with the coding region or polysome binding site of an mRNA, or repressing gene expression by hybridizing at the sites of interaction between nucleic acids and proteins. An example of an antisense oligonucleotide of the present invention is a cDNA that, when introduced into a cell, transcribes into an RNA molecule having a sequence complementary to at least part of the long non-coding Kcna2 RNA mRNA.

Furthermore, antisense oligonucleotides of the present invention include oligonucleotides having modified sugar-phosphodiester backbones or other sugar linkages, which can provide stability against endonuclease attacks. The present invention also encompasses antisense oligonucleotides that are covalently attached to an organic or other moiety that increase their affinity for a target nucleic acid sequence. For example, intercalating agents, alkylating agents, and metal complexes can be also attached to the antisense oligonucleotides of the present invention to modify their binding specificities.

The present invention also provides ribozymes as a tool to inhibit long non-coding Kcna2 RNA expression. Ribozymes are enzymatic RNA molecules capable of catalyzing the specific cleavage of RNA. The characteristics of ribozymes are well-known in the art. See, e.g., Rossi, 4 CURRENT BIOLOGY 469-71 (1994). Without being limited by theory, the mechanism of ribozyme action involves sequence specific hybridization of the ribozyme molecule to complementary target RNA, followed by an endonucleolytic cleavage. In particular embodiments, the ribozyme molecules include one or more sequences complementary to the target gene mRNA, and include the well known catalytic sequence responsible for mRNA cleavage. See U.S. Pat. No. 5,093, 246. Using the known sequence of the target long non-coding Kcna2 RNA mRNA, a restriction enzyme-like ribozyme can be prepared using standard techniques.

The expression of the long non-coding Kcna2 RNA gene can also be inhibited by using triple helix formation. Nucleic acid molecules to be used in triple helix formation for the inhibition of transcription can be single stranded and composed of deoxynucleotides. The base composition of these oligonucleotides must be designed to promote triple helix formation via Hoogsteen base paring rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules that are purine-rich, e.g., containing a stretch of G residues, may be chosen. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3',3'-5' manner, such that they base pair first with one strand of a duplex and then the other, eliminating the necessity for a sizeable stretch of either purines or pyrimidines to be present on one strand of a duplex.

The expression of long non-coding Kcna2 RNA may be also inhibited by what is referred to as "co-repression." Co-repression refers to the phenomenon in which, when a gene having an identical or similar to the target sequence is introduced to a cell, expression of both introduced and endogenous genes becomes repressed. This phenomenon, although first observed in plant system, has been observed in certain animal systems as well. The sequence of the gene to be introduced does not have to be identical to the target sequence, but sufficient homology allows the co-repression to occur. The determination of the extent of homology depends on individual cases, and is within the ordinary skill in the art.

It would be readily apparent to one of ordinary skill in the art that other methods of gene expression inhibition that selectively target long non-coding Kcna2 RNA DNA or mRNA can also be used in connection with this invention without departing from the spirit of the invention. In a specific embodiment, using techniques known to those of ordinary skill in the art, the present invention contemplates affecting the promoter region of long non-coding Kcna2 RNA to effectively switch off transcription.

3. Design and Production of the RNAi Compositions

One or more of the following guidelines may be used in designing the sequence of siRNA and other nucleic acids designed to bind to a target mRNA, e.g., shRNA, stRNA, antisense oligonucleotides, ribozymes, and the like, that are advantageously used in accordance with the present invention.

Beginning with the AUG start codon of the long non-coding Kcna2 RNA gene, each AA dinucleotide sequence and the 3' adjacent 16 or more nucleotides are potential siRNA targets. In a specific embodiment, the siRNA is specific for a target region that differs by at least one base pair between the wild type and mutant allele or between splice variants. In dsRNAi, the first strand is complementary to this sequence, and the other strand identical or substantially identical to the first strand. siRNAs with lower G/C content (35-55%) may be more active than those with G/C content higher than 55%. Thus in one embodiment, the invention includes nucleic acid molecules having 35-55% G/C content. In addition, the strands of the siRNA can be paired in such a way as to have a 3' overhang of 1 to 4, e.g., 2, nucleotides. Thus in another embodiment, the nucleic acid molecules may have a 3' overhang of 2 nucleotides, such as TT. The overhanging nucleotides may be either RNA or DNA. In one embodiment, it may be desirable to choose a target region wherein the mismatch is a purine:purine mismatch.

Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website (http://www.ncbi.nih.gov). Select one or more sequences that meet the criteria for evaluation.

Another method includes selecting in the sequence of the target mRNA, a region located from about 50 to about 100 nt 3' from the start codon. In this region, search for the following sequences: AA(N19)TT or AA(N21), where N=any nucleotide. The GC content of the selected sequence should be from about 30% to about 70%, preferably about 50%. To maximize the specificity of the RNAi, it may be desirable to use the selected sequence in a search for related sequences in the genome of interest; sequences absent from other genes are preferred. The secondary structure of the target mRNA may be determined or predicted, and it may be preferable to select a region of the mRNA that has little or no secondary structure, but it should be noted that secondary structure seems to have little impact on RNAi. When possible, sequences that bind transcription and/or translation factors should be avoided, as they might competitively inhibit the binding of a siRNA, sbRNA or stRNA (as well as other antisense oligonucleotides) to the mRNA. Further general information about the design and use of siRNA may be found in "The siRNA User Guide," available at The Max-Planck-Institut fur Biophysikalishe Chemie website (http://www.mpibpc.mpg.de).

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome.

4. Delivery of Long Non-Coding Kcna2 RNA Targeting Compositions

Delivery of the compositions of the present invention (e.g., siRNAs, antisense oligonucleotides, or other compositions described herein) into a patient can either be direct, e.g., the patient is directly exposed to the compositions of the present invention or compound-carrying vector, or indirect, e.g., cells are first transformed with the compositions of this invention in vitro, then transplanted into the patient for cell replacement therapy. These two approaches are known as in vivo and ex vivo therapy, respectively.

In the case of in vivo therapy, the compositions of the present invention are directly administered in vivo, where they are expressed to produce the encoded product. This can be accomplished by any of numerous methods known in the art, e.g., by constructing them as part of an appropriate nucleic acid expression vector and administering them so that they become intracellular, by infection using a defective or attenuated retroviral or other viral vector, by direct injection of naked DNA, by coating with lipids or cell-surface receptors or transfecting agents, encapsulation in liposomes, nanoparticles, microparticles, or microcapsules, by administering them in linkage to a peptide which is known to enter the cell or nucleus, or by administering them in linkage to a ligand subject to receptor-mediated endocytosis which can be used to target cell types specifically expressing the receptors. Further, the compositions of the present invention can be targeted in vivo for cell specific uptake and expression, by targeting a specific receptor. See, e.g., WO93/14188, WO 93/20221, WO 92/22635, WO92/20316, and WO 92/06180.

Ex vivo therapy involves transferring the compositions of the present invention to cells in tissue culture by methods well-known in the art such as electroporation, transfection, lipofection, microinjection, calcium phosphate mediated transfection, cell fusion, chromosome-mediated gene transfer, microcell-mediated gene transfer, spheroplast fusion, and infection with a viral vector containing the nucleic acid sequences. These techniques should provide for the stable transfer of the compositions of this invention to the cell, so that they are expressible by the cell and preferably heritable and expressible by its cell progeny. In particular embodiments, the method of transfer includes the transfer of a selectable marker to the cells. The cells are then placed under selection to isolate those cells that have taken up and are expressing the transferred compositions. The resulting recombinant cells can be delivered to a patient by various methods known in the art. Examples of the delivery methods include, but are not limited to, subcutaneous injection, skin graft, and intravenous injection.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Animals. Male Sprague-Dawley rats weighing 200-250 g were kept in a standard 12-h light/dark cycle, with water and food pellets available ad libitum. All procedures used were approved by the Animal Care and Use Committee at the Johns Hopkins University and consistent with the ethical guidelines of the US National Institutes of Health and the International Association for the Study of Pain. All efforts were made to minimize animal suffering and to reduce the number of animals used. All of the experimenters were blind to treatment condition.

Nerve Injury Models. L5 spinal nerve ligation (SNL)[39, 40, 41], chronic constriction injury (CCI)[42] and sciatic nerve axotomy[39] models of neuropathic pain were carried out as described previously. Sham-operated groups underwent identical procedures but without transection of the respective nerve.

Behavioral Analysis. Mechanical, cold, thermal and locomotor behavioral tests were carried out. Each behavioral test was carried out at 1-h intervals. Paw withdrawal thresholds in response to mechanical stimuli were first measured with the up-down testing paradigm as described previously[39]. Paw withdrawal latencies to noxious cold (0° C.) were then measured with a cold plate, the temperature of which was monitored continuously. Each animal was placed in a Plexiglas chamber on the cold plate, which was set at 0° C. The length of time between the placement of the hind paw on the plate and the animal jumping, with or without paw licking and flinching, was defined as the paw withdrawal latency. Each trial was repeated three times at 10-min intervals for the paw on the ipsilateral side. A cutoff time of 60 s was used to avoid tissue damage. Finally, paw withdrawal latencies to noxious heat were measured with Model 336 Analgesia Meter (IITC Inc./Life Science Instruments, Woodland Hills, Calif., USA) as described previously[41]. Tests of locomotor function, including placing, grasping and righting reflexes, were performed before and after viral injection according to previously described protocols[39, 40, 43].

Cell Line Culture and Transfection. HEK-293T cells were cultured in Dulbecco's modified Eagle's medium at 37° C. in a humidified incubator with 5% $CO_2$. The plasmids were transfected into the HEK-293T cells with Lipofectamine 2000 (Invitrogen, Carlsbad, Calif.) according to the manufacturer's instructions.

DRG Neuronal Culture and AAV5 Transduction. Adult male rats were put to death with isoflurane. DRGs were collected in cold DH10 (90% DMEM/F-12 (Gibco, Grand Island, N.Y.), 10% FBS (JR Scientific, Woodland, Calif.), 1% penicillin-streptomycin (Quality Biological, Gaithersburg, Md.)) and then treated with enzyme solution (3.5 mg/ml dispase, 1.6 mg/ml collagenase type I in HBSS without $Ca^{2+}$ and $Mg^{2+}$ (Gibco)) at 37° C. After the centrifugation, dissociated cells were resuspended in DH10 and plated at a density of $1.5 \times 10^5$ to $4 \times 10^5$ cells on glass coverslips or in a six-well plate coated with poly-L-lysine (0.5 mg/ml, Sigma, St. Louis, Mo.) and laminin (10 µg/ml, Invitrogen). The cells were incubated in 5% $CO_2$ at 37° C. One day later, 1 µl of AAV5 virus (titer $\geq 1 \times 10^{12}$/ml) was added to each well. Cells were collected 4 d later.

Reverse Transcription (RT)-PCR, Rapid Amplification of cDNA Ends (RACE) and Quantitative RT-PCR. Total RNA was extracted by the Trizol method (Invitrogen) and treated with excess DNase I (New England Biolabs, Ipswich, Mass.). Highly purified, DNase-treated RNA samples from human DRG were purchased from Clontech Laboratories, Inc. (Mountain View, Calif.). Using the Omniscript RT kit (QIAGEN, Valencia, Calif.) with strand-specific primers, we reverse transcribed single-stranded cDNA from RNA (1 µg). RT and PCR primers were determined from the UCSC genome database (Supplementary Table 2). Template (1 µl) was amplified by PCR with TaKaRa Taq DNA polymerase (Clontech Laboratories, Inc.) in 20 µl total reaction volume containing 0.5 µM of PCR primer. PCR amplification consisted of 30 s at 94° C., 20 s at 56° C., and 20 s at 72° C. for 35 cycles.

RNA fragments amplified from the rat DRG were extended first by using RT-PCR with strand-specific primers and then by using a RACE kit (2nd Generation, Roche Diagnostics, Indianapolis, Ind.). The 5' RACE was used for amplification of the 5'-end of cDNA according to the manufacturer's instructions. The 3' RACE analysis was performed by ligating an adaptor to the 3-hydroxyl group of the RNA, followed by gene- and adaptor-specific amplification. All primers are listed in Supplementary Table 2. PCR products from RT-PCR, 5' RACE and 3' RACE were extracted, purified and verified by automated DNA sequencing. All sequences were analyzed and the full-length Kcna2 antisense RNA sequence determined.

Figure 15A:
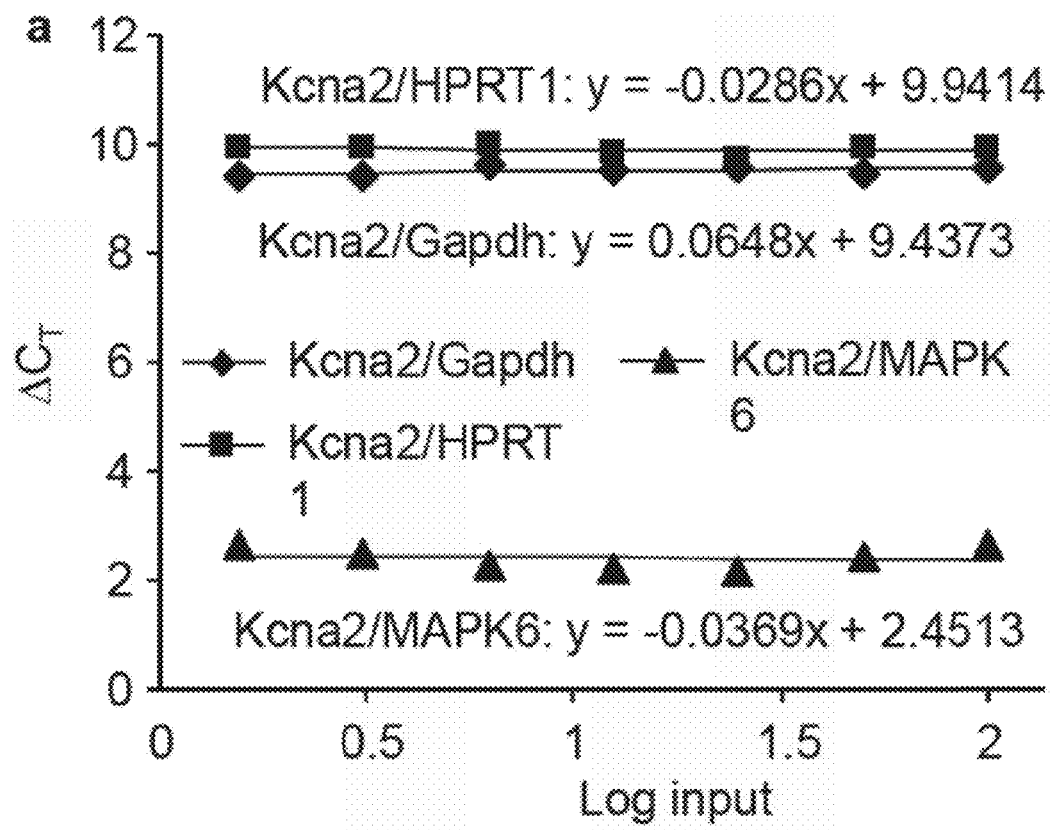
Figure 15B:
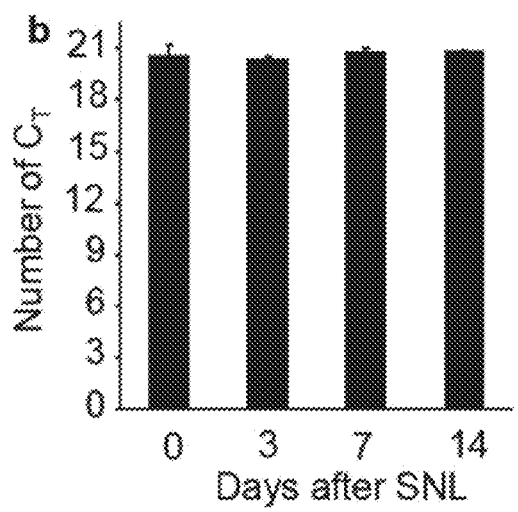
Figure 15C:
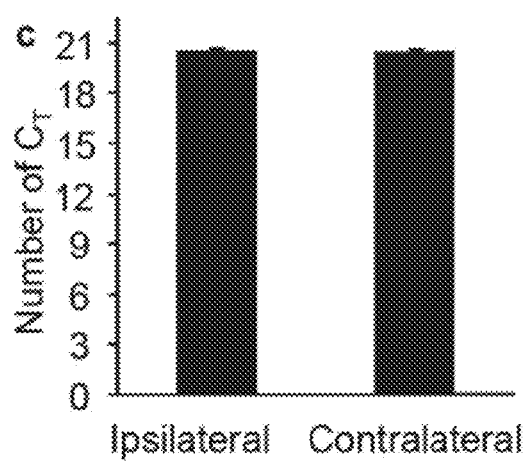
Figure 15D:
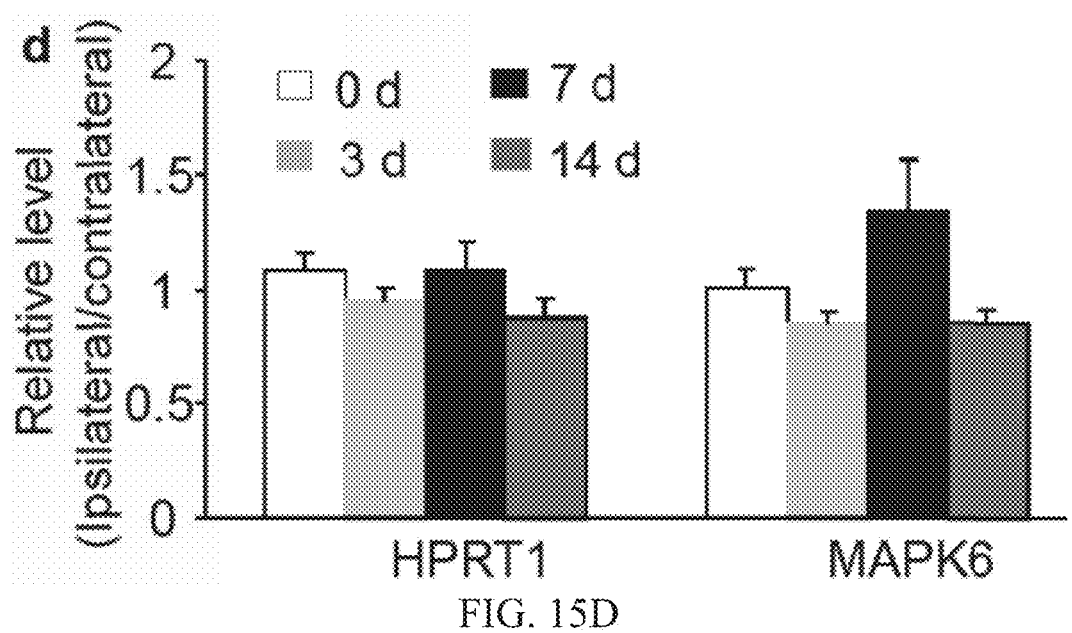

For quantitative real-time RT-PCR, three DRGs from three individual rats were pooled to provide enough RNA. cDNA was prepared as described above. Template (1 µl) was amplified by real-time PCR by using 1 µM of each probe and 0.5 µM of each primer listed in Supplementary Table 2. Each sample was run in quadruplicate in a 20-µl reaction with the TaqMan Universal PCR master mix kit (Applied Biosystems, Grand Island, N.Y.). Reactions were performed in 96-well plates in an ABI 7500 Fast real-time PCR system (Applied Biosystems). Ratios of ipsilateral mRNA to contralateral mRNA were calculated by using the ΔCt method ($2^{-\Delta\Delta Ct}$) at a threshold of 0.02, as our pilot data indicated that the amplification reactions of the target genes and reference genes have similar PCR efficiency (FIG. 15a). All data were normalized to Gapdh, which was demonstrated to be stable after SNL (FIG. 15b-d).

For single-cell quantitative RT-PCR, freshly dissociated rat DRG neurons were first prepared as described below. Four hours after plating, small, medium and large DRG neurons were randomly collected under an inverted microscope fit with a micromanipulator and microinjector. A single living neuron was selected with a glass micropipette, without contamination by other neurons, and placed in a PCR tube with 6 µl of cell lysis buffer (Signosis, Sunnyvale, Calif.) as described[44]. After centrifugation, the supernatants were collected. The remaining real-time RT-PCR procedure was carried out as described[44] or according to the manufacturer's instructions with the single-cell real-time RT-PCR assay kit (Signosis).

rAAV5 Plasmid Constructs and Virus Production. After RNA was extracted from the DRG, full-length Kcna2 antisense cDNA, full-length Mzf1 cDNA and Kcna2 sense cDNA fragment (−311 to +40) were amplified by nested RT-PCR (primers in Supplementary Table 2). Restriction enzyme recognition sites were introduced at the 5' and 3' ends of the three fragments. The PCR products were cloned by using the pGEM-T easy cloning kit (Invitrogen). The positive clones were identified by restriction enzyme analysis (BspEI/NotI) and clone sequencing.

The identified fragments were ligated into the BspEI/NotI sites of the proviral plasmids (University of North Carolina, Chapel Hill) to replace enhanced GFP (EGFP) and the S-D sequence. The resulting four vectors expressed EGFP, Kcna2 antisense RNA, Kcna2 sense fragment and MZF1 under the control of the cytomegalovirus promoter. rAAV5 viral particles carrying the four cDNAs were produced at the University of North Carolina Vector Core.

Northern Blotting. To prepare complementary RNA (cRNA) probes of rat Kcna2 antisense RNA, we constructed the pSC-A plasmid, which contained a 0.946-kb DNA template, and identified the sequence using double-strand DNA sequencing. The plasmid construct was linearized by Acc65I and XhoI. A riboprobe was generated from in vitro transcription and labeled with $^{32}$P-dUTP.

Northern blot analysis was performed as described previously[45]. The extracted RNA (10 µg) was separated on a 1.5% agarose/formaldehyde gel, transferred to a BrightStarplus positively charged nylon membrane and cross-linked by using ultraviolet light. After prehybridization, the membrane was hybridized overnight at 68° C. with $^{32}$P-dUTP-labeled cRNA probes for Kcna2 antisense RNA. After the membrane was washed and dried, autoradiography was carried out.

In Situ Hybridization Histochemistry. In situ hybridization histochemistry was carried out as described previously with minor modification[46, 47]. Two sets of 20-μm sections were collected from each DRG by grouping every third section. Kcna2 cRNA probe (0.268-kb fragment) and GFP cRNA probe (0.187-kb fragment) were prepared by in vitro transcription and labeled with digoxigenin-dUTP according to the manufacturer's instructions (Roche Diagnostics, Indianapolis, Ind.). After treatment with proteinase K and prehybridization, the two sets of sections were hybridized with digoxigenin-dUTP-labeled cRNA probes for Kcna2 antisense RNA and GFP RNA for 18 h at 68° C. After being washed, the sections were incubated with alkaline phosphatase-conjugated anti-digoxigenin. The signals were developed with 5-bromo-4-chloro-3'-indolyl phosphate p-toluidine salt and nitro-blue tetrazolium chloride substrates. For the double labeling of in situ hybridization histochemistry and immunohistochemistry, the sections were treated as described above except that they were hybridized only with digoxigenin-dUTP-labeled cRNA probe for Kcna2 antisense RNA and the fluorescent signals were developed with Fast Red.

Immunohistochemistry. After being blocked for 1 h at 37° C. in PBS containing 10% goat serum and 0.3% Triton X-100, the sections were incubated with rabbit anti-NF200 (1:500, Sigma-Aldrich, St. Louis, Mo.)[48], rabbit anti-P2X3 (1:500, Neuromics, Edina, Minn.)[48], biotinylated IB4 (1:100, Sigma)[48], rabbit anti-CGRP (1:500, EMD, Billerica, Mass.)[48], mouse anti-NeuN (1:600, EMD)[48], mouse anti-GFAP (1:500, Sigma)[48] or mouse anti-OX-42 (1:400, Sigma)[48] overnight at 4° C. The sections were then incubated with goat anti-rabbit IgG conjugated to Cy2 (1:400, Jackson ImmunoResearch, West Grove, Pa.) or Cy3 (1:400, Jackson ImmunoResearch) or with FITC-labeled avidin D (1:200, Sigma) for 2 h at room temperature (25° C.). Control experiments included substitution of normal mouse serum for the primary antiserum and omission of the primary antiserum. All immunofluorescence-labeled images were examined under a Nikon TE2000E fluorescence microscope (Nikon Co., Japan) and captured with a CCD spot camera. Single- and double-labeled neurons were counted by using stereological methods as described[49].

Western Blotting. For DRG, three DRGs from three individual rats were pooled to provide enough protein. The tissues were homogenized and the cultured cells ultrasonicated in chilled lysis buffer (50 mM Tris, 1 mM phenylmethylsulfonyl fluoride, 1 mM EDTA, 1 μM leupeptin). After centrifugation at 4° C. for 15 min at 1,000 g, the supernatant was collected for cytosolic and membrane proteins and the pellet for nuclear proteins. After protein concentration was measured, the samples were heated at 99° C. for 5 min and loaded onto a 4% stacking/7.5% separating SDS-polyacrylamide gel (Bio-Rad Laboratories, Hercules, Calif.). The proteins were then electrophoretically transferred onto a polyvinylidene difluoride membrane (Immobilon-P, Millipore, Billerica, Mass.). According to the targeted protein molecular weights, the membranes were cut into several small strips and then blocked with 3% nonfat milk in Tris-buffered saline containing 0.1% Tween-20 for 1 h. The following primary antibodies were used: mouse anti-Kcna1 (Kv1.1, 1:200, NeuroMab, Davis, Calif.)[9], mouse anti-Kcna2 (Kv1.2, 1:200, NeuroMab)[9], mouse anti-Kcna4 (Kv1.4, 1:300, NeuroMab)[9], rabbit anti-mTOR (1:1,000, Cell Signaling Technology, Danvers, Mass.)[48], rabbit anti-PKCα (1:500, Santa Cruz Biotechnology, Santa Cruz, Calif.)[40], mouse anti-Scn10a (Nav1.8, 1:1,000; NeuroMab)[50], rabbit anti-MZF1 (1:200, provided by D. Y. H. Tuan, Medical College of Georgia)[21], mouse anti-β-actin (1:2,000; Santa-Cruz Biotechnology) and rabbit anti-histone H3 (1:1,000, Cell Signaling Technology). The proteins were detected by horseradish peroxidase-conjugated anti-mouse or anti-rabbit secondary antibody (1:3,000 Jackson ImmunoResearch) and visualized by chemiluminescence regents (ECL; Amersham Pharmacia Biotech, Piscataway, N.J.) and exposure to film. The intensity of blots was quantified with densitometry.

Electrophoretic Mobility Shift Assay. $^{32}$P-labeled double-stranded DNA probe was prepared by annealing synthetic oligonucleotide in H-Star polymerase PCR solution containing $^{32}$P-dCTP, dATP and dTTP at 56° C. for 1 min and then at 72° C. for 30 min. Unlabeled probe and unlabeled mutant probe were similarly prepared for use as competitors. Their oligonucleotide sequences are shown in Supplementary Table 2. All probes were purified in a G50 column (GE Healthcare, Silver Spring, Md.). DRG nuclear extract (5 μg) was incubated with labeled probe (9 ng) alone or with 50× unlabeled probe or 50× unlabeled mutant probe at 25° C. for 20 min. Labeled probe alone was used as a control. After incubation, the DNA-protein complexes were subjected to PAGE. Autoradiography was carried out after the gel was dried. For supershift electrophoretic mobility shift assay, the nuclear extracts were incubated with rabbit MZF1 antibody (2 μg) at 25° C. for 30 min before the assay.

Chromatin Immunoprecipitation Assay. The homogenization solution from the DRG was cross-linked with 1% formaldehyde at 37° C. for 5 min and the reaction terminated by the addition of 0.25 M glycine. After centrifugation, the pellet was collected, washed and suspended in lysis buffer containing 0.1% SDS, 1% sodium deoxycholate and 1% NP-40 in the presence of protease inhibitors. The suspension was sonicated with an ultrasonic cell disruptor (Misonix Inc., Farmingdale, N.Y.) to shear chromatin and produce 0.2- to 1-kb DNA fragments. After the samples were precleared with protein G-agarose, they were immunoprecipitated with 5 μg of rabbit anti-MZF1 (ref 21), normal rabbit serum (5 μg) or rabbit anti-MZF1 (5 μg) after preabsorption with excess MZF-1 fusion protein (10 μg). Input (10% of the sample for immunoprecipitation) was used as a positive control. The fragment (156 nt) of Kcna2 antisense gene promoter containing the predicted MZF1 binding site was detected by PCR. All primers used are listed in Supplementary Table 2.

Luciferase Assay. To construct the Kcna2 gene and Kcna2 antisense gene reporter plasmids, we amplified the 1,268-bp fragment from the Kcna2 gene promoter region and the 633-bp fragment from the Kcna2 antisense gene promoter (including the MZF1-binding motif) by PCR from genomic DNA. The PCR products were subcloned into the SmaI and HindIII restriction sites of the pGL3-Basic vector (Promega, Madison, Wis.). The sequences of recombinant clones were verified by DNA sequencing. All primer sequences are shown in Supplementary Table 2.

HEK-293T cells were prepared as described above. After 24 h of culture, the cells were transfected with 40 ng of the pRL-TK plasmid (a normalizing control; Promega, Madison, Wis.) alone or plus 1 μg of the constructed plasmids using Lipofectamine 2000 (Invitrogen). After another 48 h of culture, the transfected cells were lysed with passive lysis buffer and 40 µl supernatant was assayed for luciferase activity with the Dual-Luciferase Reporter Assay System (Promega). The relative reporter activity was obtained by normalization of the firefly activity to Renilla activity. Three independent transfection experiments were performed.

Whole-Cell Patch Clamp Recording. To record total potassium current in DRG neurons, we first prepared freshly dissociated rat DRG neurons as described above. Whole-cell patch clamp recording was carried out 4 to 24 h after plating. Coverslips were placed in the perfusion chamber (Warner Instruments, Hamden, Conn.). Only green-labeled neurons were recorded. The electrode resistances of micropipettes ranged from 2 to 4 MΩ. Cells were voltage-clamped with an Axopatch-700B amplifier (Molecular Devices, Sunnyvale, Calif.). The intracellular pipette solution contained (in mM) potassium gluconate 120, KCl 20, $MgCl_2$ 2, EGTA 10, HEPES 10, Mg-ATP 4 (pH 7.3 with KOH, 310 mOsm). We minimized the $Na^+$ and $Ca^{2+}$ component in voltage-gated potassium current recording by using an extracellular solution composed of (in mM) choline chloride 150, KCl 5, $CdCl_2$ 1, $CaCl_2$ 2, $MgCl_2$ 1, HEPES 10, glucose 10 (pH 7.4 with Tris base, 320 mOsm). Signals were filtered at 1 kHz and digitized by using a DigiData 1322A with pClamp 9.2 software (Molecular Devices). Series resistance was compensated by 60-80%. Cell membrane capacitances were acquired by reading the value for whole-cell capacitance compensation directly from the amplifier. An online P/4 leak subtraction was performed to eliminate leak current contribution. The data were stored on computer by a DigiData 1322A interface and were analyzed by the pCLAMP 9.2 software package (Molecular Devices).

To record the action potential, we switched the recording mode into current clamp. Coverslips were placed in the chamber and perfused with extracellular solution consisting of (in mM) NaCl 140, KCl 4, $CaCl_2$ 2, $MgCl_2$ 2, HEPES 10 and glucose 5, with pH adjusted to 7.38 by NaOH. The intracellular pipette solution contained (in mM) KCl 135, Mg-ATP 3, $Na_2ATP$ 0.5, $CaCl_2$ 1.1, EGTA 2 and glucose 5; pH was adjusted to 7.38 with KOH and osmolarity adjusted to 300 mOsm with sucrose. The resting membrane potential was taken 3 min after a stable recording was first obtained. Depolarizing currents of 100-1,400 pA (200-ms duration) were delivered in increments of 100 pA until an action potential (AP) was evoked. The injection current threshold was defined as the minimum current required to evoke the first AP. The membrane potential was held at the existing resting membrane potential during the current injection. The AP threshold was defined as the first point on the rapid rising phase of the spike at which the change in voltage exceeded 50 mV/ms. The AP amplitude was measured between the peak and the baseline. The membrane input resistance for each cell was obtained from the slope of a steady-state I-V plot in response to a series of hyperpolarizing currents, 200-ms duration delivered in steps of 100 pA from 200 pA to −2,000 pA. The after-hyperpolarization amplitude was measured between the maximum hyperpolarization and the final plateau voltage, and the AP overshoot was measured between the AP peak and 0 mV. The data were stored on computer by a DigiData 1322A interface and were analyzed by the pCLAMP 9.2 software package (Molecular Devices). All experiments were performed at room temperature.

DRG Microinjection. DRG microinjection was carried out as described[51,52]. Briefly, a midline incision was made in the lower lumbar back region and the L5 vertebral body region exposed. After the lamina was removed and the DRG exposed, viral solution (2 µl) was injected into two sites in the L4 and L5 DRGs or into one site in the L5 DRG with a glass micropipette connected to a Hamilton syringe. The pipette was removed after 10 min. After injection, the skin incision was closed with wound clips. The injected rats showed no signs of paresis or other abnormalities. The injected DRGs, stained with hematoxylin and eosin, retained their structural integrity and contained no visible leukocytes. The immune responses from viral injection were therefore minimal.

Statistical Analysis. For in vitro experiments, the cells were evenly suspended and then randomly distributed in each well tested. For in vivo experiments, the animals were distributed into various treated groups randomly. All of the results are given as means±s.e.m. Data distribution was assumed to be normal, but this was not formally tested. The data were statistically analyzed with two-tailed, paired or unpaired Student's t-test and a one-way or two-way ANOVA. When ANOVA showed significant difference, pairwise comparisons between means were tested by the post hoc Tukey method (SigmaStat, San Jose, Calif.). No statistical methods were used to predetermine sample sizes, but our sample sizes are similar to those reported previously in the fields[39, 40, 41]. Significance was set at $P<0.05$.

Results

Figure 1B:
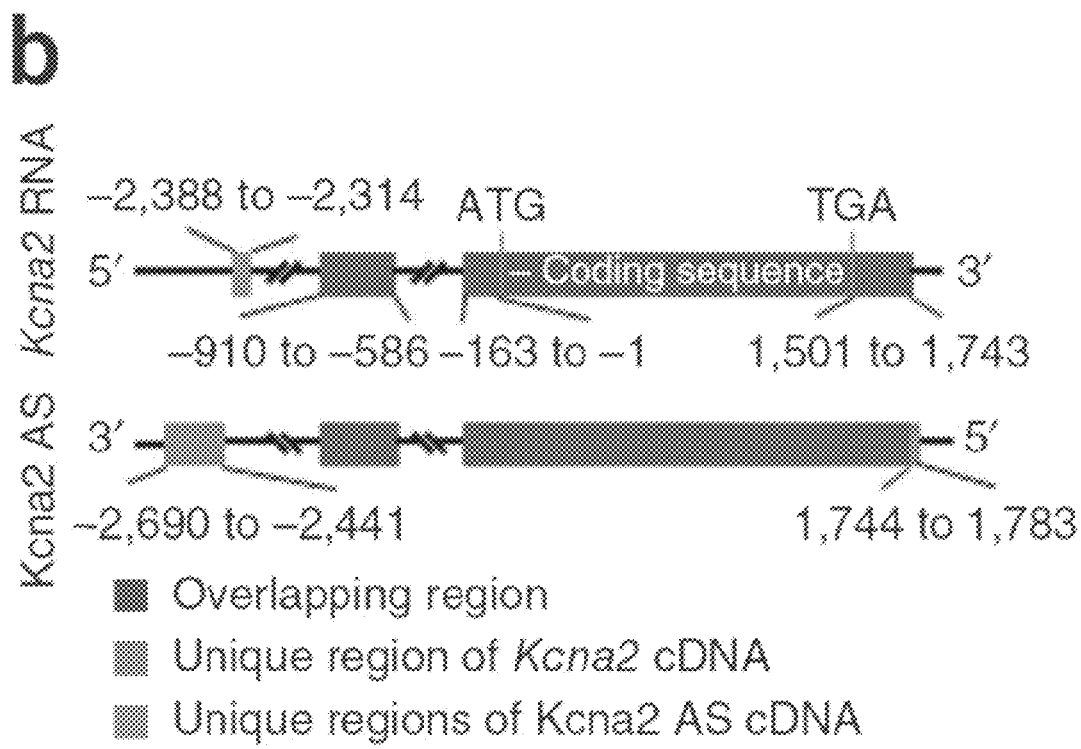
Figure 9A:
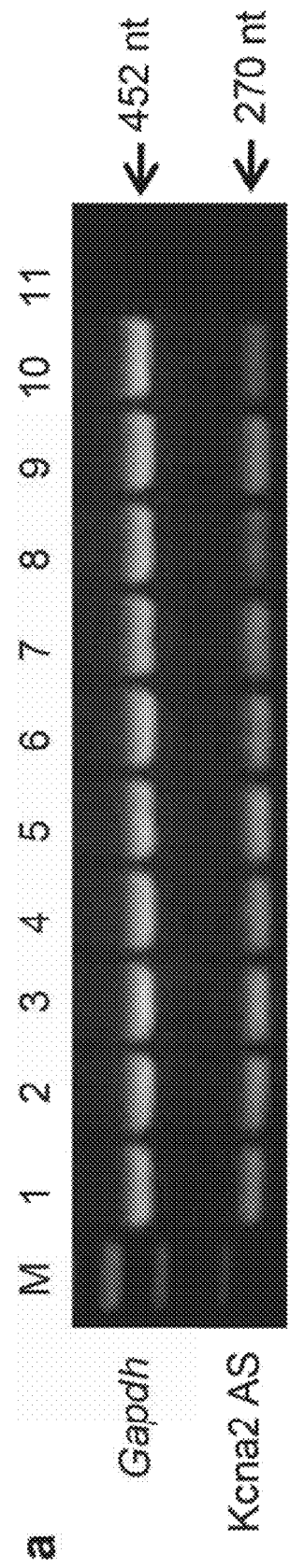
Figure 9B:
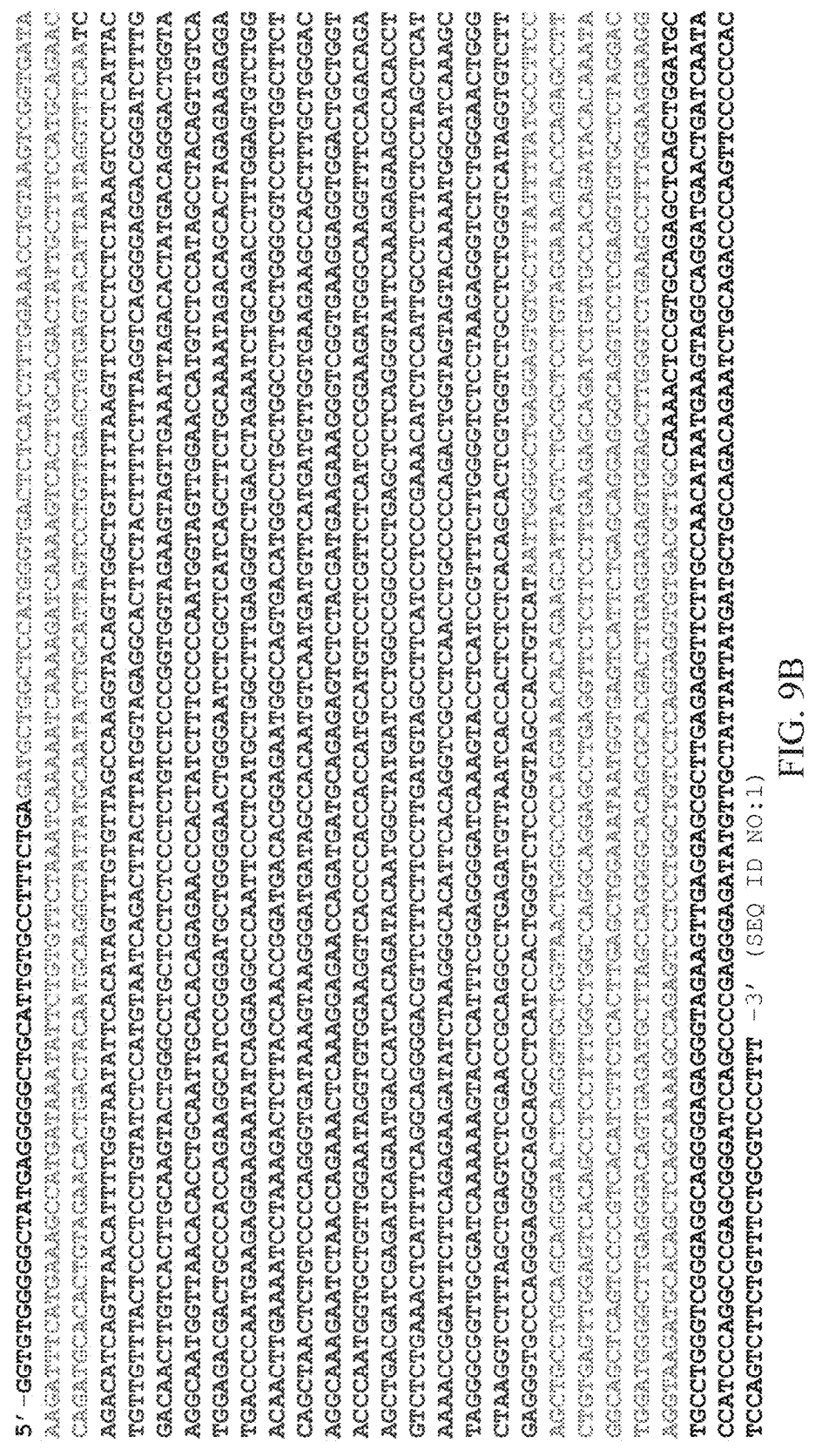

Identification of Natural Kcna2 Antisense RNA in DRG Neurons. To detect Kcna2 antisense RNA, we first searched a database using the complete published Kcna2 cDNA sequence. Although many of the expressed sequence tags reflected portions of Kcna2 transcript, a few were in the antisense direction. Using strand-specific primers for reverse transcription, we identified Kcna2 antisense transcript in the DRGs of rat, mouse, monkey and human (FIG. 1a), although the sequences were not identical among species. We also detected this transcript in spinal cord, various brain regions and other body organs of rats (FIG. 9a). Using rapid amplification of cDNA ends for directional sequencing of 5' and 3' ends, we identified a 2.52-kb Kcna2 antisense RNA in rat DRG (FIG. 9b). Most of its sequence overlapped that of Kcna2 RNA, including the coding sequence, the 3' untranslated region and part of the 5' untranslated region, but Kcna2 antisense RNA had unique regions at the 5' and 3' ends (FIG. 1b). It had no apparent open reading frame (FIG. 9b), indicating that Kcna2 antisense RNA is noncoding RNA.

Figure 1C:
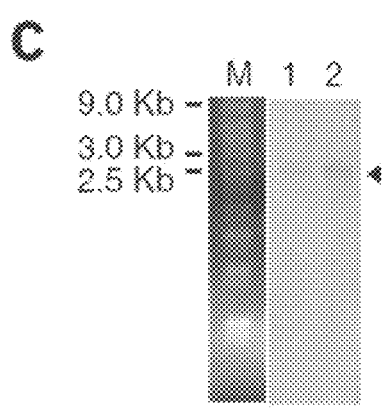
Figure 1D:
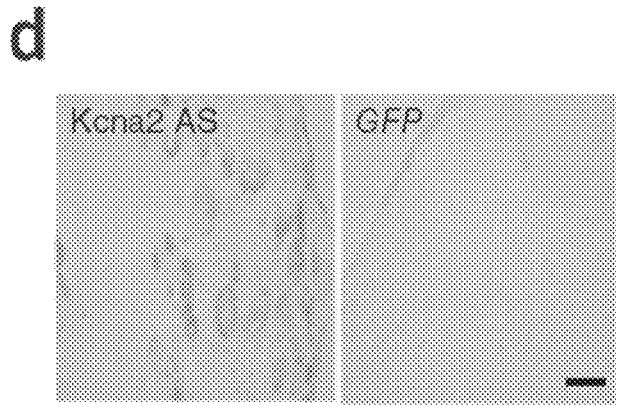
Figure 1E:
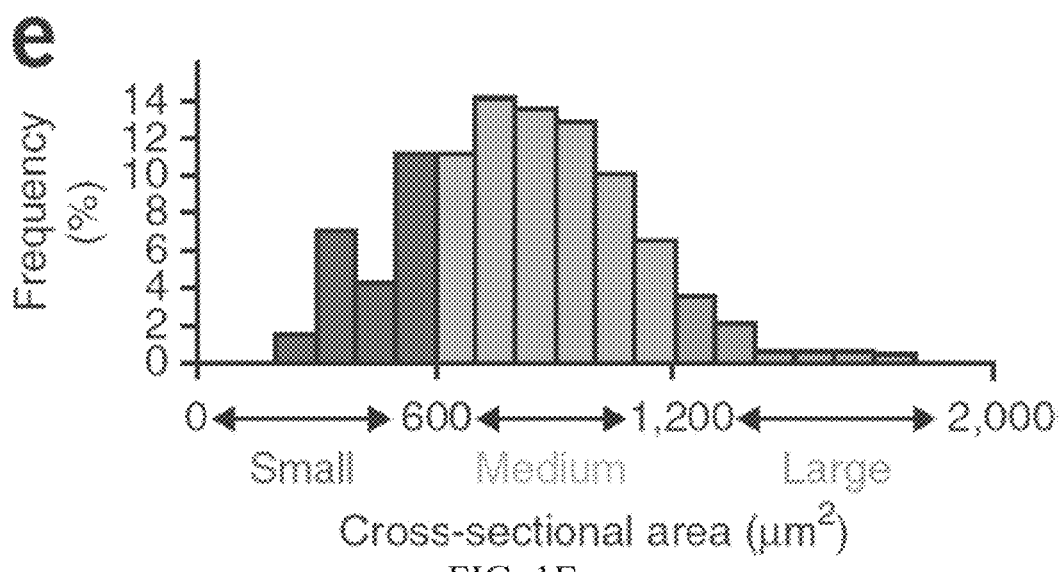
Figure 2:
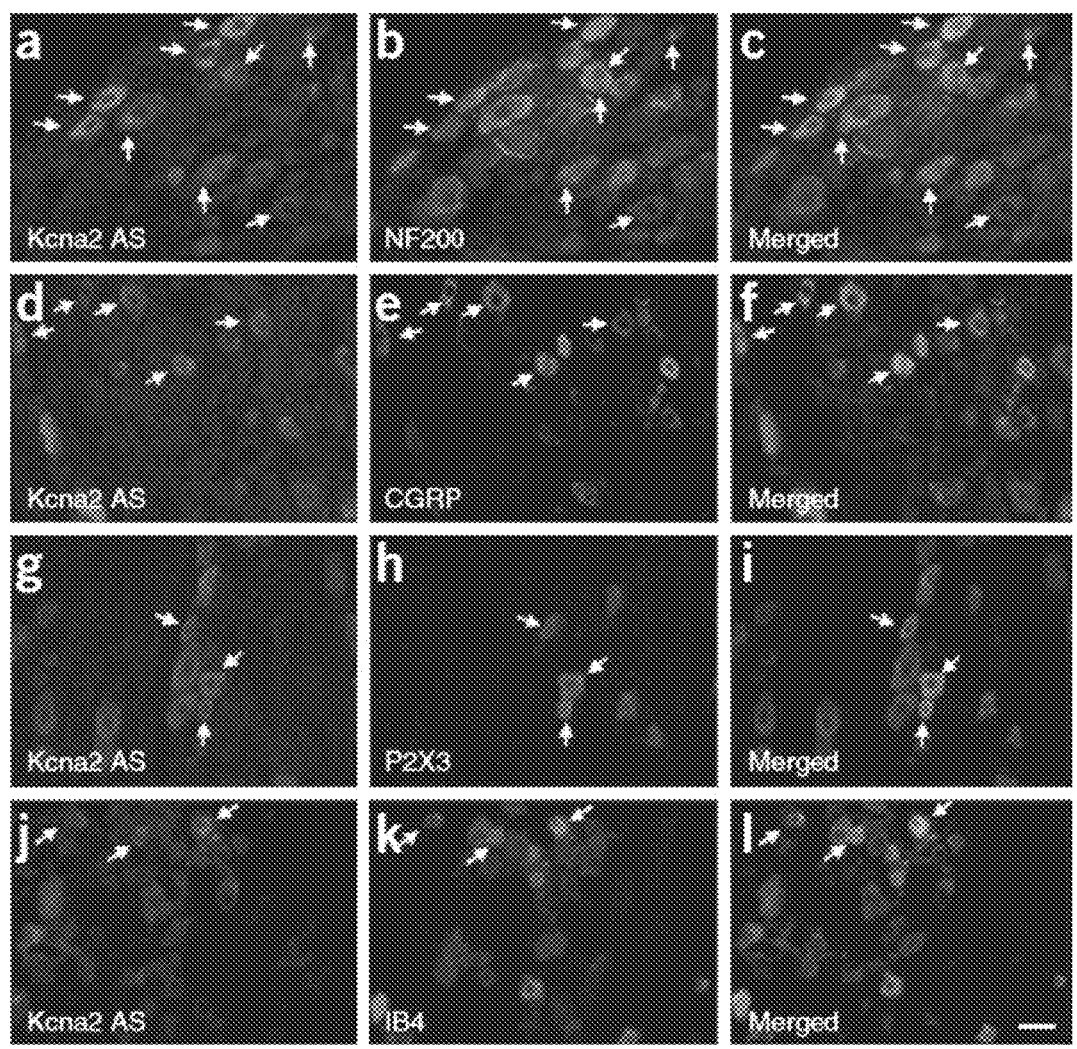
FIG. 2 Subpopulation distribution of Kcna2 antisense RNA-containing neurons in DRG of naive rats. Neurons were double-labeled for Kcna2 antisense (AS) RNA and for neurofilament-200 (NF200; a-c), calcitonin gene-related peptide (CGRP; d-f), P2X3 (g-i) or isolectin B4 (IB4; j-l). Arrows, double-labeled neurons. n=5 rats. Scale bar, 40 µm.
Figure 3:
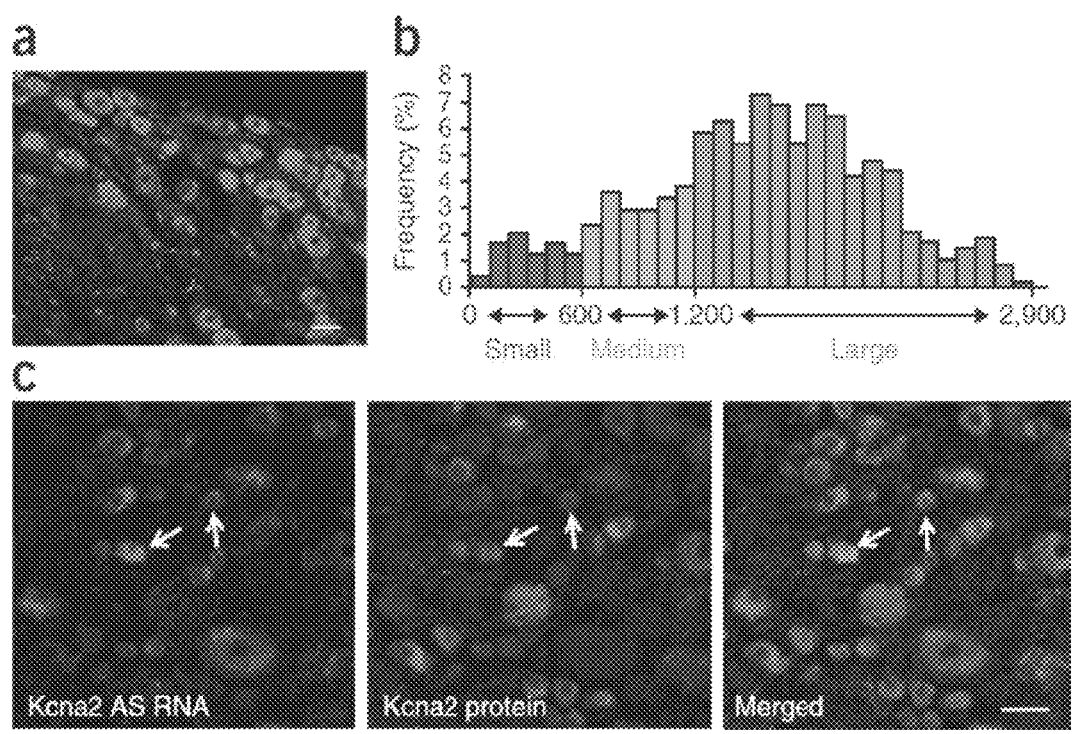
FIG. 3 Distribution of Kcna2 protein and double labeling of Kcna2 antisense RNA with Kcna2 protein in normal rat DRG. (a) A representative example showing the distribution of Kcna2-positive neurons. Approximately 70% (855 of 1,220) of DRG neurons were positive for Kcna2. (b) Distribution of Kcna2-positive somata: large, 72.6%; medium, 18.6%; small, 8.6%. (c) Representative examples showing that most Kcna2 antisense (AS) RNA-labeled neurons in the DRG express low amounts of Kcna2 protein, although a few (arrows) display high-density Kcna2 protein staining. n=5 rats. Scale bars, 50 µm.

We further confirmed the Kcna2 antisense RNA at the expected size by northern blot analysis of RNA from adult rat DRG and spinal cord, although the signals were weak (FIG. 1c). In situ hybridization histochemistry showed that Kcna2 antisense RNA was expressed weakly in DRG neurons (FIG. 1d). Approximately 21.5% of DRG neurons (228 of 1,060) were labeled. Most were medium-sized (69%; 25-35 µm in diameter), although some were small (24%; <25 µm in diameter) and a few large (7%; >35 µm in diameter) (FIG. 1e). Approximately 60.6% of Kcna2 antisense RNA-positive neurons were positive for neurofilament-200 (NF-200) protein, 18.1% for P2X3, 15.3% for isolectin B4 and 28.7% for calcitonin gene-related peptide (CGRP) (FIG. 2). Although the distribution pattern of Kcna2 antisense RNA partially overlapped that of Kcna2 protein in DRG (FIGS. 1e and 3a,b), most Kcna2 antisense RNA-positive neurons express low amounts of Kcna2 protein (FIG. 3c).

Figure 4A:
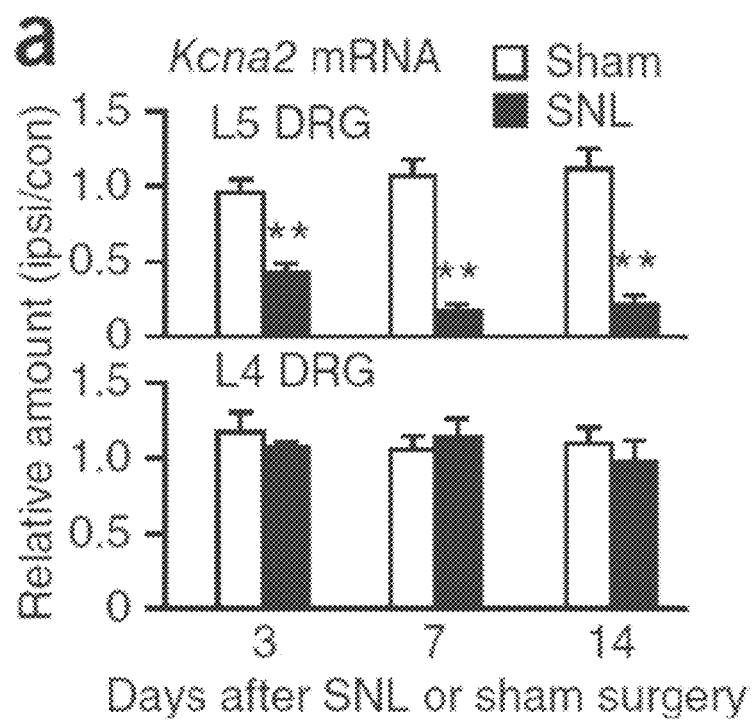
FIG. 4 Changes in expression of DRG Kcna2 antisense RNA and Kcna2 after peripheral nerve injury. (a) Kcna2 mRNA expression in L4/5 DRGs after SNL or sham surgery. Ipsi, ipsilateral; con, contralateral. n=12 rats per group per time point. F=60.05. **P<0.01 versus the sham-operated group at the corresponding time point. Two-way ANOVA with Tukey post-hoc test. (b) Kcna2 protein expression in L5 DRG after SNL or sham surgery. n=12 rats per group per time point. F=6.90 for day 3, 74.11 for day 7 and 351.39 for day 14. *P<0.05, **P<0.01 versus the contralateral side of the sham-operated group at the corresponding time point. Two-way ANOVA with Tukey post-hoc test. Full-length blots are presented in Supplementary FIG. 7. (c) Kcna2 antisense (AS) RNA expression in L4/5 DRGs after SNL or sham surgery. n=12 rats per group per time point. F=35.51. *P<0.05, **P<0.01 versus the sham-operated group at the corresponding time point. Two-way ANOVA with Tukey post-hoc test. (d,e) Kcna2 AS RNA-positive neurons in L5 DRGs after SNL. n=5 rats per time point. F=358.18. *P<0.05, P<0.01 versus the corresponding contralateral side. Scale bars, 40 µm. Two-way ANOVA with Tukey post-hoc test. (f) Histogram; 46.4% of Kcna2 AS RNA-positive neurons are large, 39.1% medium, and 14.5% small in the ipsilateral L5 DRG on day 14 after SNL. (g) Expression of Kcna2 AS RNA and Kcna2 mRNA in L4/5 DRGs on day 7 after axotomy or sham surgery. n=12 rats per group. t=−14.19 for Kcna2 AS RNA and 7.55 for mRNA. P<0.01 versus the corresponding sham-operated group. Paired Student's t-test. (h) The ratios of Kcna2 mRNA to Kcna2 AS RNA in individual DRG neurons on day 7 after SNL or sham surgery. n=15 neurons per cell type per group. t=1.01 for small cells, 3.35 for medium cells and 4.48 for large cells. *P<0.05, **P<0.01 versus the corresponding sham-operated group. Paired Student's t-test. Error bars, s.e.m.3
Figure 4B:
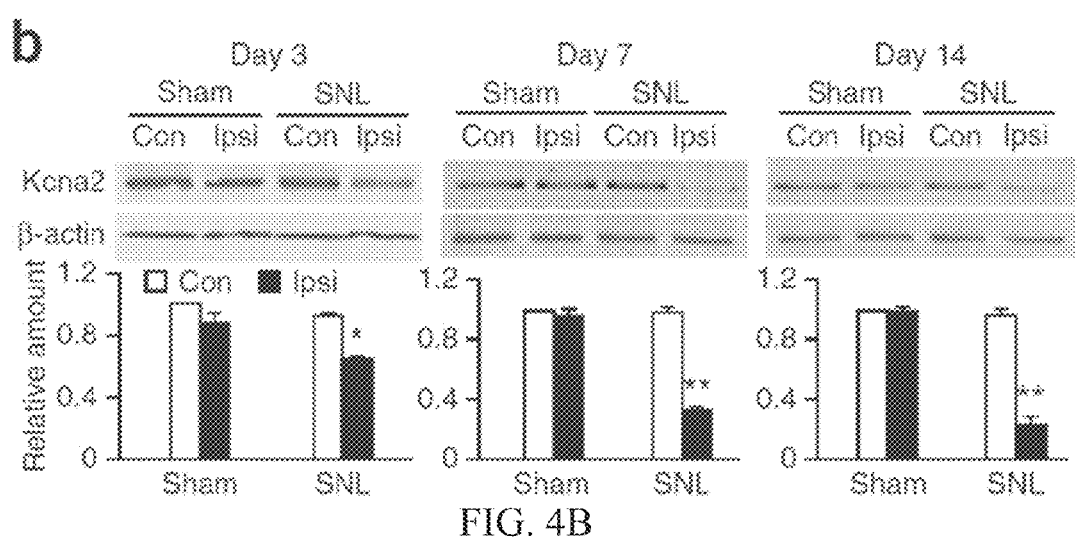
Figure 4C:
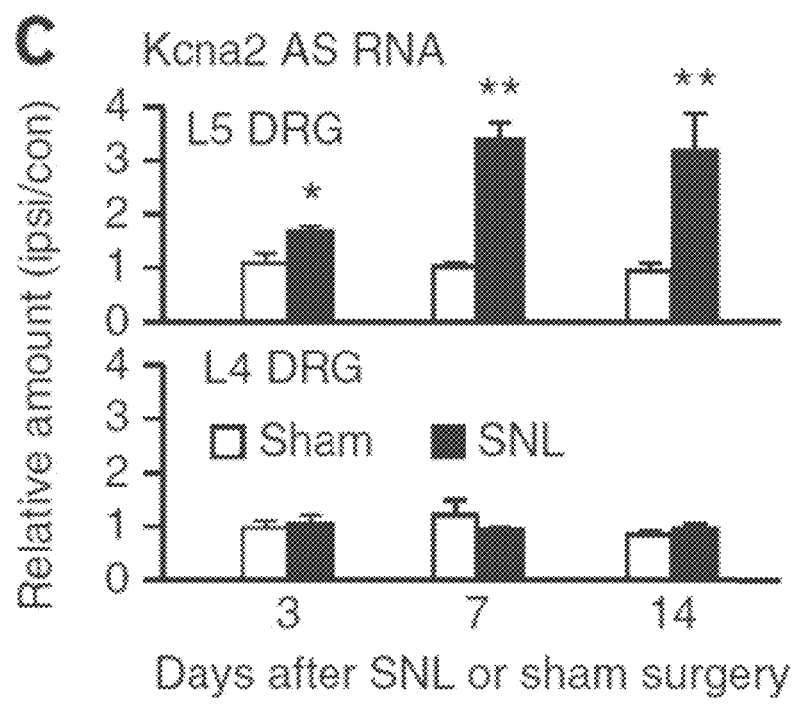
Figure 4D:
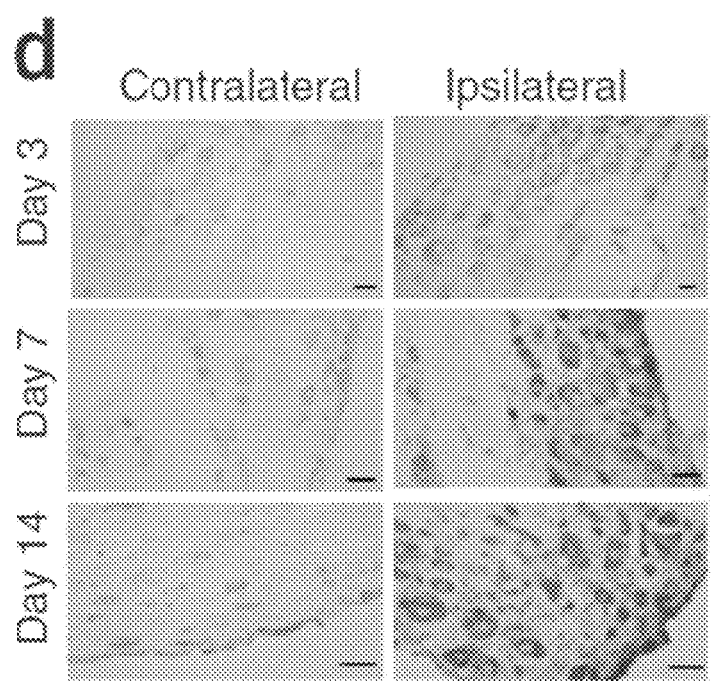
Figure 4E:
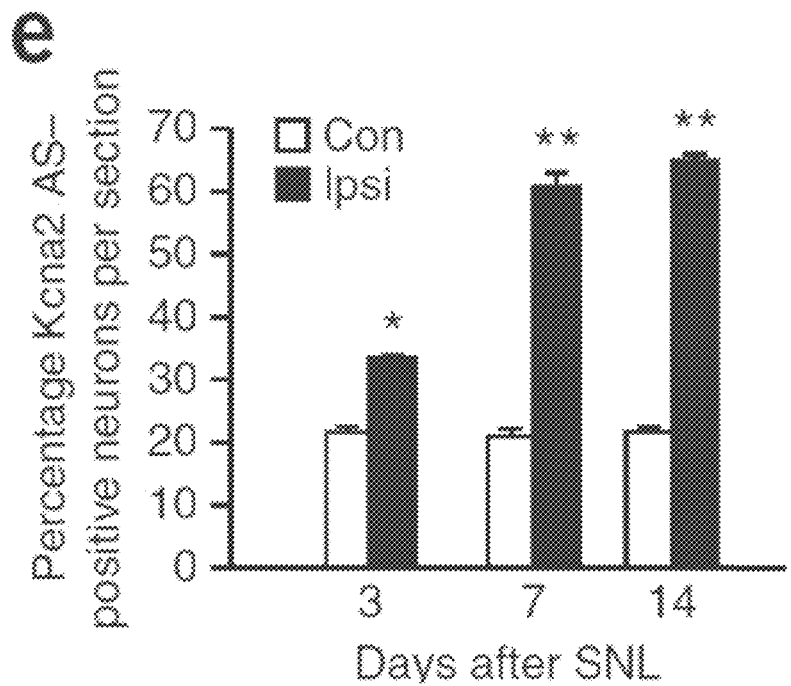
Figure 4F:
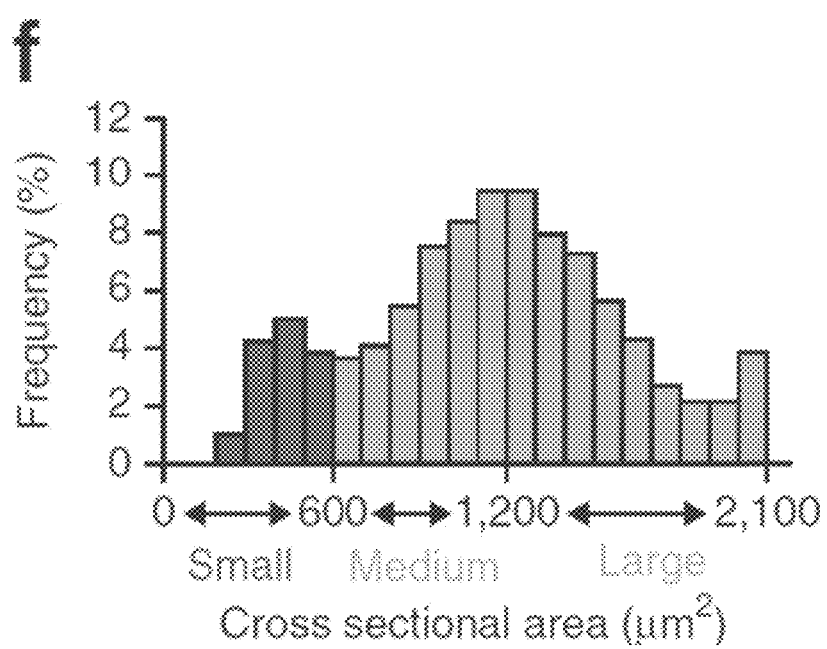
Figure 4G:
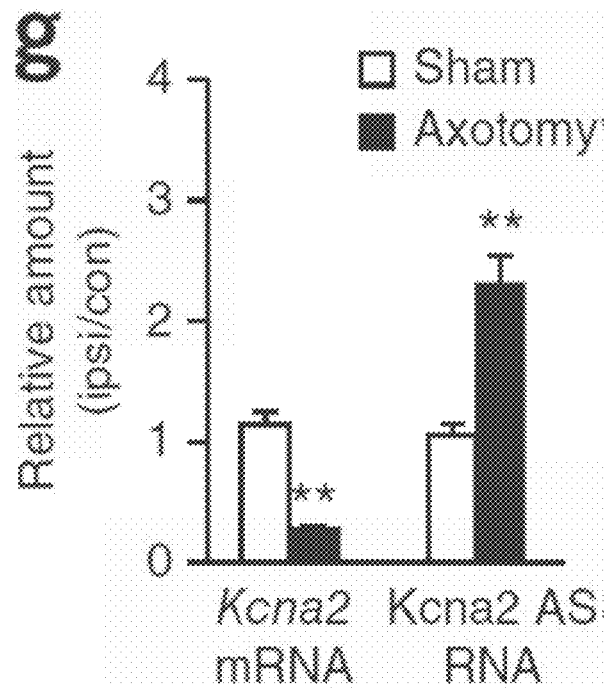
Figure 10A:
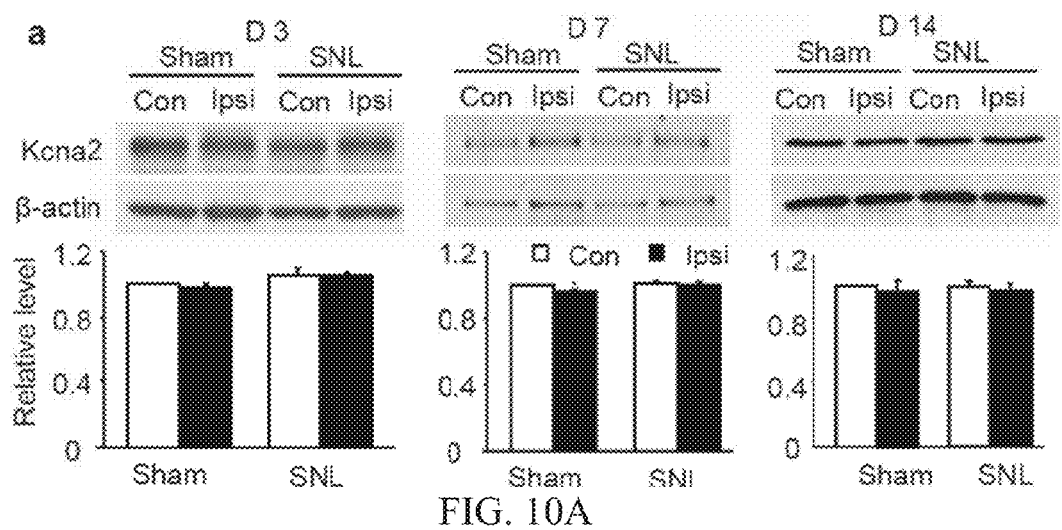
Figure 10B:
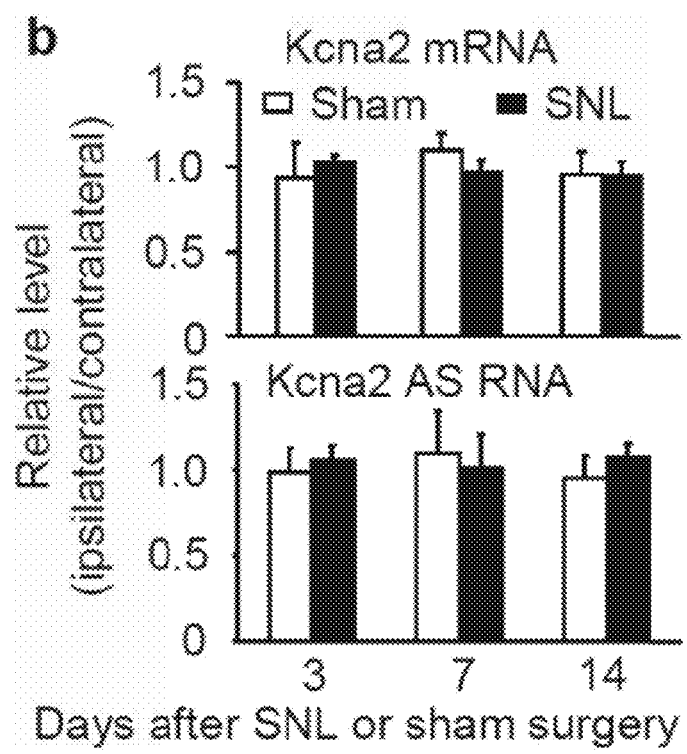
Figure 10C:
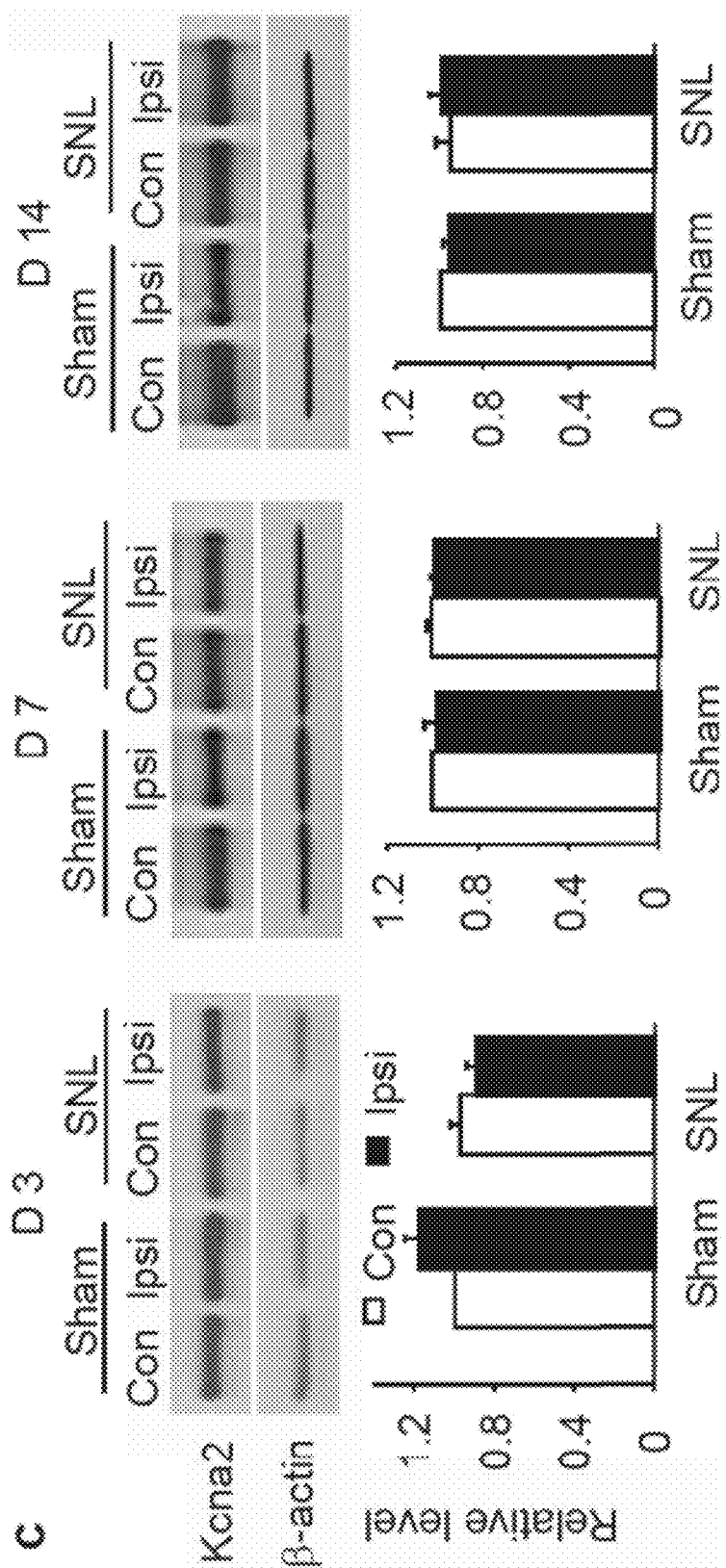
Figure 10D:
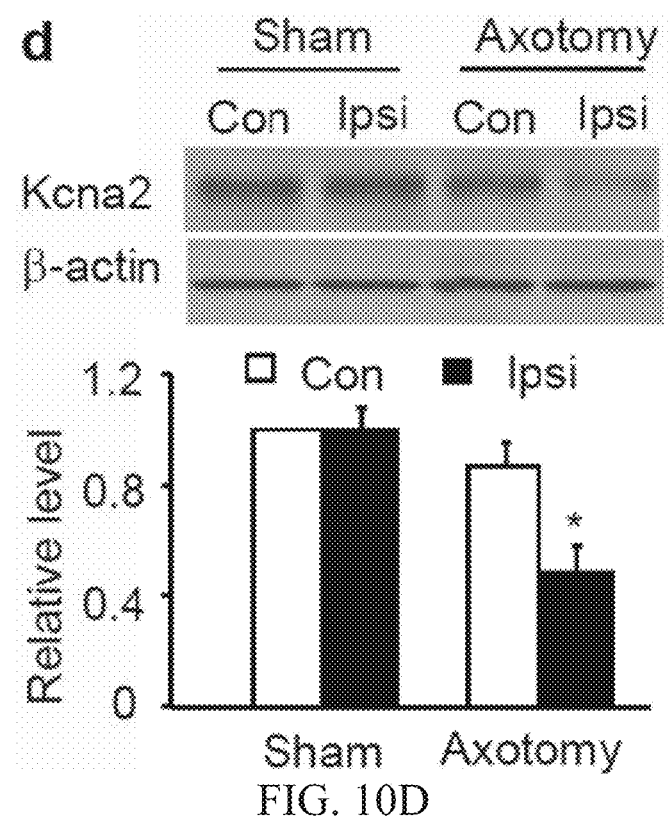

DRG Kcna2 Antisense RNA Expression after Nerve Injury. Next, we examined whether expression of DRG Kcna2 antisense RNA is altered in rat after peripheral nerve injury. Consistent with previous studies5-10, unilateral fifth lumbar (L5) spinal nerve ligation (SNL), but not sham surgery, time-dependently downregulated Kcna2 mRNA (FIG. 4a) and protein (FIG. 4b) in the ipsilateral L5 DRG. Notably, Kcna2 antisense RNA increased time-dependently in the ipsilateral L5 DRG after SNL (FIG. 4c). Neither SNL nor sham surgery changed the expression of Kcna2 mRNA, Kcna2 protein or Kcna2 antisense RNA in the ipsilateral L4 DRG (FIG. 4a,c) or L5 spinal cord (n=4 rats per group per time point, P>0.05; FIG. 10a-c). Furthermore, the staining density and number of Kcna2 antisense RNA-positive neurons in the ipsilateral L5 DRG were higher than those in the contralateral L5 DRG on days 3, 7 and 14 after SNL (FIG. 4d,e). These changes occurred predominantly in large DRG neurons (FIGS. 1e and 4f). Results were similar after sciatic nerve axotomy. On day 7 after axotomy, the ratio of ipsilateral to contralateral Kcna2 antisense RNA was 2.2-fold greater in the injured L5 DRG than in that of the sham-operated groups, whereas the corresponding ratio for Kcna2 mRNA was 75% lower (FIG. 4g). Additionally, Kcna2 protein in the ipsilateral L5 DRG was reduced by 51.8% compared to that in the contralateral L5 DRG from the sham-operated groups (n=12 per group, P<0.05; FIG. 10d).

Figure 4H:
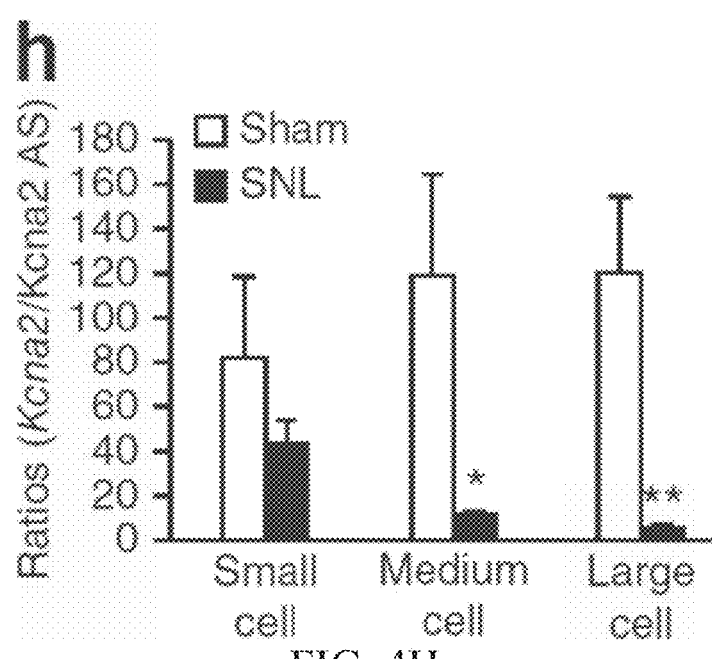

We further examined the opposing SNL-induced changes in Kcna2 antisense RNA and Kcna2 mRNA in individual DRG neurons. Ratios of Kcna2 to Kcna2 antisense RNA were approximately 82, 118 and 121 in small, medium and large DRG neurons, respectively, from sham-operated rats (FIG. 4h). These ratios decreased, particularly in medium and large DRG neurons, 7 d after SNL (FIG. 4h). Taken together, these results demonstrate that Kcna2 antisense RNA can be induced in the injured DRG after peripheral nerve injury.

Figure 5A:
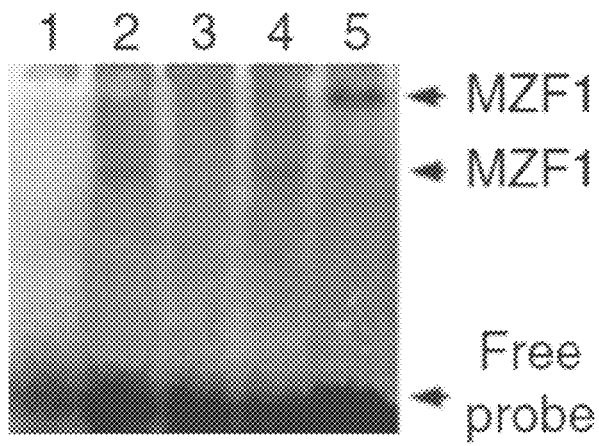
FIG. 5 MZF1 mediates nerve injury-induced upregulation of DRG Kcna2 antisense RNA. (a) Electrophoretic mobility shift assay showing binding specificity of MZF1 for the Kcna2 antisense promoter. Labeled probe alone (lane 1) or plus nuclear extract (lane 2), nuclear extract and 50-fold unlabeled probe (lane 3), nuclear extract and 50-fold unlabeled mutant probe (lane 4), or nuclear extract and antibody to MZF1 (lane 5). n=3 repeats. (b) Kcna2 antisense (AS) promoter fragments immunoprecipitated by rabbit antibody to MZF1 in the ipsilateral L5 DRGs on day 14 after SNL or sham surgery. Input, total purified fragments. M, ladder marker. (c,d) MZF1expression in the ipsilateral L5 DRGs after SNL or sham surgery. Histone H3 (H3) serves as a loading control. n=9 rats per time point per group. F=14.13. *P<0.05 versus the corresponding naive group (day 0). One-way ANOVA with Tukey post-hoc test. (e,f) Amounts of Kcna2 AS RNA (e), Kcna2 mRNA (e) and Kcna2 protein (f) in HEK-293T cells transfected as shown. Ctl, EGFP control; siRNA, Mzf1 siRNA; Scram, scrambled Mzf1 siRNA. n=5 repeats per treatment. F=8.53 for AS RNA, 12.92 for mRNA and 7.93 for protein. *P<0.05, **P<0.01 versus EGFP control. #P<0.05, ##P<0.01 versus Mzf1 alone. One-way ANOVA with Tukey post-hoc test. (g) Amounts of Mzf1 mRNA, Kcna2 AS RNA and Kcna2 mRNA in rat DRG cultured neurons transduced as shown. Inset, an AAV5-EGFP-labeled neuron. n=3 repeats per treatment. F=168.61 for Mzf1 mRNA, 30.84 for Kcna2 AS RNA and 17.79 for Kcna2 mRNA. *P<0.05, P<0.01 versus the corresponding naive condition. #P<0.05 versus the corresponding AAV5-MZF1 alone. Two-way ANOVA with Tukey post-hoc test. (h) Kcna2 gene promoter and Kcna2 AS gene promoter activities in HEK-293T cells transfected as shown. Vec, control vector (pGL3-Basic). n=3 repeats per treatment. F=82.09. P<0.01 versus pGL3-Kcna2 AS vector alone. One-way ANOVA with Tukey post-hoc test. Error bars, s.e.m. Full-length blots are presented in Supplementary FIG. 7.
Figure 5B:
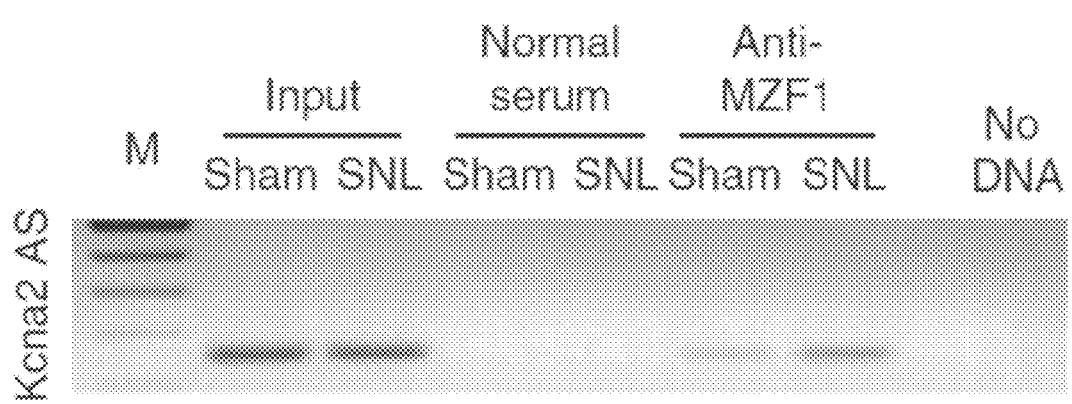
Figure 5C:
Figure 5D:
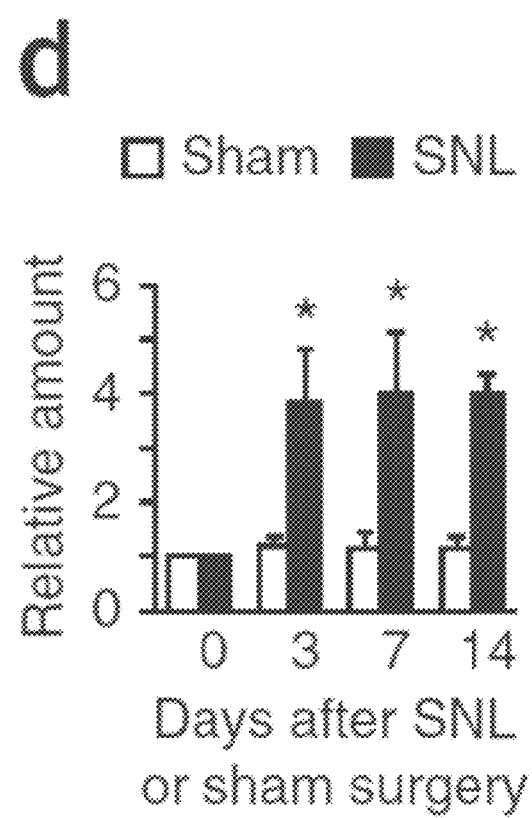
Figure 11A:
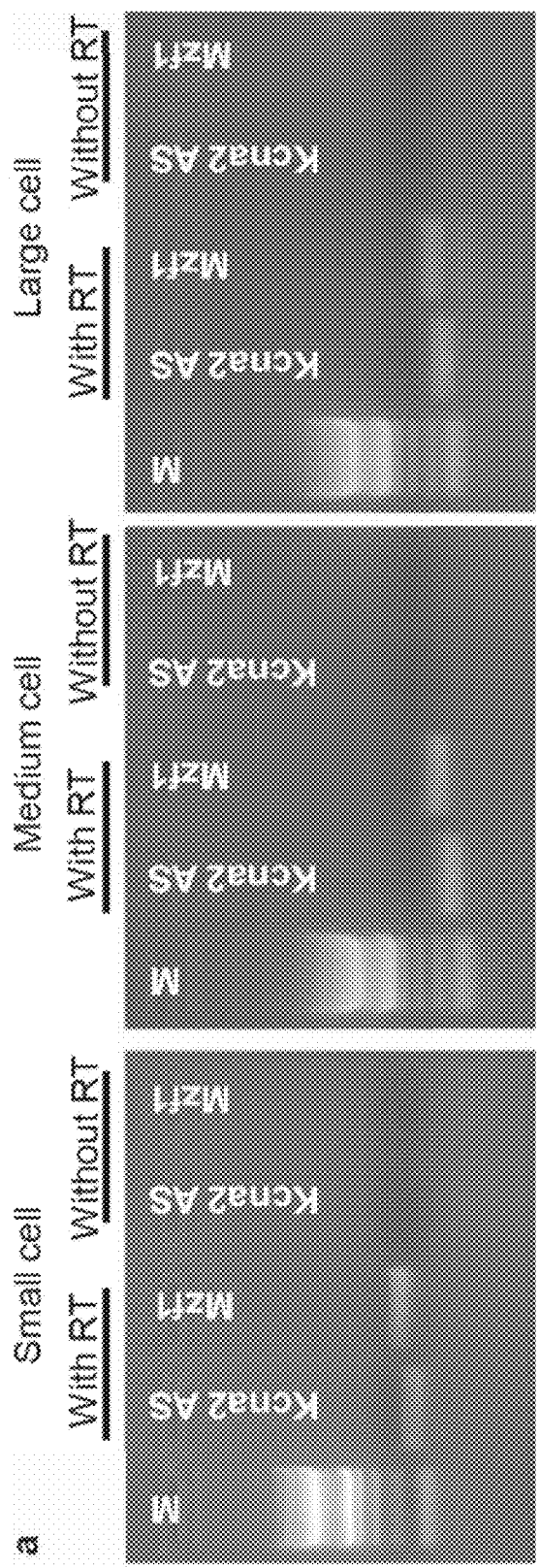
Figure 11B:
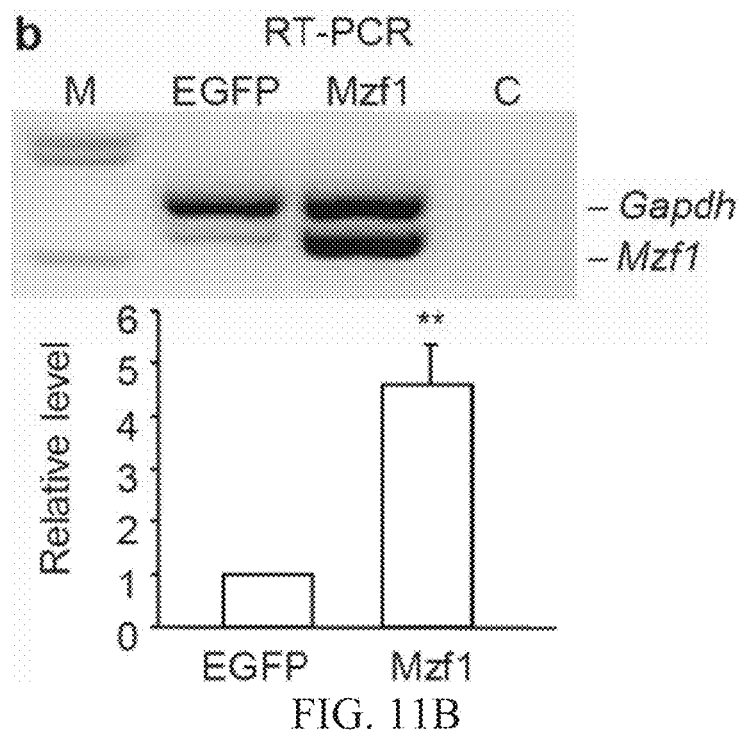
Figure 11C:
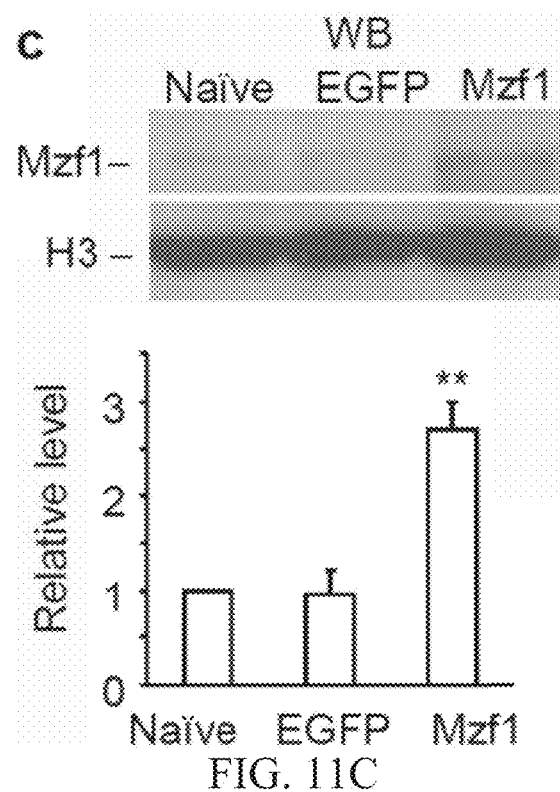
Figure 11D:
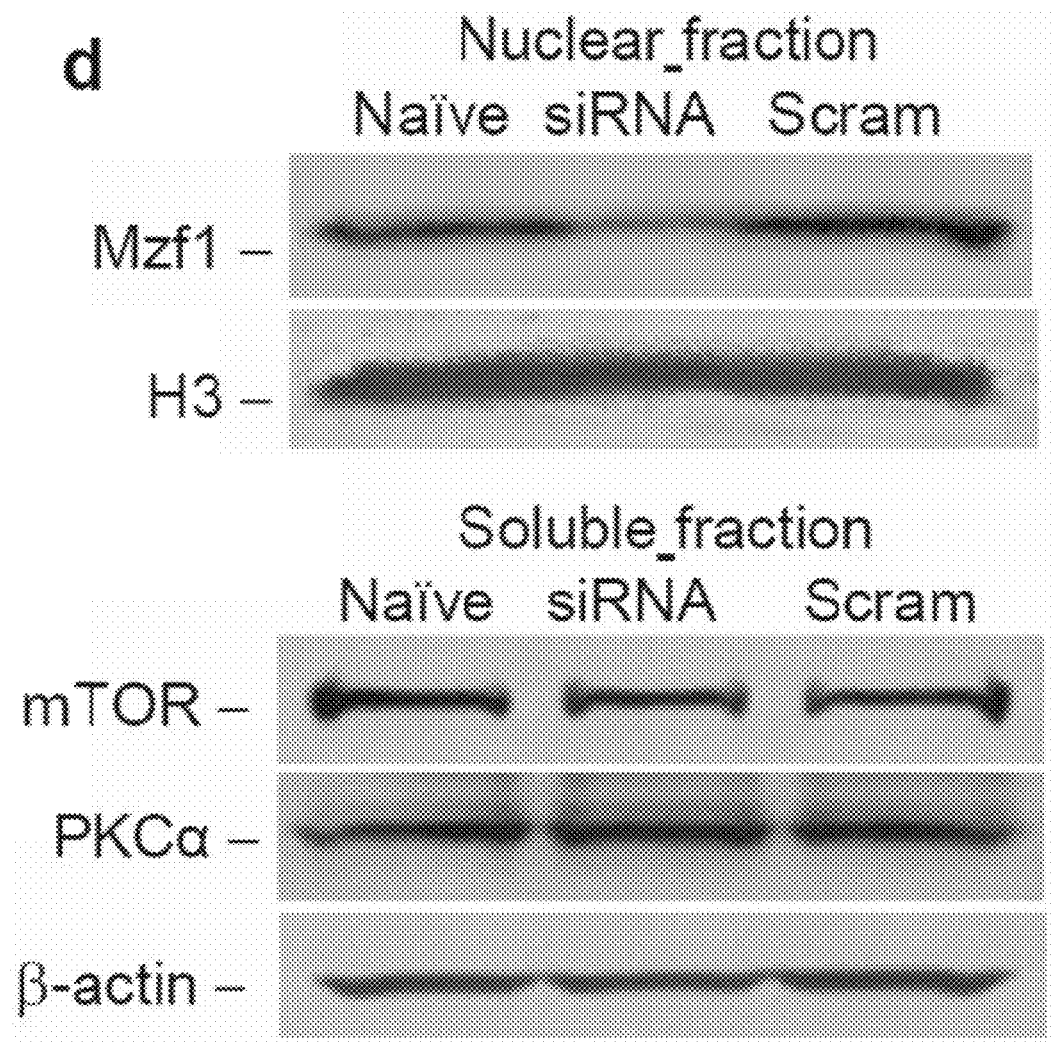

MZF1 Promotes Kcna2 Antisense RNA Gene Activity after SNL. How is DRG Kcna2 antisense RNA upregulated after nerve injury? Using the online software TFSEARCH, we found a consensus binding motif (−161AGTGGGGA-154) for the transcriptional activator myeloid zinc finger protein 1 (MZF1) in the promoter region of the Kcna2 antisense RNA gene[20,21]. An electrophoretic mobility shift assay demonstrated binding of MZF1 to this motif in the DRG (FIG. 5a). A chromatin immunoprecipitation assay revealed that a fragment of the Kcna2 antisense RNA promoter that includes the binding motif could be amplified from the complex immunoprecipitated with MZF1 antibody in nuclear fractions from DRGs in sham-operated rats (FIG. 5b). This amplification did not occur with normal serum (FIG. 5b) or after preabsorption of MZF1 antibody (data not shown), indicating that the binding of MZF1 to the Kcna2 antisense RNA promoter is specific and selective. SNL increased the binding of MZF1 to the Kcna2 antisense gene promoter, as demonstrated by a 4.12-fold greater band density in the ipsilateral L5 DRG from SNL rats compared to that from sham-operated rats on day 14 (n=6 rats per group, P<0.05). This increase may result from SNL-induced time-dependent upregulation of MZF1 in the ipsilateral L5 DRG (FIG. 5c,d). As expected, neither sham nor SNL surgery altered basal binding activity or MZF1 expression in the contralateral L5 DRG and ipsilateral L4 DRG (data not shown). Moreover, Mzf1 mRNA was expressed with Kcna2 antisense RNA in the DRG neurons (FIG. 11a). These in vivo findings suggest that peripheral nerve injury increases DRG MZF1 expression, allowing the binding of more MZF1 to the promoter region of Kcna2 antisense gene in the injured DRG neurons.

Figure 5E:
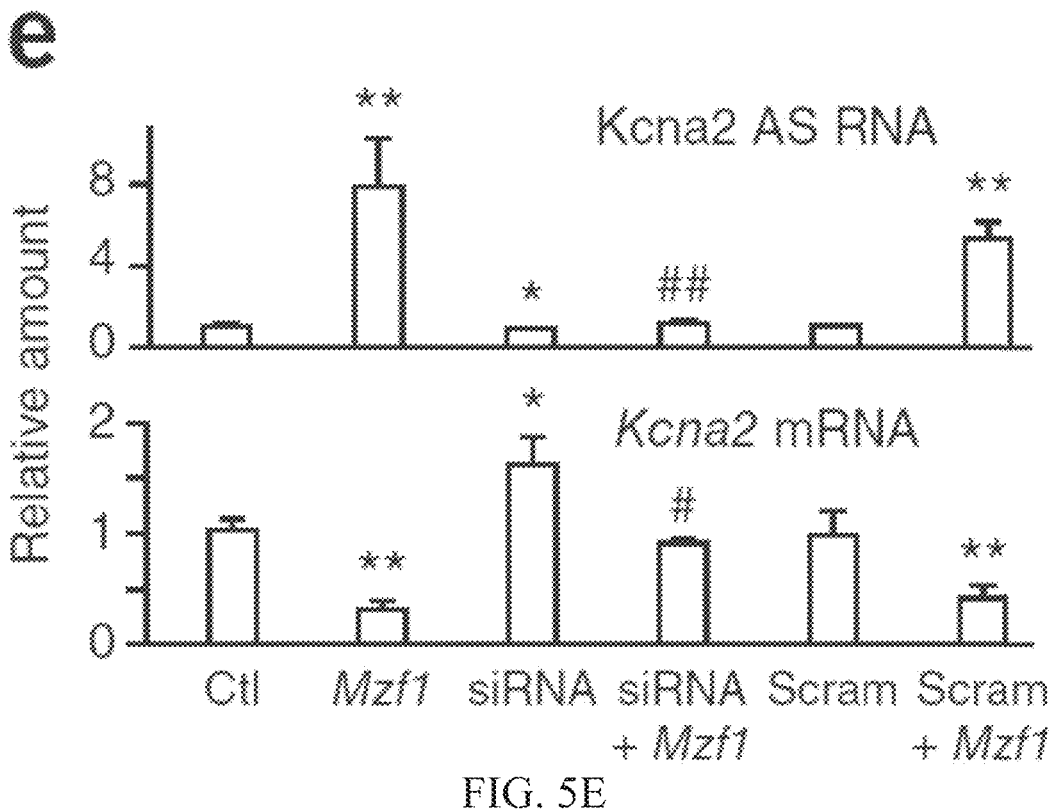
Figure 5F:
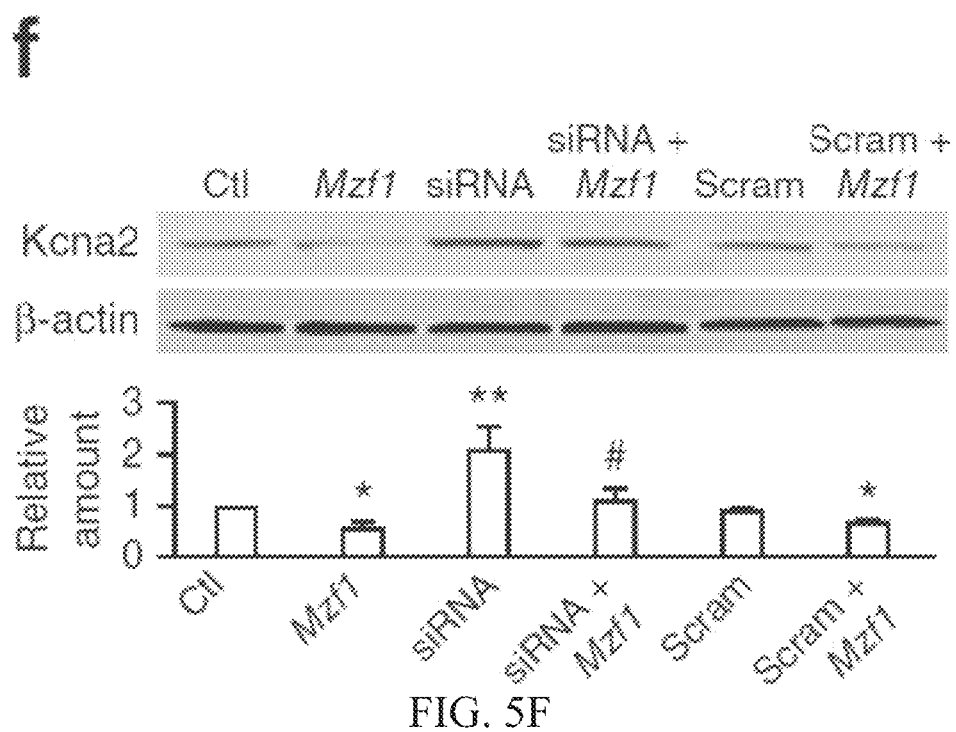
Figure 5G:
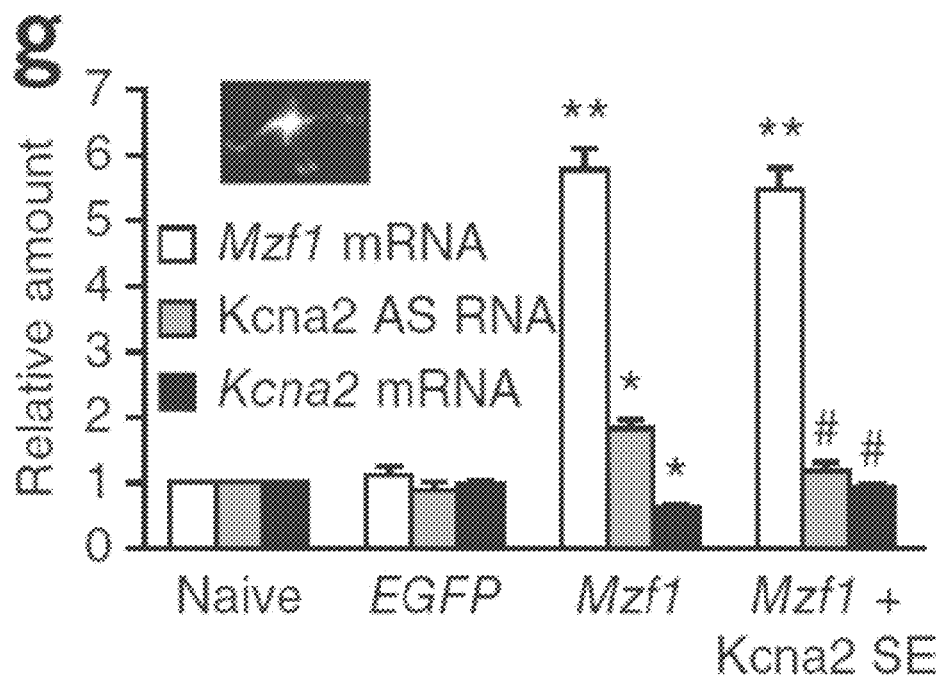

To further examine whether MZF1 directly regulates Kcna2 antisense RNA expression, we overexpressed full-length Mzf1 in cultured human embryonic kidney (HEK)-293T cells (FIG. 11b,c), which express endogenous Kcna2 antisense RNA, Kcna2 and other voltage-gated potassium channels. MZF1 overexpression significantly increased Kcna2 antisense RNA and correspondingly decreased Kcna2 mRNA and Kcna2 protein (FIG. 5e,f). These responses were abolished in cells co-transfected with full-length Mzf1 vector and Mzf1-specific short interfering RNA (but not scrambled Mzf1 siRNA) (FIG. 5e,f and FIG. 11d), indicating that upregulation of Kcna2 antisense RNA was specific in response to MZF1. Mzf1 siRNA transfection alone also reduced basal Kcna2 antisense RNA expression and increased basal expression of Kcna2 mRNA and protein (FIG. 5e,f). We confirmed MZF1-triggered upregulation of Kcna2 antisense RNA and downregulation of Kcna2 mRNA in cultured DRG neurons that were transduced with recombinant adeno-associated virus 5 (AAV5) that expressed full-length Mzf1 (FIG. 5g).

Figure 5H:
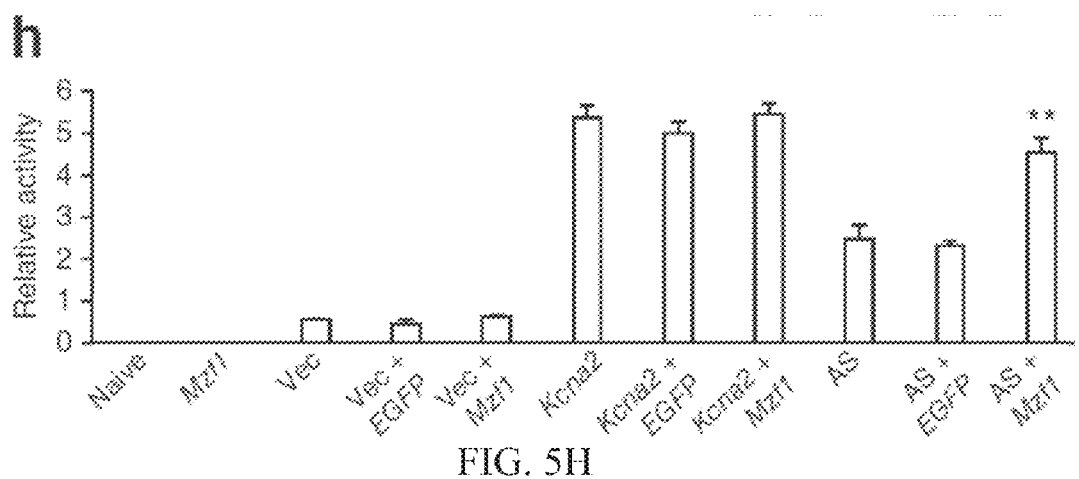
Figure 6A:
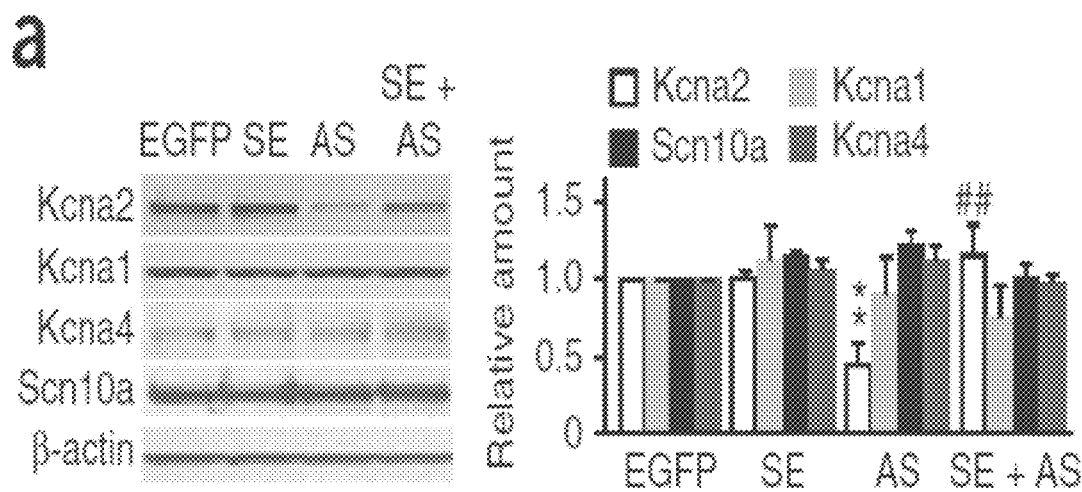
Figure 6B:
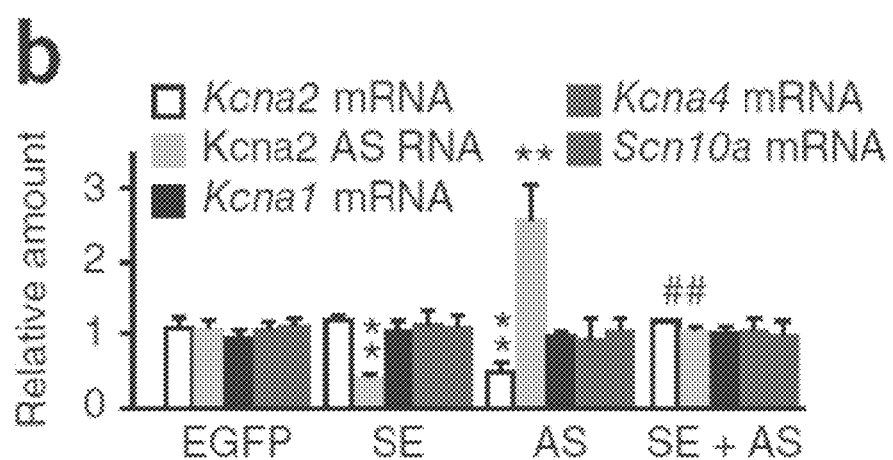

A software prediction showed that the promoter region of the Kcna2 gene does not contain a consensus MZF1-binding motif. MZF1 does not enhance the activity of the Kcna2 gene promoter, but it markedly activates the Kcna2 antisense gene promoter (FIG. 5h). In naive rats, Kcna2 gene promoter fragments were not amplified from the DRG nuclear complex immunoprecipitated by MZF1 antibody (data not shown). MZF1-triggered downregulation of Kcna2 is thus not likely to occur by direct binding of MZF1 to the Kcna2 gene promoter. To examine whether Kcna2 antisense RNA mediates this effect, we cloned an AAV5 vector that expresses a Kcna2 sense RNA fragment (−311 to +40). This fragment significantly blocked Kcna2 antisense RNA expression (FIG. 6a,b) but did not alter basal expression of Kcna2 mRNA or Kcna2 protein or produce truncated Kcna2 protein in cultured HEK-293T cells or DRG neurons (FIG. 6a,b). We found that the Kcna2 sense fragment blocked the MZF1-induced increase in Kcna2 antisense RNA and reversed the MZF1-induced reduction in Kcna2 mRNA in DRG neurons (FIG. 5g). Thus, MZF1-induced Kcna2 downregulation may be attributable to MZF1-triggered Kcna2 antisense gene expression.

Figure 6C:
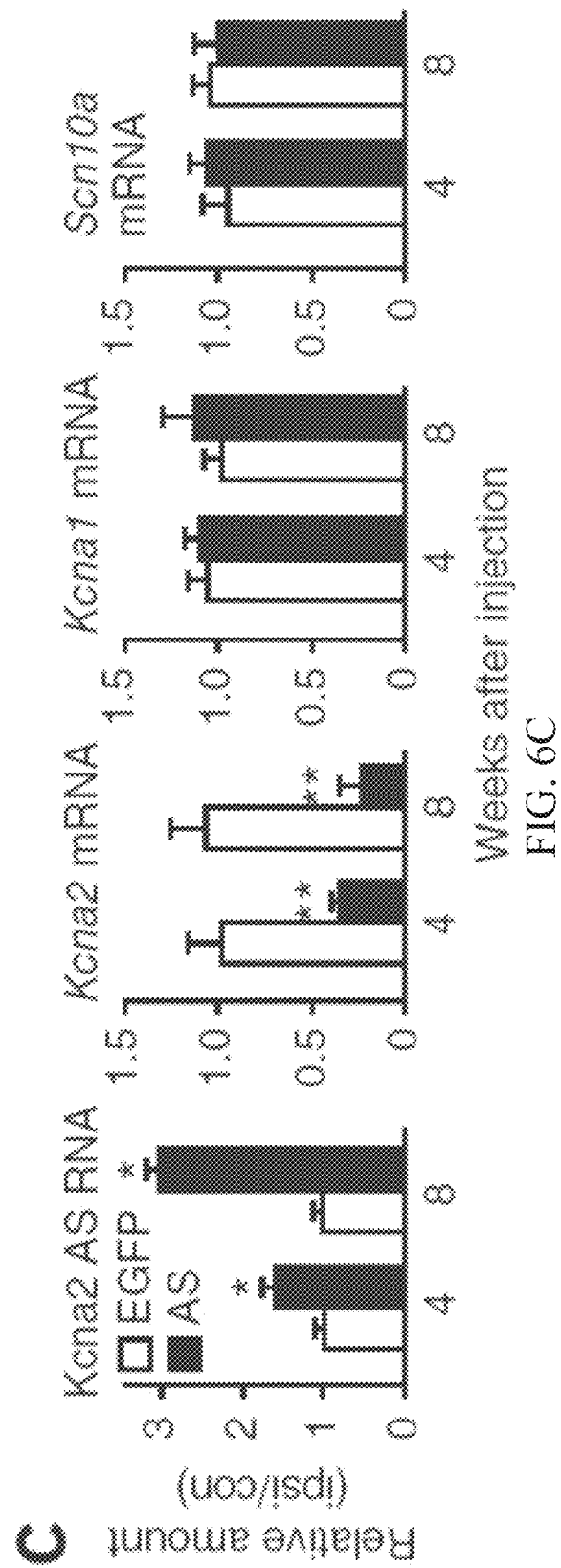
Figures 6D, 6E:
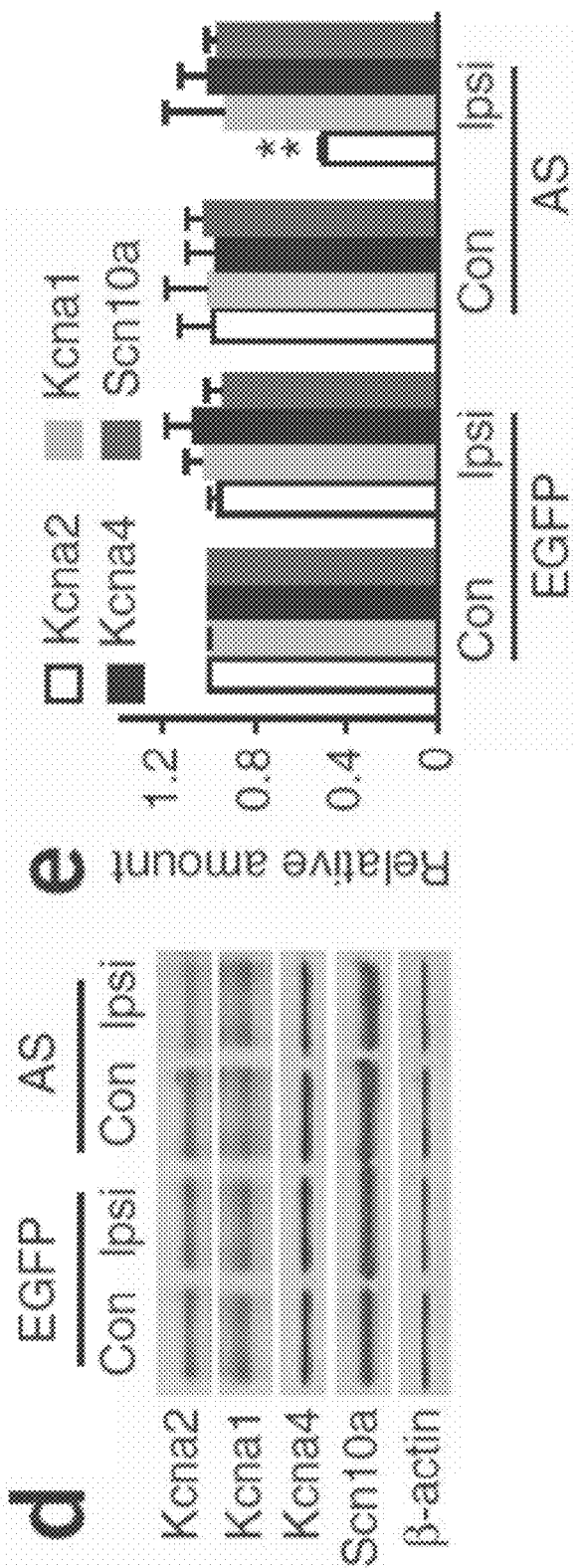

DRG Kcna2 Antisense RNA Leads to Neuropathic Pain Symptoms. We next investigated whether mimicking nerve injury-induced upregulation of DRG Kcna2 antisense RNA alters DRG Kcna2 expression and function, DRG neuronal excitability and nociceptive thresholds. To this end, we transfected Kcna2 antisense RNA proviral vector or control EGFP vector into cultured HEK-293T cells and transduced AAV5 that expressed Kcna2 antisense RNA (AAV5-Kcna2 antisense) or EGFP (AAV5-EGFP) into cultured DRG neurons. Kcna2 antisense RNA markedly decreased Kcna2 mRNA and protein expression, but not Kcna1, Kcna4 or Scn10a expression (FIG. 6a,b). Then we injected AAV5-Kcna2 antisense or AAV5-EGFP unilaterally into the L4 and L5 (L4/5) DRGs. Four weeks after injection, EGFP-labeled AAV5 was limited to the ipsilateral L4/5 DRG neurons and their fibers and terminals (FIG. 12a-g). Approximately 87.1% of labeled cells were positive for NF-200, 4.21% for substance P, 6.32% for CGRP and 10.0% for P2X3 (FIG. 12h), a distribution similar to that of Kcna2 antisense RNA-positive neurons in the injured DRG after SNL (FIG. 4f). Expression of the Kcna2 antisense RNA was significantly increased in the L4/5 DRGs at 4 weeks, reached a peak at 8 weeks and remained high for at least 12 weeks after viral injection (FIG. 6c). In contrast, the expression of Kcna2 mRNA and protein was significantly and temporally reduced in the ipsilateral L4/5 DRGs (FIG. 6c-e). The amounts of mRNA and protein of Kcna1, Kcna4 or Scn10a were unaffected (FIG. 6c-e). These results indicate that Kcna2 antisense RNA specifically and selectively targets Kcna2.

Figures 13D, 13E, 13F:
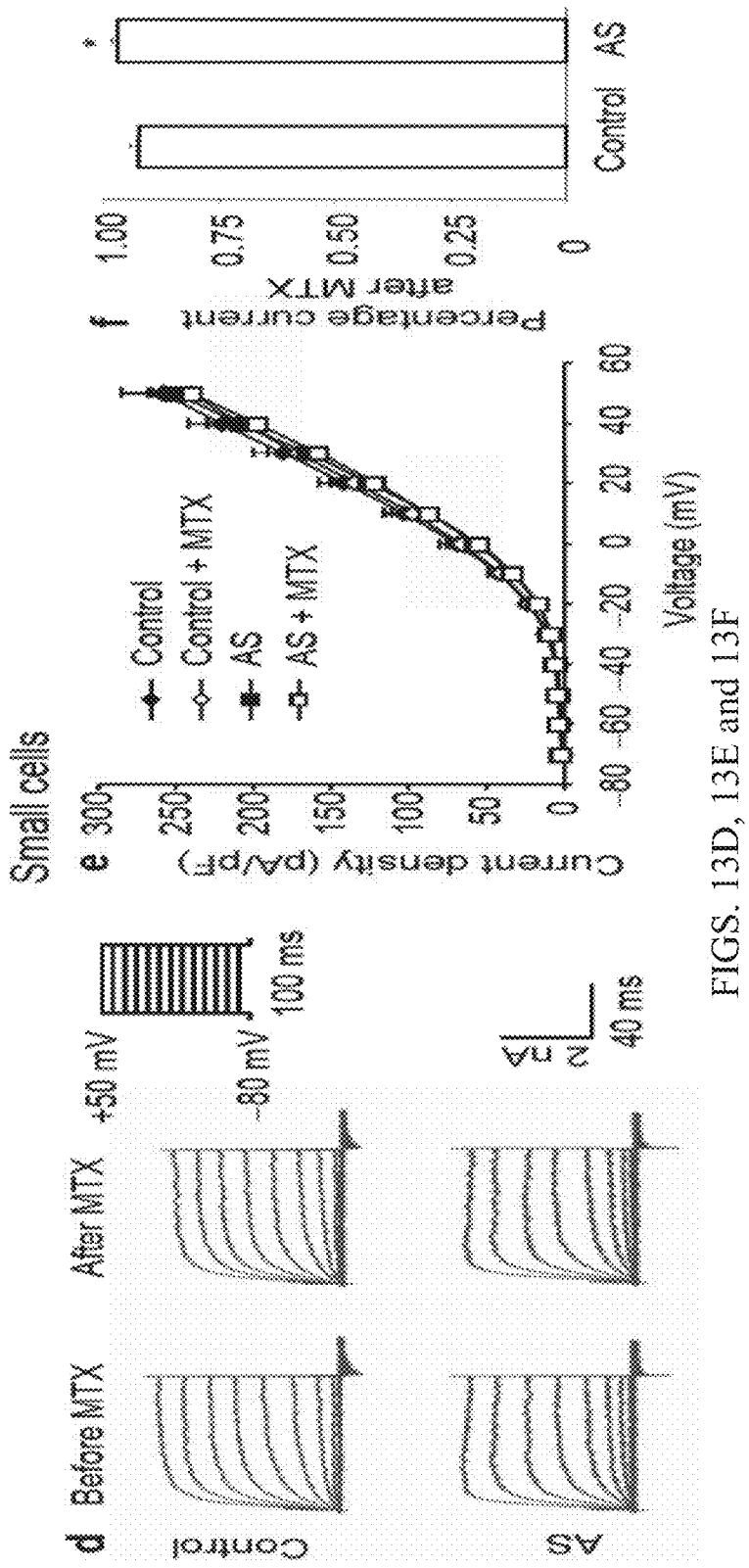
Figure 14A:
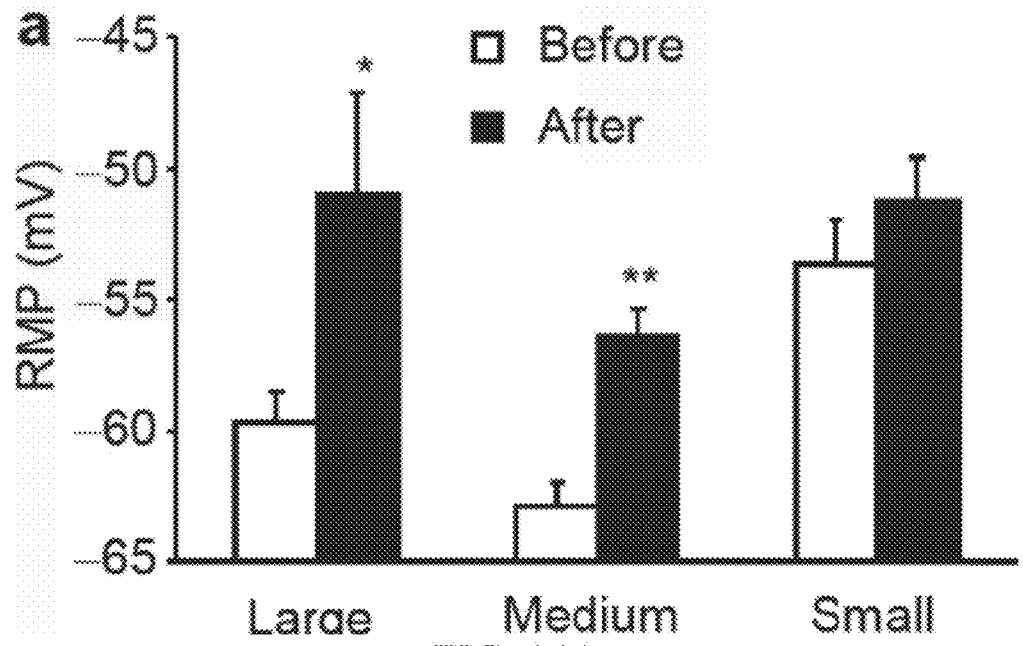
Figure 14B:
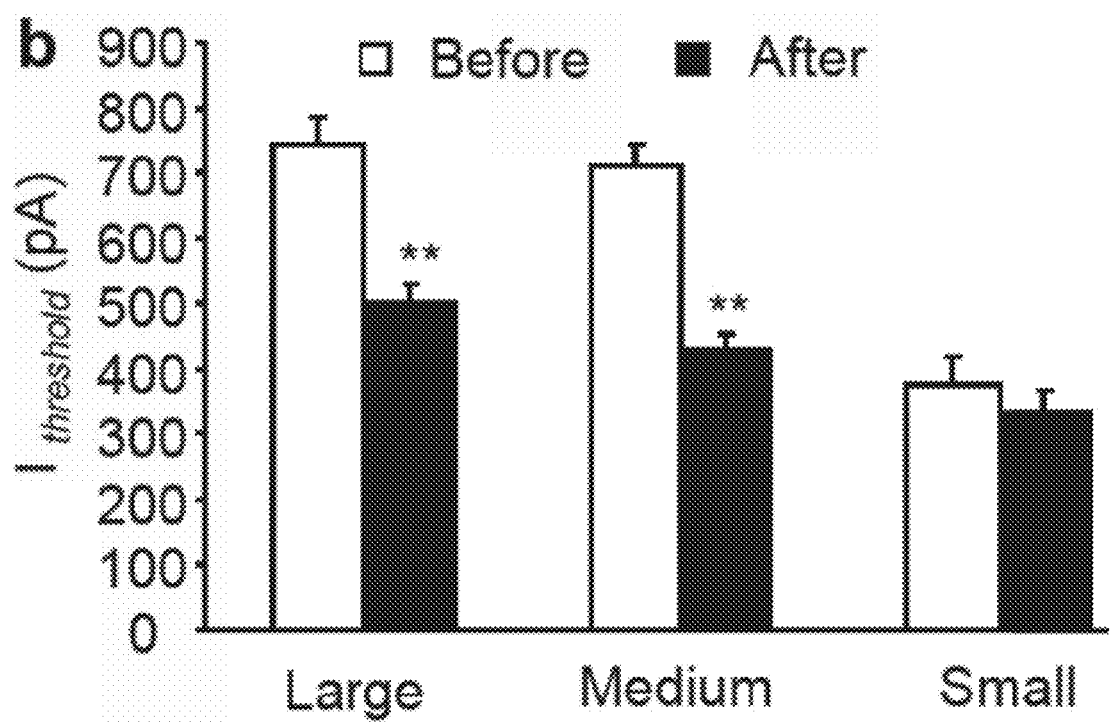
Figure 14C:
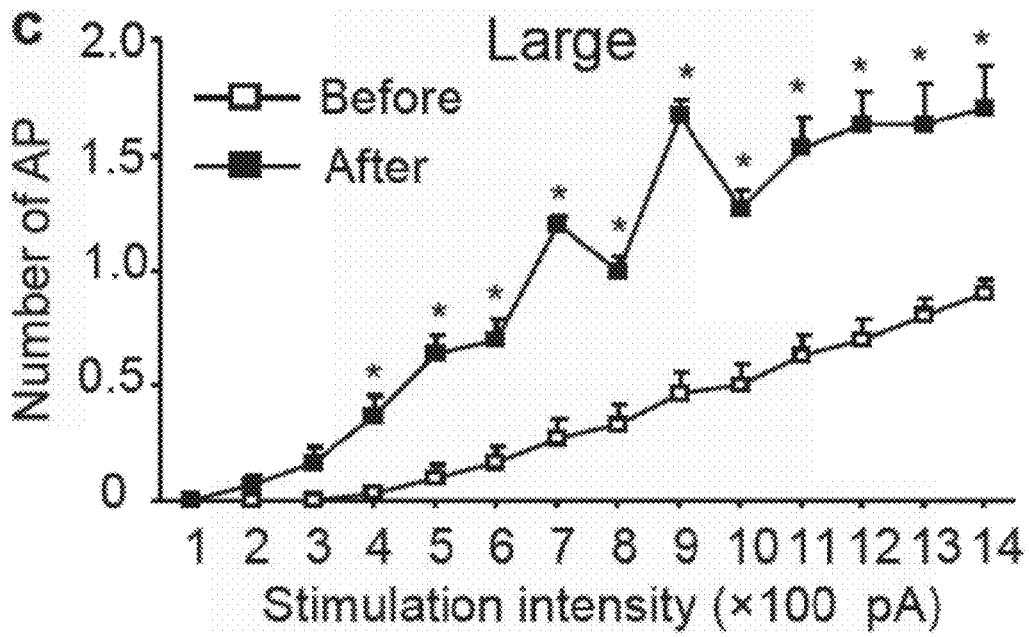
Figure 14D:
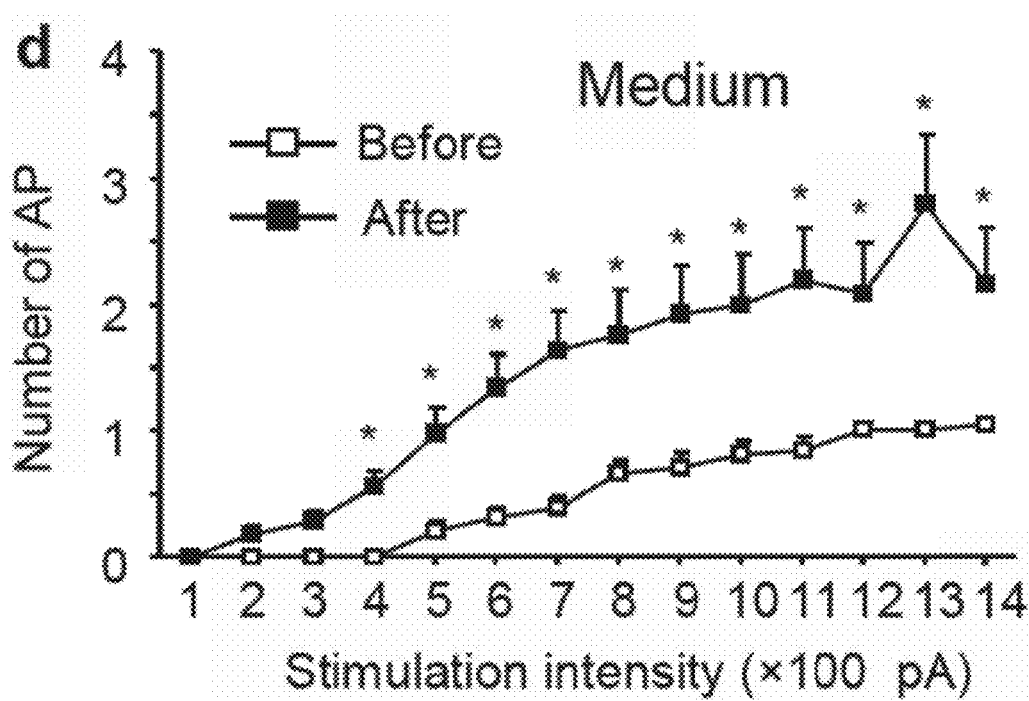
Figure 14E:
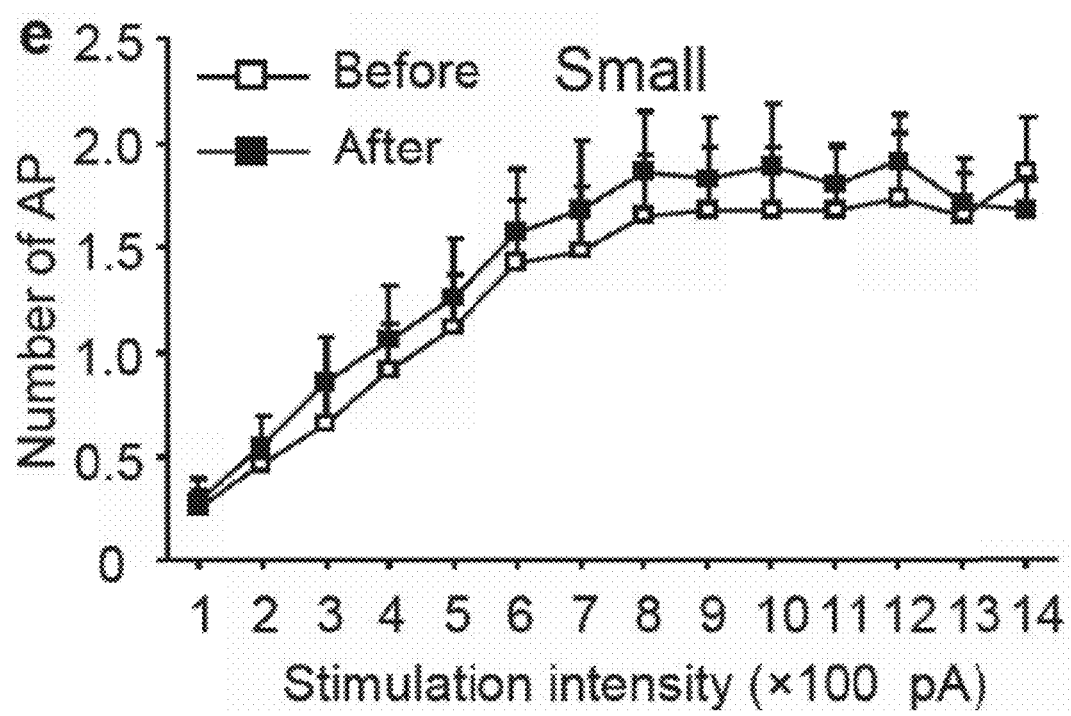

Using a voltage-clamp technique, we recorded Kcna2-related current in neurons freshly dissociated from the injected L4/5 DRGs 8-12 weeks after injection. To increase the recording efficiency, we injected AAV5-EGFP alone (control group) or a mixed viral solution of AAV5-Kcna2 antisense plus AAV5-EGFP (Kcna2 antisense-treated group) and recorded only green DRG neurons (FIG. 7a). In the Kcna2 antisense-treated group, total voltage-gated potassium current density was significantly lower in large- and medium-diameter neurons (FIG. 7a,b and FIG. 13a-c). To verify whether this reduction was due to Kcna2 downregulation, we used bath application of 100 nM maurotoxin (MTX), a selective Kcna2 current inhibitor 22-24. MTX produced greater reductions in total voltage-gated potassium current in large (n=14 per group) and medium (control: n=17; antisense, n=15) neurons from the control group than in those from the Kcna2 antisense-treated group at depolarized voltages (P<0.05 or 0.01; FIG. 7a,b and FIG. 13a-c). When tested at +50 mV, large and medium neurons in the control group retained 81.7±1.7% and 85.1±2.2% of current, respectively, after MTX treatment, but large and medium neurons from the Kcna2 antisense-treated group retained 92.3±0.9% and 94.9±1.6% of current, respectively. In small DRG neurons, the current reduction by MTX was less prominent, but the difference between control and Kcna2 antisense-treated groups was still significant (n=11 neurons per group, P<0.05; FIG. 13d-f). These data indicate that Kcna2 antisense RNA reduces total voltage-gated potassium current densities in large and medium DRG neurons and decreases Kcna2-related current in all DRG neurons.

To assess whether Kcna2 antisense RNA modulates DRG neuronal excitability, we carried out whole-cell current-clamp recording 8-12 weeks after injection. Compared to the control group, Kcna2 antisense RNA treatment significantly increased resting membrane potentials, by 6.74 mV and 10.52 mV in large and medium neurons, respectively (FIG. 7c), and reduced current thresholds by 217 pA and 344 pA, respectively (P<0.01; FIG. 7d). The average number of action potentials evoked by stimulation of ≥300 pA in the Kcna2 antisense-treated group was greater than the average number evoked by the corresponding stimulation intensity in the control group in large and medium neurons (FIG. 7e-g). No such changes were observed in small DRG neurons (FIG. 7c,d,h). There were no apparent differences between the two groups in membrane input resistances or other action potential parameters, such as amplitude, threshold, duration, overshoot and after-hyperpolarization amplitude (Supplementary Table 1). Application of MTX into DRG neurons produced similar effects (FIG. 14 and Supplementary Table 1). Our findings indicate that Kcna2 knockdown or current inhibition increases DRG neuronal excitability.

Lastly, we examined whether rats that received L4/5 DRG injections of Kcna2 antisense RNA showed behavioral changes in nociceptive thresholds. Injection of AAV5-Kcna2 antisense, but not of AAV5-EGFP, produced mechanical and cold hypersensitivities as demonstrated by ipsilateral decreases in paw withdrawal threshold and paw withdrawal latency, respectively (n=14 rats per group, P<0.01; FIG. 7i). These hypersensitivities developed by 4 to 6 weeks, reached a peak at 8 weeks and were maintained for at least 12 weeks (FIG. 7i). Neither AAV5-Kcna2 antisense nor AAV5-EGFP affected locomotor functions (data not shown). These findings suggest that Kcna2 antisense RNA-triggered DRG Kcna2 downregulation induces mechanical and cold hypersensitivities, two main clinical symptoms of neuropathic pain.

Figures 8C, 8D, 8E:
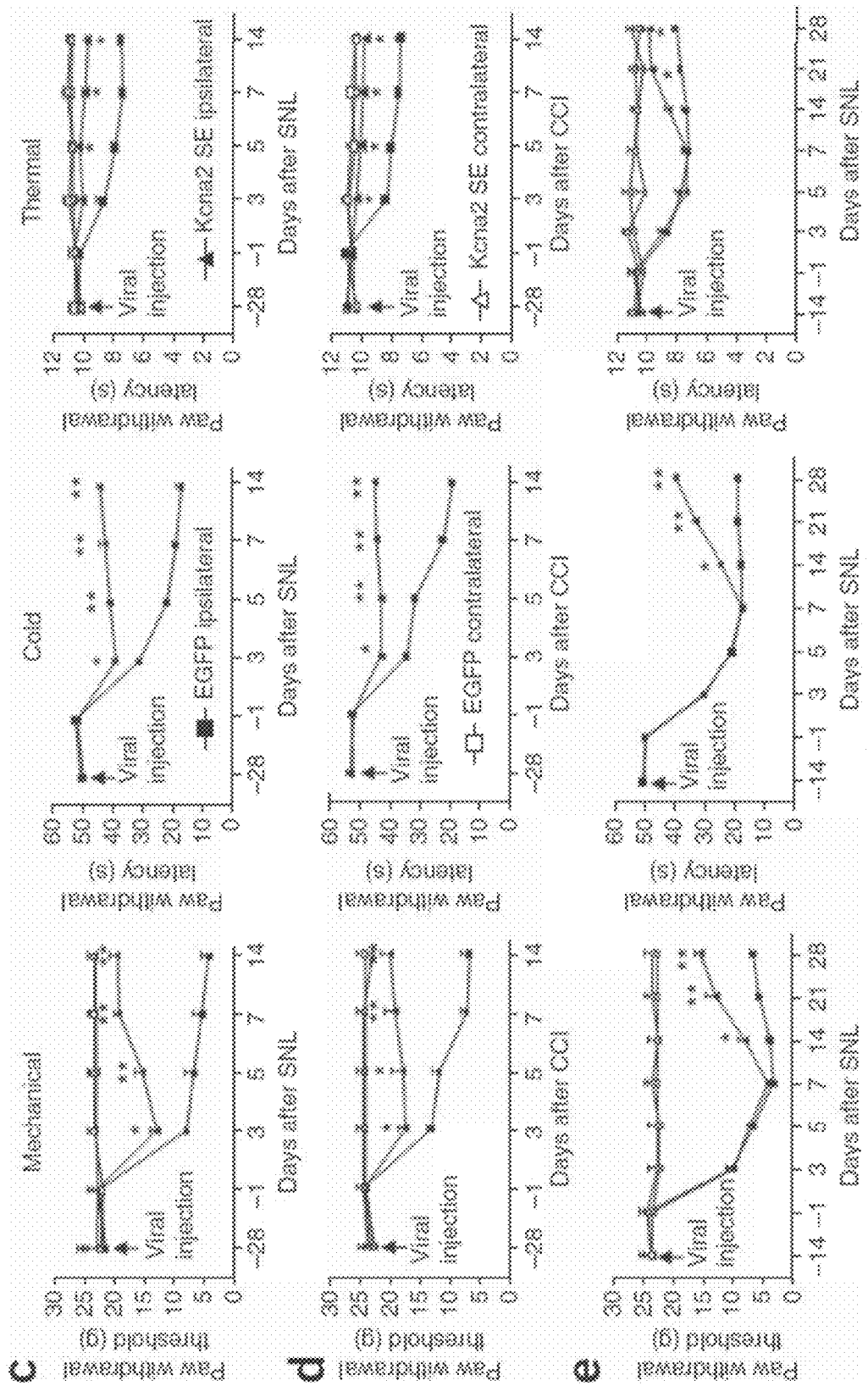

Blocking DRG Kcna2 Antisense RNA Attenuates Neuropathic Pain. Finally, we inquired whether blocking nerve injury-induced upregulation of DRG Kcna2 antisense RNA would affect reductions in DRG Kcna2 expression and nociceptive thresholds after nerve injury. Consistent with our in vitro work (FIG. 6a,b), in vivo DRG injection of AAV5-Kcna2 sense fragment, but not AAV5-EGFP, significantly blocked upregulation of Kcna2 antisense RNA and downregulation of Kcna2 mRNA and protein in the injured DRGs after SNL or chronic constriction injury (CCI) (FIG. 8a,b). These effects occurred at 4 weeks and were maintained for at least 12 weeks after viral injection. Injection of AAV5-Kcna2 sense fragment alone did not alter basal expression of Kcna2 mRNA and Kcna2 protein or Kcna2 antisense RNA in the ipsilateral L5 DRG of sham-operated rats (FIG. 8a,b). To examine the role of Kcna2 antisense RNA in neuropathic pain induction, we subjected rats to SNL 4 weeks after DRG viral injection, as our pilot work showed that there was too little Kcna2 sense fragment to block SNL-induced Kcna2 antisense RNA expression before that time. SNL produced mechanical, cold and thermal hypersensitivities on the ipsilateral side in the EGFP-injected group (FIG. 8c). By contrast, hypersensitivity was attenuated in the Kcna2 sense fragment-injected rats (FIG. 8c). Paw withdrawal threshold to mechanical stimulation and paw withdrawal latency to cold and thermal stimuli were higher in the Kcna2 sense fragment-injected rats than in the EGFP-injected group from days 3 to 14 after SNL (FIG. 8c). We observed similar effects of AAV5-Kcna2 sense fragment on neuropathic pain development in the CCI model as well (FIG. 8d).

To further investigate the role of Kcna2 antisense RNA in neuropathic pain maintenance, we subjected rats to SNL 2 weeks after DRG viral injection. Mechanical, cold and thermal hypersensitivities were completely developed in both the Kcna2 sense fragment-injected and EGFP-injected rats on day 7 after SNL (FIG. 8e). These hypersensitivities were markedly attenuated on days 14, 21 and 28 after SNL in the Kcna2 sense fragment-injected rats (FIG. 8e). Neither AAV5-Kcna2 sense fragment nor AAV5-EGFP affected paw withdrawal threshold or latency on the contralateral side (FIG. 8c-e), affected locomotor function (data not shown) or altered basal responses to mechanical or cold stimuli in sham-operated rats (data not shown). Our findings indicate that Kcna2 antisense RNA contributes to neuropathic pain development and maintenance and that blocking its expression may have clinical applications in neuropathic pain treatment.

Discussion lncRNAs were recently shown to occur naturally in mammals18,19. They can be transcribed in cis from the opposing DNA strands of the RNA genes at the same genomic locus or in trans from a locus different from that of the RNA genes25. Rat Kcna2 antisense RNA is more than 2.5 kb and complementary to most of the Kcna2 RNA sequence, strongly suggesting that Kcna2 antisense RNA is a cis-encoded lncRNA. Of note, the Kcna2 antisense RNA exhibits the same splicing patterns as the Kcna2 sense RNA. Because the splice junctions of the Kcna2 sense gene are canonical (that is, they follow the GT-AG rule), splicing mechanisms of the Kcna2 antisense gene are unusual and merit further investigation.

Expression of native Kcna2 antisense RNA, like that of the mRNA, can be regulated by transcriptional activation. Nerve injury-induced upregulation of Kcna2 antisense RNA was triggered through DRG MZF1 activation. Whether other transcription factors also trigger activation of Kcna2 antisense transcription is unknown. Additionally, the increase in antisense RNA might be caused by increases in RNA stability and/or other epigenetic modification. These possibilities cannot be excluded and will be addressed in our future studies.

Kcna2 antisense RNA functions as a biologically active regulator of Kcna2 mRNA in primary afferent neurons. Normally, Kcna2 antisense RNA was expressed at a low level in a few (mostly medium-sized) DRG neurons, whereas Kcna2 protein was highly expressed in most medium- or large-sized DRG neurons9. Of note, injury to the peripheral nerve not only increased Kcna2 antisense RNA expression but also altered its subpopulation distribution pattern to large- and medium-sized neurons in the injured DRG. Conversely, Kcna2 mRNA and Kcna2 protein were correspondingly downregulated in these neurons5-10. This downregulation is likely caused by the increase in Kcna2 antisense RNA, as overexpression of Kcna2 antisense RNA in cultured HEK-293T cells or DRG neurons selectively and specifically inhibited Kcna2 mRNA and protein expression. This effect may be related to the extensive overlap of their complementary regions, including the transcription and translation initiation sites. DRG Kcna subunits are functional heteromultimers9,26-28. The expression of other Kcna subunits was unaffected, likely because they lack complementary sequences and the inhibitory effect of Kcna2 antisense RNA occurs before the formation of heteromultimers. However, the fact that Kcna2 downregulation markedly reduced total voltage-gated potassium current density in large and medium DRG neurons indicates that Kcna2 is a key subunit in determining voltage-gated potassium channel function in these neurons. Minimal reduction was observed in small DRG neurons, possibly because Kcna2 is poorly expressed in those neurons9.

We found that selective reduction of Kcna2 expression in DRG by Kcna2 antisense RNA decreased total voltage-gated potassium current, depolarized the resting membrane potential, decreased current threshold for activation of action potentials and increased the number of action potentials in large and medium DRG neurons. Depolarization of DRG neuronal resting membrane potential by DRG Kcna2 downregulation was also reported previously29,30. Kcna2 antisense RNA did not affect action potential threshold or amplitude in DRG neurons, as these two parameters may be determined predominantly by Na+ channels. Kcna2 knockdown by Kcna2 antisense RNA produced a modest, but insignificant, increase in DRG neuronal membrane input resistances, an observation that is consistent with the fact that membrane input resistance also depends on other voltage-gated potassium channels (for example, Kcna1, Kcna4), hyperpolarization-activated cyclic nucleotide-gated channels31,32 and chloride channels33 expressed on DRG neuronal membrane. In addition, the depolarized resting membrane potential by itself may increase resting potassium conductance31,32, which may counteract Kcna2 deficiency-induced increase in membrane input resistance. The increase in membrane input resistance caused by blocking voltage-gated potassium current in DRG neurons was observed only in the absence of a significant resting membrane potential depolarization34. The fact membrane input resistance is unchanged but that resting membrane potentials are markedly depolarized in DRG neurons has been reported after peripheral nerve injury35.

Nerve injury-induced increases in spontaneous ectopic activity, which have been found primarily in injured myelinated afferents and the corresponding large and medium DRG neuronal bodies36,37, are considered to play a leading role in the genesis of neuropathic pain1,3. Peripheral nerve injury increased Kcna2 antisense RNA mainly in medium and large DRG neurons. Kcna2 antisense RNA-induced depolarization of the resting membrane potential of DRG neurons may render those neurons more prone to hyperexcitability. Indeed, animals that overexpressed Kcna2 antisense RNA exhibited significant hypersensitivities to mechanical and noxious cold stimuli. Substance P and CGRP in the injured myelinated fibers and in large and medium DRG neurons are markedly increased as early as 2 d after nerve injury3,38. It is very likely that the increase in excitability of large and medium DRG neurons drives the release of these neurotransmitters from their primary afferent terminals and leads to spinal central sensitization, which contributes to the development and maintenance of neuropathic pain. This conclusion is supported by the fact that blocking SNL-evoked upregulation of Kcna2 antisense RNA reversed the reduction in DRG Kcna2 and attenuated induction and maintenance of nerve injury-induced mechanical and cold hypersensitivities. It is still a puzzle how blocking SNL-induced downregulation of DRG Kcna2 almost abolishes SNL-induced pain hypersensitivity at the late time points. We think that blocking DRG Kcna2 downregulation causes persistent reduction in DRG excitability that may enhance the decrease in primary afferent transmitter release, resulting in attenuation of spinal central sensitization formation. Persistent reduction in DRG neuronal excitability may also block further SNL-induced changes in the expression of other DRG genes, including transcription factors that govern gene expression. This activity could create positive feedback to further reduce DRG excitability. These potential mechanisms remain to be confirmed. Taken together, our findings suggest that Kcna2 antisense RNA is an endogenous trigger in neuropathic pain development and maintenance. Regulation of Kcna2 channel expression may be a target for treating neuropathic pain.

In summary, identification of Kcna2 antisense RNA may point to regulation of Kcna2 channel expression and neuronal excitability, a novel mechanism in neuropathic pain, and potential targets for the development of therapies of this disorder. Because Kcna2 antisense RNA, Kcna2 mRNA and Kcna2 protein are expressed broadly, they may be implicated in other pathological processes. In addition, demonstration of Kcna2 antisense RNA may challenge current molecular methodologies. For example, we cannot use sense probes usually designed as negative controls, as they detect endogenous antisense RNAs in in situ hybridization, or oligo(dT) primers, as they allow reverse transcription of both sense and antisense RNAs. Therefore, our findings not only provide conceptual advances regarding the development of neuropathic pain but also will affect the conduct of research in other fields.

I claim:

1. A method for treating neuropathic pain comprising the step of administering to a patient in need thereof a composition comprising a recombinant Kcna2 sense fragment, wherein the recombinant Kcna2 sense fragment comprises SEQ ID NO:6.

2. The method of claim 1, wherein the composition further comprises a pharmaceutically acceptable carrier.

3. The method of claim 1, wherein the patient is human.

4. The method of claim 1, wherein the composition is administered to the dorsal root ganglion or to the spinal cord of the patient.

5. The method of claim 1, wherein the composition is administered parenterally.

6. A method for treating neuropathic pain comprising the step of administering to a patient in need thereof a composition comprising a recombinant vector encoding a Kcna2 sense fragment shown in SEQ ID NO:6.

7. The method of claim 6, wherein the composition further comprises a pharmaceutically acceptable carrier.

8. The method of claim 6, wherein the patient is human.

9. The method of claim 6, wherein the composition is administered to the dorsal root ganglion or to the spinal cord of the patient.

10. The method of claim 6, wherein the composition is administered parenterally.

* * * * *